US010695179B2

(12) United States Patent
Alon

(10) Patent No.: US 10,695,179 B2
(45) Date of Patent: Jun. 30, 2020

(54) DELIVERING A CONSTRICTING CORD TO A CARDIAC VALVE ANNULUS USING BALLOON-ASSISTED POSITIONING

(71) Applicant: Cardiac Implants LLC, Tarrytown, NY (US)

(72) Inventor: David Alon, Zichron Yaacov (IL)

(73) Assignee: Cardiac Implants LLC, Tarrytown, NY (US)

( * ) Notice: Subject to any disclaimer, the term of this patent is extended or adjusted under 35 U.S.C. 154(b) by 254 days.

(21) Appl. No.: 15/699,814

(22) Filed: Sep. 8, 2017

(65) Prior Publication Data

US 2018/0071098 A1  Mar. 15, 2018

Related U.S. Application Data

(60) Provisional application No. 62/519,529, filed on Jun. 14, 2017, provisional application No. 62/395,357, filed on Sep. 15, 2016.

(51) Int. Cl.
*A61F 2/24* (2006.01)
*A61F 2/00* (2006.01)
(Continued)

(52) U.S. Cl.
CPC ........ *A61F 2/2466* (2013.01); *A61B 17/0401* (2013.01); *A61B 17/0487* (2013.01); *A61F 2/0077* (2013.01); *A61F 2/2412* (2013.01); *A61F 2/2433* (2013.01); *A61F 2/2445* (2013.01); *A61B 2017/00243* (2013.01); *A61B 2017/0409* (2013.01);
(Continued)

(58) Field of Classification Search
CPC .... A61F 2/2466; A61F 2/2433; A61F 2/2412; A61F 2/2445; A61F 2/2409; A61F 2/2442; A61F 2/2448; A61F 2/2451; A61F 2/2454; A61F 2/2457; A61F 2/246; A61F 2/2463
See application file for complete search history.

(56) References Cited

U.S. PATENT DOCUMENTS 6,425,916 B1 * 7/2002 Garrison ............... A61F 2/2418
623/1.26
8,430,926 B2   4/2013 Kirson
(Continued)

OTHER PUBLICATIONS

International Search Report and Written Opinion for PCT/US2018/014318 dated Jul. 11, 2018.
(Continued)

*Primary Examiner* — Tan-Uyen T Ho
*Assistant Examiner* — Chima U Igboko
(74) *Attorney, Agent, or Firm* — Potomac Law Group, PLLC

(57) ABSTRACT

A constricting cord can be delivered to the vicinity of an annulus using an apparatus that includes a set of support arms, with a respective anchor launcher supported by each of the support arms. An inflatable first balloon is configured to push the support arms away from each other when the first balloon is inflated. An inflatable second balloon is mounted to a shaft and is configured for inflation when the second balloon is disposed distally beyond the first balloon. In some embodiments, the distal balloon is inflated while it is in a ventricle. In some embodiments, the distal balloon is inflated while it is in a pulmonary artery.

15 Claims, 26 Drawing Sheets

(51) Int. Cl.
*A61B 17/04* (2006.01)
*A61F 2/95* (2013.01)
*A61B 17/00* (2006.01)

(52) U.S. Cl.
CPC ........... *A61B 2017/0464* (2013.01); *A61F 2002/9517* (2013.01); *A61F 2220/0016* (2013.01)

(56) References Cited

U.S. PATENT DOCUMENTS

| | | | |
|---|---|---|---|
| RE46,126 E | 8/2016 | Kirson | |
| RE46,127 E | 8/2016 | Kirson | |
| 9,517,130 B1 | 12/2016 | Alon et al. | |
| 2002/0198585 A1* | 12/2002 | Wisselink | A61F 2/07 623/1.11 |
| 2004/0210304 A1* | 10/2004 | Seguin | A61F 2/2409 623/2.11 |
| 2005/0187578 A1 | 8/2005 | Rosenberg et al. | |
| 2008/0262609 A1 | 10/2008 | Gross et al. | |
| 2010/0076548 A1* | 3/2010 | Konno | A61F 2/2409 623/2.1 |
| 2010/0240951 A1 | 9/2010 | Catanese et al. | |
| 2010/0280604 A1 | 11/2010 | Zipory et al. | |
| 2011/0166649 A1 | 7/2011 | Gross et al. | |
| 2012/0283757 A1 | 11/2012 | Miller et al. | |
| 2014/0309730 A1* | 10/2014 | Alon | A61F 2/2409 623/2.11 |
| 2015/0127094 A1 | 5/2015 | Saiahieh et al. | |
| 2016/0120645 A1 | 5/2016 | Alon | |
| 2016/0135953 A1 | 5/2016 | Alon et al. | |
| 2016/0228252 A1 | 8/2016 | Keidar | |
| 2016/0235526 A1 | 8/2016 | Lashinski et al. | |
| 2018/0071094 A1 | 3/2018 | Alon | |
| 2018/0071095 A1 | 3/2018 | Alon et al. | |
| 2018/0071096 A1 | 3/2018 | Alon et al. | |
| 2018/0071097 A1 | 3/2018 | Alon | |
| 2018/0071099 A1 | 3/2018 | Alon | |
| 2018/0116800 A1 | 5/2018 | Alon | |
| 2018/0133009 A1 | 5/2018 | Alon | |

OTHER PUBLICATIONS

International Search Report and Written Opinion issued in application No. PCT/US2017/050716, dated Jan. 18, 2018.

* cited by examiner

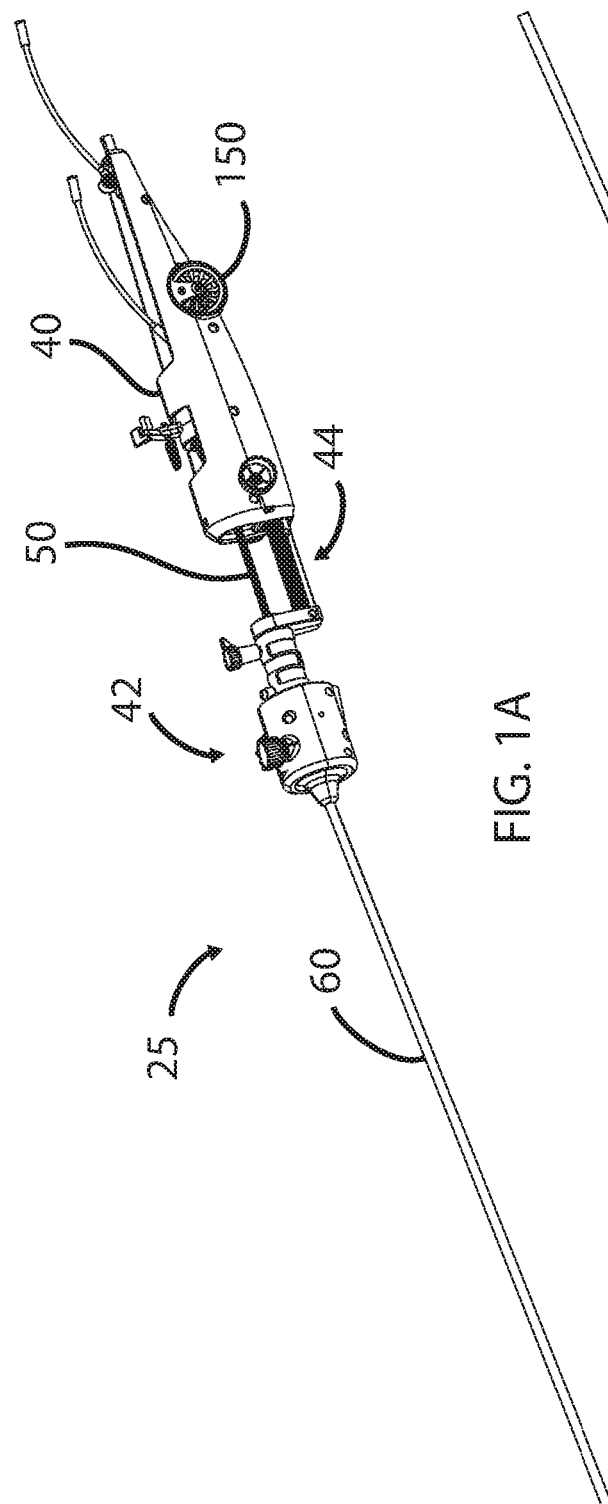
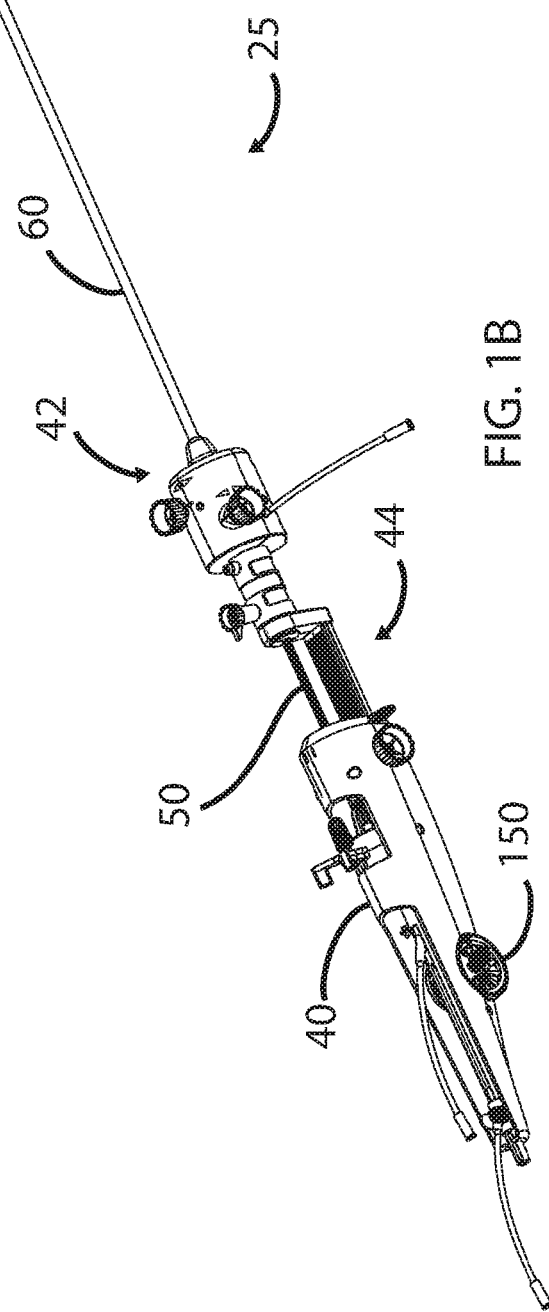
FIG. 1A
FIG. 1B

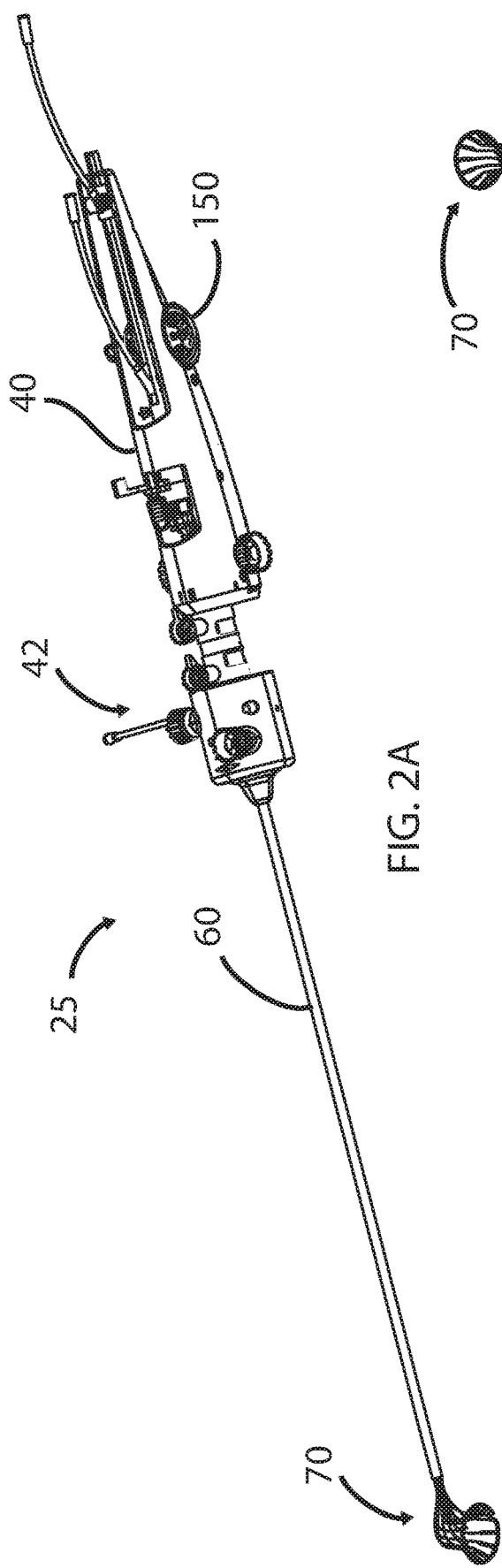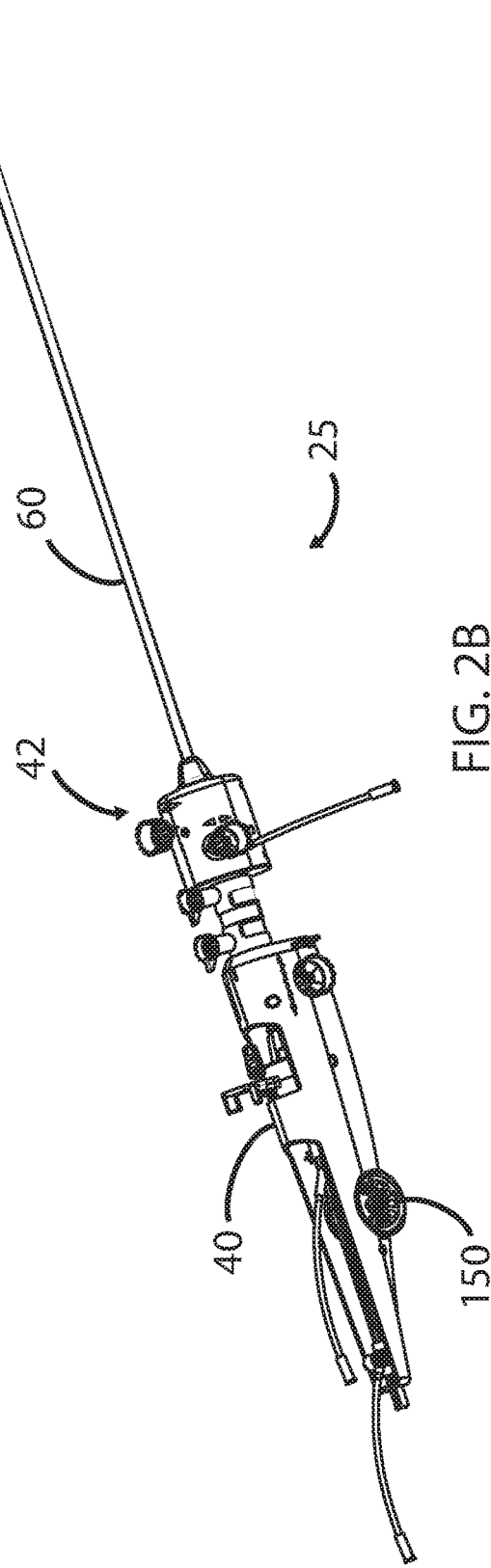
FIG. 2A
FIG. 2B

DELIVERING A CONSTRICTING CORD TO A CARDIAC VALVE ANNULUS USING BALLOON-ASSISTED POSITIONING

CROSS REFERENCE TO RELATED APPLICATIONS

This Application claims the benefit of U.S. Provisional Application 62/395,357, filed Sep. 15, 2016, and U.S. Provisional Application 62/519,529, filed Jun. 14, 2017, each of which is incorporated herein by reference in its entirety.

BACKGROUND

A variety of approaches for delivering and installing a cinching cord or an annulus ring to a cardiac valve annulus are described in U.S. application Ser. No. 14/364,060 (published as US 2014/0309730) and Ser. No. 14/895,711 (published as US 2016/0120645), each of which is incorporated by reference herein in its entirety.

SUMMARY OF THE INVENTION

One aspect of the invention is directed to a first apparatus for delivering a cinching cord to the vicinity of an annulus. The first apparatus comprises an elongated core, at least four support arms, and at least four anchor launchers. The elongated core has (a) a distal end, (b) a main channel that runs through the core in a proximal-to-distal direction, (c) at least four first channels that run through the core in a proximal-to-distal direction, each of the first channels being dimensioned to accommodate a respective pull wire, and (d) at least one second channel that runs through the core in a proximal-to-distal direction, dimensioned to accommodate a first proximal portion and a second proximal portion of a cinching cord. The at least four support arms are mounted to the core and extend distally beyond the distal end of the core. Each of the anchor launchers has a distal end, and each of the anchor launchers is supported by a respective one of the support arms.

The support arms are configured to support arms hold the distal ends of the anchor launchers at positions that correspond to a shape of the annulus, with the distal ends of the anchor launchers distributed about a perimeter of the shape of the annulus.

Some embodiments of the first apparatus further comprise at least four anchors, a cinching cord, and at least four pull wires. Each of the anchors is disposed in a respective one of the anchor launchers. The cinching cord has a distal loop portion, a first proximal portion, and a second proximal portion, wherein the first proximal portion and the second proximal portion are disposed in the at least one second channel, and wherein the anchors are connected to the distal loop portion of the cinching cord. Each of the pull wires is disposed in a respective one of the first channels, wherein each of the pull wires is operatively connected to a respective one of the anchor launchers so that pulling on a respective pull wire will launch the respective anchor.

Some embodiments of the first apparatus further comprise a plurality of support rings and a plurality of support rods. The support arms are affixed to the support rings and extend in a distal direction from the support rings. The support rods are affixed to the support rings, and the support rods extend in a proximal direction from the support rings. In these embodiments, the core has a plurality of third channels that run through the core in a proximal-to-distal direction and are dimensioned to accommodate the support rods, and the support arms are mounted to the core by inserting the support rods into the third channels. Optionally, these embodiments further comprise a radio-opaque material distributed on the support rods in an asymmetric pattern.

In some embodiments of the first apparatus, the main channel is centered about the radial center of the core. In some embodiments of the first apparatus, each of the first channels and each of the at least one second channel is located at the same radial distance from the radial center of the core. In some embodiments of the first apparatus, each of the first channels comprises a lumen, and each of the at least one second channel comprises a lumen. In some embodiments of the first apparatus, each of the first channels and each of the at least one second channel is located at the same radial distance from the radial center of the core, each of the first channels comprises a lumen, and each of the at least one second channel comprises a lumen.

In some embodiments of the first apparatus, the at least four support arms comprises at least eight support arms, the at least four first channels comprises at least eight first channels, and the at least four anchor launchers comprises at least eight anchor launchers. In some embodiments of the first apparatus, the annulus is a mitral valve annulus. In other embodiments of the first apparatus, the annulus is a tricuspid valve annulus.

Some embodiments of the first apparatus further comprise an outer sleeve disposed around the core, the outer sleeve having a distal end. The outer sleeve is slidable with respect to the core between an extended position and a retracted position. When the outer sleeve is in the extended position, the support arms and the anchor launchers are disposed within the outer sleeve. When the outer sleeve is in the retracted position, the anchor launchers and at least a portion of the support arms extend distally beyond the distal end of the outer sleeve.

Some embodiments of the first apparatus further comprise a first sleeve disposed around the core, the first sleeve having a distal portion, wherein the first sleeve is slidable with respect to the core between an extended position and a retracted position; and a removable second sleeve slidably disposed around the distal portion of the first sleeve. When the second sleeve is in an initial position, the support arms and the anchor launchers are disposed within the second sleeve, and when the second sleeve is removed and the first sleeve is in the retracted position, the anchor launchers are free to move to positions that correspond to the shape of the annulus.

Another aspect of the invention is directed to a second apparatus for delivering a cinching cord to the vicinity of an annulus. The second apparatus comprises an elongated core, at least support arms, and at least eight anchor launchers. The elongated core has (a) a distal end, (b) a main channel that runs through the core in a proximal-to-distal direction, (c) at least eight first channels that run through the core in a proximal-to-distal direction at positions that are radially beyond the main channel, each of the first channels being dimensioned to accommodate a respective pull wire, and (d) a plurality of second channels that run through the core in a proximal-to-distal direction at positions that are radially beyond the main channel, each of the second channels being dimensioned to accommodate a respective proximal portion of a cinching cord. The at least eight support arms are mounted to the core and extend distally beyond the distal end of the core. Each of the anchor launchers has a distal end, and each of the anchor launchers is supported by a respective one of the support arms. The support arms are configured to hold the distal ends of the anchor launchers at positions that correspond to a shape of the annulus, with the distal ends of the anchor launchers distributed about a perimeter of the shape of the annulus.

Some embodiments of the second apparatus further comprise at least eight anchors, a cinching cord, and at least eight pull wires. Each of the anchors is disposed in a respective one of the anchor launchers. The cinching cord has a distal loop portion, a first proximal portion, and a second proximal portion, wherein the first proximal portion and the second proximal portion are disposed in respective ones of the second channels, and wherein the at least eight anchors are connected to the distal loop portion of the cinching cord. Each of the pull wires is disposed in a respective one of the first channels, and each of the pull wires is operatively connected to a respective one of the anchor launchers so that pulling on a respective pull wire will launch the respective anchor.

Some embodiments of the second apparatus further comprise a plurality of support rings and a plurality of support rods. The support arms are affixed to the support rings and extend in a distal direction from the support rings. The support rods are affixed to the support rings, and the support rods extend in a proximal direction from the support rings. In these embodiments, the core has a plurality of third channels that run through the core in a proximal-to-distal direction and are dimensioned to accommodate the support rods, and the support arms are mounted to the core by inserting the support rods into the third channels. Optionally, these embodiments further comprise a radio-opaque material distributed on the support rods in an asymmetric pattern.

In some embodiments of the second apparatus, each of the first channels is located at the same radial distance from the radial center of the core. In some embodiments of the second apparatus, each of the first channels and each of the second channels is located at the same radial distance from the radial center of the core. In some embodiments of the second apparatus, each of the first channels comprises a lumen and each of the second channels comprises a lumen.

Some embodiments of the second apparatus further comprise a plurality of support rings, a plurality of support rods, and a radio opaque material. The support arms are affixed to the support rings and extend in a distal direction from the support rings. The support rods are affixed to the support rings, and the support rods extend in a proximal direction from the support rings. The radio-opaque material is distributed on the support rods in an asymmetric pattern. In these embodiments, the core has a plurality of third channels that run through the core in a proximal-to-distal direction and are dimensioned to accommodate the support rods, and the support arms are mounted to the core by inserting the support rods into the third channels. In these embodiments, each of the first channels and each of the second channels is located at the same radial distance from the radial center of the core, each of the first channels comprises a lumen, and each of the second channels comprises a lumen.

Some embodiments of the second apparatus further comprise an outer sleeve disposed around the core, the outer sleeve having a distal end. The outer sleeve is slidable with respect to the core between an extended position and a retracted position. When the outer sleeve is in the extended position, the support arms and the anchor launchers are disposed within the outer sleeve. When the outer sleeve is in the retracted position, the anchor launchers and at least a portion of the support arms extend distally beyond the distal end of the outer sleeve.

Some embodiments of the second apparatus further comprise a first sleeve disposed around the core, the first sleeve having a distal portion, wherein the first sleeve is slidable with respect to the core between an extended position and a retracted position; and a removable second sleeve slidably disposed around the distal portion of the first sleeve. When the second sleeve is in an initial position, the support arms and the anchor launchers are disposed within the second sleeve, and when the second sleeve is removed and the first sleeve is in the retracted position, the anchor launchers are free to move to positions that correspond to the shape of the annulus.

Another aspect of the invention is directed to a third apparatus for delivering an annulus ring to the vicinity of an annulus. The third apparatus comprises an elongated core, at least four support arms, and at least four anchor launchers. The elongated core has (a) a distal end, (b) a main channel that runs through the core in a proximal-to-distal direction, and (c) at least four lumens that run through the core in a proximal-to-distal direction. Each of the lumens is dimensioned to accommodate a respective pull wire. The support arms are mounted to the core and extend distally beyond the distal end of the core. Each of the anchor launchers has a distal end, and each of the anchor launchers is supported by a respective one of the support arms. The support arms are configured to hold the distal ends of the anchor launchers at positions that correspond to a shape of the annulus, with the distal ends of the anchor launchers distributed about a perimeter of the shape of the annulus.

Some embodiments of the third apparatus further comprise at least four anchors, an annulus ring, and at least four pull wires. In these embodiments, each of the anchors is disposed in a respective one of the anchor launchers and the anchors are connected to the annulus ring. Each of the pull wires is disposed in a respective one of the lumens, and each of the pull wires is operatively connected to a respective one of the anchor launchers so that pulling on a respective pull wire will launch the respective anchor.

Some embodiments of the third apparatus further comprise a plurality of support rings and a plurality of support rods. In these embodiments, the support arms are affixed to the support rings and extend in a distal direction from the support rings. The support rods are affixed to the support rings, and the support rods extend in a proximal direction from the support rings. The core has a plurality of support channels that run through the core in a proximal-to-distal direction and are dimensioned to accommodate the support rods, and the support arms are mounted to the core by inserting the support rods into the support channels. Optionally, these embodiments further comprise a radio-opaque material distributed on the support rods in an asymmetric pattern.

In some embodiments of the third apparatus, the main channel is centered about the radial center of the core and each of the lumens is located at the same radial distance from the radial center of the core. In some embodiments of the third apparatus, the at least four support arms comprises at least eight support arms, the at least four lumens comprises at least eight lumens, and the at least four anchor launchers comprises at least eight anchor launchers.

Some embodiments of the third apparatus further comprise an outer sleeve disposed around the core, the outer sleeve having a distal end. The outer sleeve is slidable with respect to the core between an extended position and a retracted position. When the outer sleeve is in the extended position, the support arms and the anchor launchers are disposed within the outer sleeve. When the outer sleeve is in the retracted position, the anchor launchers and at least a portion of the support arms extend distally beyond the distal end of the outer sleeve.

Some embodiments of the third apparatus further comprise a first sleeve disposed around the core, the first sleeve having a distal portion, wherein the first sleeve is slidable with respect to the core between an extended position and a retracted position; and a removable second sleeve slidably disposed around the distal portion of the first sleeve. When the second sleeve is in an initial position, the support arms and the anchor launchers are disposed within the second sleeve, and when the second sleeve is removed and the first sleeve is in the retracted position, the anchor launchers are free to move to positions that correspond to the shape of the annulus.

Another aspect of the invention is directed to a fourth apparatus for installing a cinching cord onto an annulus or onto tissue adjacent to the annulus. The fourth apparatus includes a housing, an elongated core, a cinching cord, at least four anchors, and first and second extension sections of cord. The elongated core is mounted with respect to the housing. The core has (a) a distal end, (b) a proximal end, (c) a first lumen that runs through the core in a proximal-to-distal direction, and (d) a second lumen that runs through the core in a proximal-to-distal direction. The cinching cord has a distal loop portion, a first proximal portion, and a second proximal portion, wherein the first proximal portion of the cinching cord extends distally beyond the distal end of the core, runs through the first lumen, and extends proximally beyond the proximal end of the core, and wherein the second proximal portion of the cinching cord extends distally beyond the distal end of the core, runs through the second lumen, and extends proximally beyond the proximal end of the core. The anchors are configured to anchor the distal loop portion of the cinching cord into the annulus or into tissue adjacent to the annulus. The first extension section of cord has a distal end and a proximal section, wherein the distal end of the first extension section is connected to the first proximal portion of the cinching cord. The second extension section of cord has a distal end and a proximal section, wherein the distal end of the second extension section is connected to the second proximal portion of the cinching cord. The first lumen is dimensioned to slidably accommodate the first proximal portion of the cinching cord and the first extension section of cord, and the second lumen is dimensioned to slidably accommodate the second proximal portion of the cinching cord and the second extension section of cord. The cinching cord, the first and second extension sections of cord, and the first and second lumens are configured so that after the distal loop portion of the cinching cord is anchored to the annulus or into the tissue adjacent to the annulus by the at least four anchors, progressive movement of the housing in a proximal direction will (a) cause the core to progressively move in a proximal direction with respect to the first and second proximal portions of the cinching cord and (b) cause the first and second extension sections of cord to be progressively drawn into the first and second lumens, respectively.

In some embodiments of the fourth apparatus, the cinching cord, the first extension section of cord, and the second extension section of cord are contiguous sections of a single cord.

Some embodiments of the fourth apparatus further comprise at least one spool rotatably mounted with respect to the housing. In these embodiments, the proximal section of the first extension section of cord is wound on the at least one spool, and the proximal section of the second extension section of cord is wound on the at least one spool. The cinching cord, the first and second extension sections of cord, the first and second lumens, and the at least one spool are configured so that after the distal loop portion of the cinching cord is anchored to the annulus or into the tissue adjacent to the annulus by the at least four anchors, progressive movement of the housing in a proximal direction will cause the first and second extension sections of cord to progressively unwind from the at least one spool.

Some embodiments of the fourth apparatus further comprise a lock that selectively either (a) prevents the at least one spool from rotating or (b) allows the at least one spool to rotate. In these embodiments, the at least one spool has spokes or markings that enhance visibility of rotation of the at least one spool, and the at least one spool is arranged with respect to the housing so that at least a portion of the spokes or markings is visible from outside the housing. The cinching cord, the first extension section of cord, and the second extension section of cord are contiguous sections of a single cord.

Another aspect of the invention is directed to a fifth apparatus for installing a cinching cord onto an annulus or onto tissue adjacent to the annulus. The fifth apparatus comprises a housing, at least one spool, an elongated core, a cinching cord, at least four anchors, at least four anchor launchers, at least four support arms, and first and second extension sections of cord. The at least one spool is rotatably mounted with respect to the housing. The elongated core is mounted with respect to the housing. The core has (a) a distal end, (b) a proximal end, (c) a first lumen that runs through the core in a proximal-to-distal direction, and (d) a second lumen that runs through the core in a proximal-to-distal direction. The cinching cord has a distal loop portion, a first proximal portion, and a second proximal portion, wherein the first proximal portion of the cinching cord extends distally beyond the distal end of the core, runs through the first lumen, and extends proximally beyond the proximal end of the core, and wherein the second proximal portion of the cinching cord extends distally beyond the distal end of the core, runs through the second lumen, and extends proximally beyond the proximal end of the core. The anchors are configured to anchor the distal loop portion of the cinching cord into the annulus or into tissue adjacent to the annulus. Each of the anchor launchers is configured to launch a respective one of the at least four anchors into the annulus or into the tissue adjacent to the annulus, and each of the anchor launchers has a distal end. The support arms are mounted to the core and extend distally beyond the distal end of the core and support the anchor launchers. The support arms are shaped to hold the distal ends of the anchor launchers at positions that correspond to a shape of the annulus, with the distal ends of the anchor launchers distributed about a perimeter of the shape of the annulus. The first extension section of cord has a distal end and a proximal section. The distal end of the first extension section is connected to the first proximal portion of the cinching cord, and the proximal section of the first extension section is wound on the at least one spool. The second extension section of cord has a distal end and a proximal section, and the distal end of the second extension section is connected to the second proximal portion of the cinching cord. The proximal section of the second extension section is wound on the at least one spool. The first lumen is dimensioned to slidably accommodate the first proximal portion of the cinching cord and the first extension section of cord, and the second lumen is dimensioned to slidably accommodate the second proximal portion of the cinching cord and the second extension section of cord. The cinching cord, the first and second extension sections of cord, the first and second lumens, and the at least one spool are configured so that after the distal loop portion of the cinching cord is anchored to the annulus or into the tissue adjacent to the annulus by the at least four anchors, progressive movement of the housing in a proximal direction will (a) cause the core to progressively move in a proximal direction with respect to the first and second proximal portions of the cinching cord and (b) cause the first and second extension sections of cord to progressively unwind from the at least one spool and be progressively drawn into the first and second lumens, respectively.

In some embodiments of the fifth apparatus, the cinching cord, the first extension section of cord, and the second extension section of cord are contiguous sections of a single cord. In some of these embodiments, the single cord is an ultra high molecular weight polyethylene cord. In other embodiments of the fifth apparatus, the distal end of the first extension section of cord is fastened to the first proximal portion of the cinching cord, and wherein the distal end of the second extension section of cord is fastened to the second proximal portion of the cinching cord.

Some embodiments of the fifth apparatus further comprise a lock that selectively either (a) prevents the at least one spool from rotating or (b) allows the at least one spool to rotate. In some of these embodiments, the lock comprises a removable pin that prevents the at least one spool from rotating when the pin is installed, and allows the at least one spool to rotate when the pin is removed.

In some embodiments of the fifth apparatus, the at least one spool is arranged with respect to the housing so that at least a portion of the at least one spool is visible from outside the housing. In some embodiments of the fifth apparatus, the at least one spool has spokes or markings that enhance visibility of rotation of the at least one spool, and the at least one spool is arranged with respect to the housing so that at least a portion of the spokes or markings is visible from outside the housing.

In some embodiments of the fifth apparatus, the at least one spool comprises a first spool upon which the proximal section of the first extension section of cord is wound, and a second spool upon which the proximal section of the second extension section of cord is wound. In some embodiments of the fifth apparatus, the at least one spool comprises a single spool having (a) a first region upon which the proximal section of the first extension section of cord is wound and (b) a second region upon which the proximal section of the second extension section of cord is wound, wherein the first region and the second region are non-overlapping. In some embodiments of the fifth apparatus, the first lumen and the second lumen have smooth polymer walls.

Some embodiments of the fifth apparatus further comprise at least four pull wires and a spring-loaded actuator. Each of the pull wires has a proximal end and a distal end, wherein the distal end of each of the pull wires is operatively connected to a respective one of the anchor launchers such that pulling the respective pull wire in a proximal direction causes the respective anchor launcher to launch a respective anchor. The spring-loaded actuator is configured to hold the proximal ends of each of the pull wires steady prior to actuation of a trigger, and to pull the proximal ends of each of the pull wires in a proximal direction upon actuation of the trigger.

In some embodiments of the fifth apparatus, the at least four anchors comprises at least eight anchors, the at least four anchor launchers comprises at least eight anchor launchers, and the at least four support arms comprises at least eight support arms. In some embodiments of the fifth apparatus, the annulus is a mitral valve annulus. In other embodiments of the fifth apparatus, the annulus is a tricuspid valve annulus.

Some embodiments of the fifth apparatus further comprise a lock that selectively either (a) prevents the at least one spool from rotating or (b) allows the at least one spool to rotate. In these embodiments, the at least one spool has spokes or markings that enhance visibility of rotation of the at least one spool, and the at least one spool is arranged with respect to the housing so that at least a portion of the spokes or markings is visible from outside the housing. The cinching cord, the first extension section of cord, and the second extension section of cord are contiguous sections of a single cord. In addition, the at least four anchors comprises at least eight anchors, the at least four anchor launchers comprises at least eight anchor launchers, and the at least four support arms comprises at least eight support arms.

In some embodiments of the fifth apparatus, the at least one spool comprises a single spool having (a) a first region upon which the proximal section of the first extension section of cord is wound and (b) a second region upon which the proximal section of the second extension section of cord is wound, and the first region and the second region are non-overlapping.

Some embodiments of the fifth apparatus further comprise an outer sleeve disposed around the core, the outer sleeve having a distal end. The outer sleeve is slidable with respect to the core between an extended position and a retracted position. When the outer sleeve is in the extended position, the support arms and the anchor launchers are disposed within the outer sleeve. And when the outer sleeve is in the retracted position, the anchor launchers and at least a portion of the support arms extend distally beyond the distal end of the outer sleeve. Some of these embodiments further comprise a rack and pinion mounted with respect to the housing, with the rack connected to the outer sleeve such that actuation of the pinion causes the outer sleeve to move between the extended position and the retracted position.

Some embodiments of the fifth apparatus further comprise a first sleeve disposed around the core, the first sleeve having a distal portion, wherein the first sleeve is slidable with respect to the core between an extended position and a retracted position; and a removable second sleeve slidably disposed around the distal portion of the first sleeve. When the second sleeve is in an initial position, the support arms and the anchor launchers are disposed within the second sleeve, and when the second sleeve is removed and the first sleeve is in the retracted position, the anchor launchers are free to move to positions that correspond to the shape of the annulus.

Another aspect of the invention is directed to a first method for preventing tissue ingrowth from interfering with the cinching of an annulus using a cinching cord. The cinching cord has a distal loop portion disposed within a sleeve that promotes tissue ingrowth, a first proximal portion, and a second proximal portion. The first method comprises manipulating the cinching cord so that (a) the distal loop portion of the cinching cord disposed within the sleeve is in the vicinity of the annulus and (b) the first and second proximal portions of the cinching cord run in a proximal direction from the distal loop portion of the cinching cord. The first method also comprises anchoring the distal loop portion of the cinching cord to at least one of the annulus and tissue adjacent to the annulus, and covering the first and second proximal portions of the cinching cord with a material that resists tissue ingrowth. The first method also comprises, subsequent to the anchoring step and the covering step, waiting for tissue ingrowth to strengthen a bond between the distal loop portion of the cinching cord and at least one of the annulus and the tissue adjacent to the annulus. The first method also comprises, subsequent to the waiting step, cinching the annulus by pulling the first and second proximal portions of the cinching cord so as to reduce a diameter of the annulus. The first method also comprises, subsequent to the cinching step, fastening the cinching cord so that the cinching cord holds the annulus in a reduced diameter state. Preferably, the covering step comprises sliding an elongated cord protector having a first lumen and a second lumen over the first and second proximal portions of the cinching cord so that the first proximal portion of the cinching cord passes through the first lumen and that the second proximal portion of the cinching cord passes through the second lumen.

Some embodiments of the first method further comprise threading the first proximal portion of the cinching cord through the first lumen using a first threading cord and threading the second proximal portion of the cinching cord through the second lumen using a second threading cord. In these embodiments, prior to the threading steps, the first threading cord is disposed in the first lumen and the second threading cord is disposed in the second lumen. In these embodiments, in the sliding step, the first and second proximal portions of the cinching cord operate as guidewires over which the elongated cord protector is slid, and the elongated cord protector is slid into a position at which a distal end of the elongated cord protector is adjacent to the distal loop portion of the cinching cord.

Some embodiments of the first method further comprise the step of removing the elongated cord protector subsequent to the waiting step and prior to the cinching step. Some embodiments of the first method further comprise the step of sliding a stiffening member in a proximal to distal direction through a third lumen that runs through the elongated cord protector, wherein the sliding step is implemented subsequent to the anchoring step and prior to the covering step.

In some embodiments of the first method, the cinching step comprises advancing a thrust tube in a distal direction over the first and second proximal portions of the cinching cord until the thrust tube reaches the distal loop portion of the cinching cord and subsequently pressing the thrust tube in a distal direction while pulling the first and second proximal portions of the cinching cord in a proximal direction.

In some embodiments of the first method, the fastening step comprises fastening two portions of the cinching cord together using at least one of a knot, a clamp, and a crimped fastener. In some embodiments of the first method, in the anchoring step, the distal loop portion of the cinching cord is anchored by anchoring the sleeve to at least one of the annulus and the tissue adjacent to the annulus using a plurality of anchors.

In some embodiments of the first method, in the anchoring step, the distal loop portion of the cinching cord is anchored by anchoring a plurality of anchors to at least one of the annulus and the tissue adjacent to the annulus, each of the anchors having an eyelet, wherein the cinching cord passes through the eyelets in the anchors.

In some embodiments of the first method, the covering step comprises sliding an elongated cord protector having at least one lumen over the first and second proximal portions of the cinching cord so that the first and second proximal portions of the cinching cord pass through the at least one lumen. In some of these embodiments, the first method further comprises removing the elongated cord protector subsequent to the waiting step and prior to the cinching step.

Another aspect of the invention is directed to a sixth apparatus for preventing tissue ingrowth from interfering with the operation of a cinching cord that is implanted in a subject's body. The cinching cord has a distal loop portion, a first proximal portion, and a second proximal portion. The sixth apparatus comprises a flexible elongated body having a proximal end and a distal end. The elongated body has a first lumen that runs between the proximal end and the distal end and a second lumen that runs between the proximal end and the distal end. The first lumen is dimensioned to slidably accommodate the first proximal portion of the cinching cord and the second lumen is dimensioned to slidably accommodate the second proximal portion of the cinching cord. The elongated body, the first lumen, and the second lumen are configured to facilitate slidable installation of the elongated body over the first and second proximal portions of the cinching cord such that the elongated body covers the first and second proximal portions of the cinching cord, with the first proximal portion of the cinching cord disposed in the first lumen and the second proximal portion of the cinching cord disposed in the second lumen. The elongated body prevents tissue ingrowth into the elongated body, and the elongated body also prevents tissue ingrowth into the first and second proximal portions of the cinching cord when the elongated body covers the first and second proximal portions of the cinching cord.

Some embodiments of the sixth apparatus further comprise a first threading cord that runs through the first lumen and extends distally beyond the distal end of the elongated body, and a second threading cord that runs through the second lumen and extends distally beyond the distal end of the elongated body. Some of these embodiments further comprise a sterile envelope, and the elongated body, the first threading cord that runs through the first lumen, and the second threading cord that runs through the second lumen are all packaged inside the sterile envelope.

In some embodiments of the sixth apparatus, the first threading cord is configured to draw the first proximal portion of the cinching cord into the first lumen and the second threading cord is configured to draw the second proximal portion of the cinching cord into the second lumen, so that the first and the second proximal portions of the cinching cord can operate as a guidewires over which the elongated body can be slid into a position at which the distal end of the elongated body is adjacent to the distal loop portion of the cinching cord. In some of these embodiments, the first threading cord extends proximally beyond the proximal end of the elongated body and the second threading cord extends proximally beyond the proximal end of the elongated body.

In some embodiments of the sixth apparatus, the elongated body is formed from at least one of polyurethane and silicone. In some embodiments of the sixth apparatus, the elongated body has a length between 35 and 65 cm and a diameter between 1 and 4 mm. In some embodiments of the sixth apparatus, the elongated body has a length between 45 and 55 cm. In some embodiments of the sixth apparatus, the elongated body has a diameter between 1.5 and 2.5 mm. In some embodiments of the sixth apparatus, the elongated body has a length between 45 and 55 cm and a diameter between 1.5 and 2.5 mm. In some embodiments of the sixth apparatus, the first lumen has a diameter between 0.2 and 1 mm and the second lumen has a diameter between 0.2 and 1 mm. In some embodiments of the sixth apparatus, the elongated body has a third lumen that is open at the proximal end, closed at the distal end, and extends through at least three-fourths of the elongated body, and the third lumen is dimensioned to slidably accommodate a stiffening wire. In some embodiments of the sixth apparatus, the elongated body has a third lumen that is open at the proximal end, closed at the distal end, and extends through at least three-fourths of the elongated body, and the third lumen has a diameter between 0.2 and 1 mm. Some embodiments of the sixth apparatus further comprise a radio-opaque marker disposed near the distal end of the elongated body.

Some embodiments of the sixth apparatus further comprise a first threading cord that runs through the first lumen and extends distally beyond the distal end of the elongated body, and a second threading cord that runs through the second lumen and extends distally beyond the distal end of the elongated body. In these embodiments, the first threading cord is configured to draw the first proximal portion of the cinching cord into the first lumen and the second threading cord is configured to draw the second proximal portion of the cinching cord into the second lumen, so that the first and the second proximal portions of the cinching cord can operate as a guidewires over which the elongated body can be slid into a position at which the distal end of the elongated body is adjacent to the distal loop portion of the cinching cord. In these embodiments, the elongated body is formed from at least one of polyurethane and silicone, the elongated body has a length between 45 and 55 cm and a diameter between 1.5 and 2.5 mm, and the first lumen has a diameter between 0.2 and 1 mm and the second lumen has a diameter between 0.2 and 1 mm. Some of these embodiments further comprise a radio-opaque marker disposed near the distal end of the elongated body. In some of these embodiments, the elongated body has a third lumen that is open at the proximal end, closed at the distal end, and extends through at least nine-tenths of the elongated body, and the third lumen has a diameter between 0.2 and 1 mm.

Another aspect of the invention is directed to a seventh apparatus for delivering an annulus ring or a cinching cord to the vicinity of an annulus. The seventh apparatus comprises an elongated core, at least four support arms, at least four anchor launchers, an inflatable balloon, and at least one retainer cord. The elongated core has a distal end. The support arms mounted to the core and extend distally beyond the distal end of the core. Each of the anchor launchers has a distal end, and each of the anchor launchers is supported by a respective one of the support arms. The inflatable balloon is disposed between the between the support arms, configured so that when the balloon is inflated, the balloon will push the support arms away from each other. The at least one retainer cord is connected to the support arms and arranged with respect to the support arms to encompass the balloon and prevent the balloon from slipping out between the support arms.

In some embodiments of the seventh apparatus, the at least one retainer cord comprises a single retainer cord that encompasses the balloon and prevents the balloon from slipping out between the support arms. In some of these embodiments, the single retainer cord is connected to the support arms using at least one knot. In some of these embodiments, the single retainer cord comprises at least one of silk, nylon, polypropylene, and polyester.

In some embodiments of the seventh apparatus, each of the support arms is enclosed in a sleeve, and the at least one retainer cord is connected to the support arms by threading the at least one retainer cord through a hole in each of the sleeves. In some embodiments of the seventh apparatus, each of the support arms is enclosed in a sleeve, and the at least one retainer cord is connected to the support arms by threading the at least one retainer cord through a hole in each of the sleeves and tying a knot at each of the sleeves. In some embodiments of the seventh apparatus, the at least one retainer cord comprises at least two segments of cord that collectively encompass the balloon and prevent the balloon from slipping out between the support arms.

Some embodiments of the seventh apparatus further comprise a cinching cord and at least four anchors, wherein each of the anchors is disposed in a respective one of the anchor launchers and connected to the cinching cord. In these embodiments, the support arms are configured to hold the distal ends of the anchor launchers at positions that correspond to a shape of the annulus, with the distal ends of the anchor launchers distributed about a perimeter of the shape of the annulus.

Some embodiments of the seventh apparatus further comprises an annulus ring and at least four anchors, wherein each of the anchors is disposed in a respective one of the anchor launchers and connected to the annulus ring. In these embodiments, the support arms are configured to hold the distal ends of the anchor launchers at positions that correspond to a shape of the annulus, with the distal ends of the anchor launchers distributed about a perimeter of the shape of the annulus.

In some embodiments of the seventh apparatus, the at least four support arms comprises at least eight support arms, and the at least four anchor launchers comprises at least eight anchor launchers.

Some embodiments of the seventh apparatus further comprise an outer sleeve disposed around the core, the outer sleeve having a distal end. The outer sleeve is slidable with respect to the core between an extended position and a retracted position. When the outer sleeve is in the extended position, the support arms, the anchor launchers, the balloon, and the at least one retainer cord are disposed within the outer sleeve. When the outer sleeve is in the retracted position, the anchor launchers, the at least one retainer cord, and at least a portion of the support arms extend distally beyond the distal end of the outer sleeve.

Some embodiments of the seventh apparatus further comprise a first sleeve disposed around the core, the first sleeve having a distal portion, wherein the first sleeve is slidable with respect to the core between an extended position and a retracted position; and a removable second sleeve slidably disposed around the distal portion of the first sleeve. When the second sleeve is in an initial position, the support arms, the anchor launchers, the balloon, and the at least one retainer cord are disposed within the second sleeve. When the second sleeve is removed and the first sleeve is in the retracted position, the anchor launchers are free to move to positions that correspond to the shape of the annulus.

Another aspect of the invention is directed to an eighth apparatus for delivering an annulus ring or a cinching cord to the vicinity of an annulus. The eighth apparatus comprises an elongated core, at least four support arms, at least four anchor launchers, a shaft, an inflatable balloon, and at least one retainer cord. The elongated core has a distal end and a channel that runs through the core in a proximal-to-distal direction. The support arms are mounted to the core and extend distally beyond the distal end of the core. Each of the anchor launchers has a distal end, and each of the anchor launchers is supported by a respective one of the support arms. The shaft is slidably disposed within the channel, and the shaft has an inflation lumen. The inflatable balloon is mounted to the shaft and connected to the inflation lumen so as to permit inflation of the balloon via the inflation lumen. The balloon is movable to a first position between the support arms by slidably adjusting a position of the shaft, and the balloon is configured so that when the balloon is inflated at the first position, the balloon will push the support arms away from each other. The at least one retainer cord is connected to the support arms and arranged with respect to the support arms to, when the balloon is at the first position, encompass the balloon and prevent the balloon from slipping out between the support arms.

In some embodiments of the eighth apparatus, the balloon is movable to a second position that is within the channel and proximal of the support arms by slidably adjusting a position of the shaft. In some embodiments of the eighth apparatus, the balloon is movable to a second position that is distally beyond the anchor launchers by slidably adjusting a position of the shaft.

In some embodiments of the eighth apparatus, the at least one retainer cord comprises a single retainer cord that encompasses the balloon and prevents the balloon from slipping out between the support arms. In the some of these embodiments, the single retainer cord is connected to the support arms using at least one knot. In some of these embodiments, the single retainer cord comprises at least one of silk, nylon, polypropylene, and polyester.

In some embodiments of the eighth apparatus, each of the support arms is enclosed in a sleeve, and the at least one retainer cord is connected to the support arms by threading the at least one retainer cord through a hole in each of the sleeves. In some embodiments of the eighth apparatus, each of the support arms is enclosed in a sleeve, and the at least one retainer cord is connected to the support arms by threading the at least one retainer cord through a hole in each of the sleeves and tying a knot at each of the sleeves. In some embodiments of the eighth apparatus, the at least one retainer cord comprises at least two segments of cord that collectively encompass the balloon and prevent the balloon from slipping out between the support arms.

Some embodiments of the eighth apparatus further comprise a cinching cord and at least four anchors, wherein each of the anchors is disposed in a respective one of the anchor launchers and connected to the cinching cord. In these embodiments, the support arms are configured to hold the distal ends of the anchor launchers at positions that correspond to a shape of the annulus, with the distal ends of the anchor launchers distributed about a perimeter of the shape of the annulus.

Some embodiments of the eighth apparatus further comprise an annulus ring and at least four anchors, wherein each of the anchors is disposed in a respective one of the anchor launchers and connected to the annulus ring. In these embodiments, the support arms are configured to hold the distal ends of the anchor launchers at positions that correspond to a shape of the annulus, with the distal ends of the anchor launchers distributed about a perimeter of the shape of the annulus.

In some embodiments of the eighth apparatus, the at least four support arms comprises at least eight support arms, the at least four anchor launchers comprises at least eight anchor launchers.

Some embodiments of the eighth apparatus further comprise an outer sleeve disposed around the core, the outer sleeve having a distal end. The outer sleeve is slidable with respect to the core between an extended position and a retracted position. When the outer sleeve is in the extended position, the support arms, the anchor launchers, the balloon, and the at least one retainer cord are disposed within the outer sleeve. When the outer sleeve is in the retracted position, the anchor launchers, the at least one retainer cord, and at least a portion of the support arms extend distally beyond the distal end of the outer sleeve.

Some embodiments of the eighth apparatus further comprise a first sleeve disposed around the core, the first sleeve having a distal portion, wherein the first sleeve is slidable with respect to the core between an extended position and a retracted position; and a removable second sleeve slidably disposed around the distal portion of the first sleeve. When the second sleeve is in an initial position, the support arms, the anchor launchers, the balloon, and the at least one retainer cord are disposed within the second sleeve. When the second sleeve is removed and the first sleeve is in the retracted position, the anchor launchers are free to move to positions that correspond to the shape of the annulus.

Another aspect of the invention is directed to a ninth apparatus for delivering an annulus ring or a cinching cord to the vicinity of an annulus. The ninth apparatus comprises an elongated core, at least four support arms, at least four anchor launchers, a first shaft, an inflatable first balloon, a nosecone, a second shaft, and an inflatable second balloon. The elongated core has a distal end and a channel that runs through the core in a proximal-to-distal direction. The support arms are mounted to the core and extend distally beyond the distal end of the core. Each of the anchor launchers has a distal end, and each of the anchor launchers is supported by a respective one of the support arms. The first shaft is disposed within the channel, and the first shaft has a first inflation lumen. The inflatable first balloon is mounted to the first shaft and connected to the first inflation lumen so as to permit inflation of the first balloon via the first inflation lumen, and the first balloon is configured so that when the first balloon is inflated at a first position, the first balloon will push the support arms away from each other. The second shaft is slidably disposed within the channel, and the second shaft has a second inflation lumen. The inflatable second balloon is mounted to the second shaft and connected to the second inflation lumen so as to permit inflation of the second balloon via the second inflation lumen, and the second balloon is disposed distally beyond the first balloon.

In some embodiments of the ninth apparatus, the first shaft is slidably disposed within the channel, and the first balloon is movable to the first position by slidably adjusting a position of the first shaft. In some of these embodiments, the first balloon is movable to a second position that is within the channel and proximal of the support arms by slidably adjusting a position of the first shaft.

Some embodiments of the ninth apparatus further comprise an outer sleeve disposed around the core, the outer sleeve having a distal end. The outer sleeve is slidable with respect to the core between an extended position and a retracted position. When the outer sleeve is in the extended position, the support arms, the anchor launchers, and the first balloon are disposed within the outer sleeve. When the outer sleeve is in the retracted position, the anchor launchers and at least a portion of the support arms extend distally beyond the distal end of the outer sleeve. Some of these embodiments further comprise a nosecone that is movable between a proximal position and a distal position, such that when the nosecone is in the proximal position and the outer sleeve is in the extended position, the nosecone is disposed at the distal end of the outer sleeve.

In some embodiments of the ninth apparatus that include a nosecone, the second shaft extends distally beyond the nosecone and the second balloon is located distally beyond the nosecone. In some embodiments of the ninth apparatus, the nosecone is mounted to the second shaft, and the nosecone is movable between the proximal position and the distal position by slidably adjusting a position of the second shaft.

In some embodiments of the ninth apparatus that include a nosecone, the first shaft is slidably disposed within the channel, and first balloon is movable to the first position by slidably adjusting a position of the first shaft. The second shaft extends distally beyond the nosecone and the second balloon is located distally beyond the nosecone. The nosecone is mounted to the second shaft, and the nosecone is movable between the proximal position and the distal position by slidably adjusting a position of the second shaft.

Some embodiments of the ninth apparatus that include a nosecone further comprise a third shaft slidably disposed within the channel. In these embodiments, the nosecone is mounted to the third shaft, and the nosecone is movable between the proximal position and the distal position by slidably adjusting a position of the third shaft. In some embodiments of the ninth apparatus, the nosecone is located distally beyond the second balloon.

Some embodiments of the ninth apparatus further comprise a cinching cord and at least four anchors. In these embodiments, each of the anchors is disposed in a respective one of the anchor launchers and connected to the cinching cord. The support arms are configured to hold the distal ends of the anchor launchers at positions that correspond to a shape of the annulus, with the distal ends of the anchor launchers distributed about a perimeter of the shape of the annulus.

Some embodiments of the ninth apparatus further comprise an annulus ring and at least four anchors, wherein each of the anchors is disposed in a respective one of the anchor launchers and connected to the annulus ring. In these embodiments, the support arms are configured to hold the distal ends of the anchor launchers at positions that correspond to a shape of the annulus, with the distal ends of the anchor launchers distributed about a perimeter of the shape of the annulus.

In some embodiments of the ninth apparatus, the at least four support arms comprises at least eight support arms, and the at least four anchor launchers comprises at least eight anchor launchers. In some embodiments of the ninth apparatus, the annulus is a mitral valve annulus. In other embodiments of the ninth apparatus, the annulus is a tricuspid valve annulus.

Another aspect of the invention is directed to a second method for implanting an annulus ring or a cinching cord to a heart valve annulus or into tissue adjacent to the annulus. The annulus is disposed between an atrium and a ventricle of the heart and the heart has an apex. The second method comprises delivering an assembly into the atrium, wherein the assembly includes (a) the annulus ring or the cinching cord, (b) a plurality of anchors connected to the annulus ring or the cinching cord, and (c) a plurality of anchor launchers configured to launch the anchors into the annulus or into the tissue adjacent to the annulus. The assembly is supported by a supporting member. The second method also comprises positioning the assembly such that the annulus ring or the cinching cord is adjacent to the annulus or the tissue adjacent to the annulus on the atrium side of the annulus. The second method also comprises advancing an inflatable balloon into the ventricle, wherein the balloon is supported by the supporting member, and inflating the balloon while the balloon is in the ventricle. The second method also comprises adjusting a position of the balloon within the ventricle so that when a selected portion of the cardiac cycle occurs while the balloon is inflated, forces on the balloon will urge the balloon toward the apex of the heart, which will urge the supporting member toward the apex of the heart, which will urge the annulus ring or the cinching cord towards the annulus or towards the tissue adjacent to the annulus. The second method also comprises determining a time when the selected portion of the cardiac cycle is occurring while the inflated balloon is at the adjusted position, and triggering the anchor launchers so that the anchor launchers launch the anchors into the annulus or into the tissue adjacent to the annulus during the selected portion of the cardiac cycle while the inflated balloon is at the adjusted position.

In some embodiments of the second method, the determining comprises detecting when the supporting member is being pulled in a distal direction. In some embodiments of the second method, the advancing comprises sliding a shaft to which the inflatable balloon is mounted in a distal direction with respect to the supporting member. In some embodiments of the second method, the positioning comprises inflating an additional balloon between a plurality of support arms that support the anchor launchers so that the additional balloon pushes the support arms away from each other.

In some embodiments of the second method, the delivering comprises (a) introducing the annulus ring or the cinching cord, the anchors, and the anchor launchers into the atrium while the cinching cord, the anchors, and the anchor launchers are collapsed within an outer sleeve; and (b) retracting the outer sleeve so that the cinching cord, the anchors, and the anchor launchers extend beyond a distal end of the outer sleeve. In some embodiments of the second method, the valve annulus is a mitral valve annulus. In some embodiments of the second method, the valve annulus is a tricuspid valve annulus.

Another aspect of the invention is directed to a third method for implanting an annulus ring or a cinching cord to a tricuspid valve annulus or into tissue adjacent to the annulus. The third method comprises delivering an assembly into a right atrium, wherein the assembly includes (a) the annulus ring or the cinching cord, (b) a plurality of anchors connected to the annulus ring or the cinching cord, and (c) a plurality of anchor launchers configured to launch the anchors into the annulus or into the tissue adjacent to the annulus, wherein the assembly is supported by a supporting member. The third method also comprises positioning the assembly such that the annulus ring or the cinching cord is adjacent to the annulus or the tissue adjacent to the annulus on the right atrium side of the annulus, and advancing an inflatable balloon in a deflated state into a pulmonary artery. The balloon is supported by the supporting member. The third method also comprises inflating the balloon while the balloon is in the pulmonary artery, so as to anchor the balloon at a location, and adjusting a position of the assembly while the balloon remains anchored at the location so as to press the annulus ring or the cinching cord towards the annulus or towards the tissue adjacent to the annulus. The third method also comprises launching the anchors into the annulus or into the tissue adjacent to the annulus after the adjusting, deflating the balloon, and withdrawing the assembly.

In some embodiments of the third method, the pulmonary artery is a right pulmonary artery.

In some embodiments of the third method, the pulmonary artery is a left pulmonary artery.

In some embodiments of the third method, the advancing comprises sliding a shaft to which the inflatable balloon is mounted in a distal direction with respect to the supporting member.

In some embodiments of the third method, the positioning comprises inflating an additional balloon between a plurality of support arms that support the anchor launchers so that the additional balloon pushes the support arms away from each other.

In some embodiments of the third method, the delivering comprises introducing the annulus ring or the cinching cord, the anchors, and the anchor launchers into the right atrium while the cinching cord, the anchors, and the anchor launchers are collapsed within an outer sleeve.

Another aspect of the invention is directed to a tenth apparatus for installing a cinching cord onto an annulus or onto tissue adjacent to the annulus. This apparatus comprises a housing, an elongated core, a cinching cord, at least four support arms, at least four anchors, at least four anchor launchers, at least one wire, and a pushing member. The elongated core is mounted with respect to the housing. The core has (a) a distal end, (b) at least one second channel that runs through the core in a proximal-to-distal direction, and (c) at least one fourth channel that runs through the core in a proximal-to-distal direction. The cinching cord has a distal loop portion, a first proximal portion, and a second proximal portion, wherein the first proximal portion of the cinching cord is slidably disposed within the at least one second channel and extends distally beyond the distal end of the core, and wherein the second proximal portion of the cinching cord is slidably disposed within the at least one second channel and extends distally beyond the distal end of the core. The support arms are mounted to the core and extend distally beyond the distal end of the core. The anchors are configured to anchor the distal loop portion of the cinching cord into the annulus or into the tissue adjacent to the annulus. Each of the anchor launchers is supported by a respective one of the support arms, and each of the anchor launchers is configured to launch a respective one of the anchors into the annulus or into the tissue adjacent to the annulus. The at least one wire (i) is slidably disposed within the at least one fourth channel, (ii) has a distal end that extends distally beyond the distal end of the core, and (iii) has a proximal end that extends proximally beyond the fourth channel. The pushing member is affixed to the distal end of the at least one wire such that pushing the proximal end of the at least one wire in a distal direction will push the pushing member in a distal direction. The cinching cord and the at least one second channel are configured so that after the distal loop portion of the cinching cord is anchored to the annulus or into the tissue adjacent to the annulus by the at least four anchors, progressive movement of the housing in a proximal direction will cause the core to progressively move in a proximal direction with respect to the first and second proximal portions of the cinching cord. The pushing member is configured so that after the distal loop portion of the cinching cord is anchored to the annulus or into the tissue adjacent to the annulus by the at least four anchors, pushing the pushing member in a distal direction will hinder dislodgement of the anchors during the movement of the housing in the proximal direction.

In some embodiments of the tenth apparatus, the distal loop portion of the cinching cord is covered by a sleeve that promotes tissue ingrowth.

In some embodiments of the tenth apparatus, the pushing member has at least one passage, and the first proximal portion and the second proximal portion of the cinching cord are slidably disposed in the at least one passage.

In some embodiments of the tenth apparatus, the pushing member has a distal end and a proximal end, and at least one passage that passes through the pushing member in a proximal to distal direction, and the first proximal portion and the second proximal portion of the cinching cord are slidably disposed in the at least one passage.

In some embodiments of the tenth apparatus, the pushing member comprises a hollow cylinder aligned so that an axial axis of the hollow cylinder is parallel to the at least one wire, and the first proximal portion and the second proximal portion of the cinching cord are slidably disposed within the hollow cylinder.

In some embodiments of the tenth apparatus, the at least one second channel comprises a plurality of lumens, and each of the first proximal portion of the cinching cord and the second proximal portion of the cinching cord is slidably disposed within a respective one of the plurality of lumens. In some of these embodiments, the at least one wire comprises a plurality of wires, the at least one fourth channel comprises a plurality of channels, and each of the plurality of wires is slidably disposed within a respective one of the plurality of channels.

In some embodiments of the tenth apparatus, the pushing member is configured so that after the distal loop portion of the cinching cord is anchored to the annulus or into the tissue adjacent to the annulus by the at least four anchors, pushing the pushing member in a distal direction will press the cinching cord against the annulus or the tissue adjacent to the annulus.

Some embodiments of the tenth apparatus further comprise at least one crush-resistant channel disposed distally beyond the distal end of the core, wherein the first and second proximal portions of the cinching cord are slidably disposed within the at least one crush-resistant channel. In some of these embodiments, before the distal loop portion of the cinching cord is anchored to the annulus or into the tissue adjacent to the annulus by the at least four anchors, the at least one crush-resistant channel extends to the pushing member. In some of these embodiments, the at least one crush-resistant channel is supported by at least one support arm that is affixed to the core.

In some embodiments of the tenth apparatus, the at least one second channel comprises a plurality of lumens, and each of the first proximal portion of the cinching cord and the second proximal portion of the cinching cord is slidably disposed within a respective one of the plurality of lumens. The at least one wire comprises a plurality of wires, the at least one fourth channel comprises a plurality of channels, and each of the plurality of wires is slidably disposed within a respective one of the plurality of channels. The pushing member is configured so that after the distal loop portion of the cinching cord is anchored to the annulus or into the tissue adjacent to the annulus by the at least four anchors, pushing the pushing member in a distal direction will press the cinching cord against the annulus or the tissue adjacent to the annulus. In some of these embodiments, the pushing member has a distal end and a proximal end, and at least one passage that passes through the pushing member in a proximal to distal direction. The first proximal portion and the second proximal portion of the cinching cord are slidably disposed in the at least one passage.

Another aspect of the invention is directed to a fourth method of attaching a cinching cord with a distal loop portion to an annulus or to tissue adjacent to the annulus. The fourth method comprises delivering the distal loop portion of the cinching cord to a vicinity of the annulus using a percutaneous delivery tool, and launching at least four anchors into the annulus or into the tissue adjacent to the annulus. The at least four anchors are configured to affix the distal loop portion of the cinching cord to the annulus or to the tissue adjacent to the annulus. The fourth method also comprises withdrawing the percutaneous delivery tool in a proximal direction after the at least four anchors have been launched, and pressing a pushing member in a distal direction so that the pushing member holds a portion of the cinching cord against the annulus or against the tissue adjacent to the annulus with enough pressure to prevent dislodgment of any of the at least four anchors during the withdrawal of the percutaneous delivery tool.

In some embodiments of the fourth method, the at least four anchors comprises at least eight anchors.

BRIEF DESCRIPTION OF THE DRAWINGS

FIGS. 1A and 1B are left and right side views, respectively, of an embodiment of an apparatus for installing a cinching cord or an annulus ring onto a cardiac valve annulus when the outer sleeve is in an extended position.

FIGS. 2A and 2B are left and right side views, respectively, of the FIG. 1 embodiment as it appears when the outer sleeve in a retracted position.

Various embodiments are described in detail below with reference to the accompanying drawings, wherein like reference numerals represent like elements.

DESCRIPTION OF THE PREFERRED EMBODIMENTS

Figure 3:
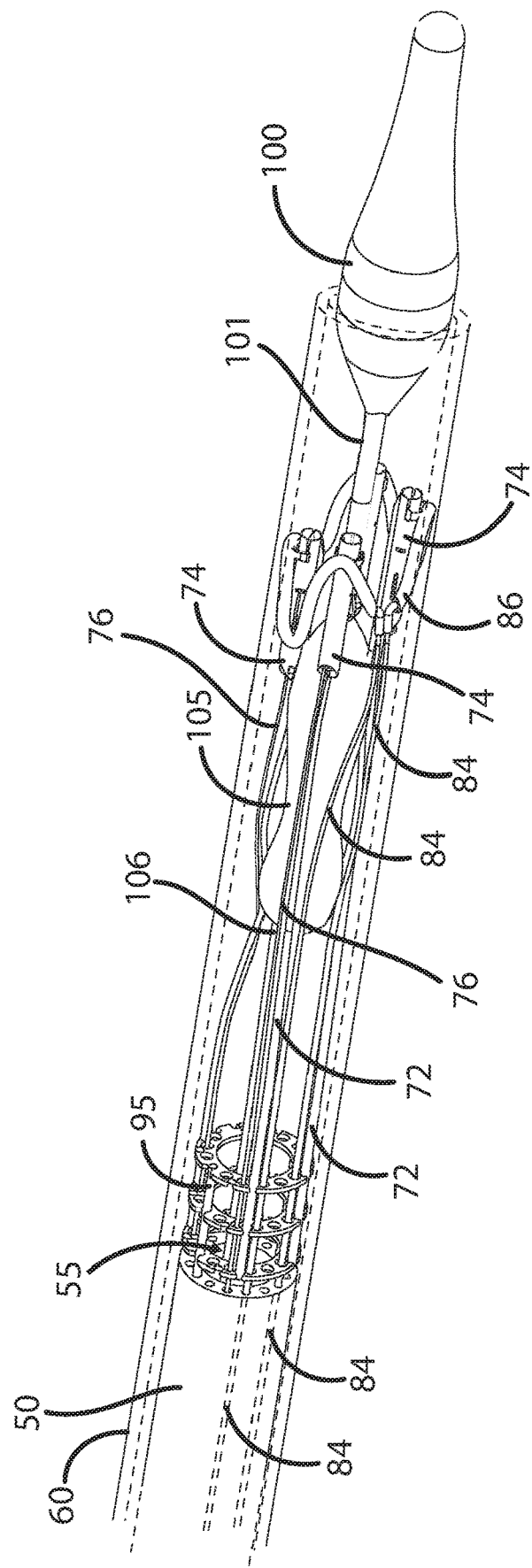
FIG. 3 is a detailed view of the distal end of the FIG. 1 embodiment when the outer sleeve is in the extended position.

This application describes methods and apparatuses for delivering and installing a cinching cord or an annulus ring into a cardiac valve annulus. In the cinching cord embodiments, once a cinching cord is installed into a cardiac valve annulus using the apparatuses and/or methods described herein, and after waiting for tissue ingrowth to occur, the cinching cord can be cinched in order to reduce the diameter of the annulus. These embodiments are useful for correcting or improving a variety of valve-related conditions (including but not limited to mitral valve regurgitation). In the annulus ring embodiments, an annulus ring is installed into a cardiac valve annulus to either (a) stabilize the shape of the annulus and prevent the annulus from expanding or (b) serve as the foundation onto which a replacement valve can be mounted. These embodiments are useful in the contexts of reducing valve regurgitation and cardiac valve replacement.

FIGS. 1A, 1B, 2A, and 2B are views of an apparatus 25 for delivering and installing a cinching cord or an annulus ring onto a cardiac valve annulus, such as the mitral valve annulus or the tricuspid valve annulus. In all four of these figures, the housing 40 is disposed on the proximal side of the apparatus 25, and the outer sleeve 60 is disposed at the distal side of the apparatus. More specifically, FIGS. 1A and 1B are left and right side views, respectively, of the apparatus 25 as it appears when the outer sleeve 60 of the apparatus is in an extended position; and FIGS. 2A and 2B are left and right side views, respectively, of the same apparatus 25 as it appears when the outer sleeve 60 is in a retracted position. When the outer sleeve 60 is retracted (as shown in FIGS. 2A and 2B), the distal assembly 70 (which includes the distal loop portion of the cinching cord or the annulus ring) extends out past the distal end of the outer sleeve 60. When the outer sleeve 60 is extended (as shown in FIGS. 1A and 1B), the distal assembly is collapsed and is disposed within the outer sleeve 60, and is therefore not visible in those figures. The extension and retraction of the outer sleeve 60 with respect to the core 50 is controlled by the sleeve retractor 44, which is described below.

FIG. 3 is a detailed view of the distal end of the apparatus 25 of FIG. 1 when the outer sleeve 60 is in its extended position. In this figure, the various components that make up the distal assembly 70 (shown in FIG. 2A) are all collapsed and contained within the outer sleeve 60. A preferred length of the outer sleeve 60 is 50 cm. In some embodiments, the outer diameter of the outer sleeve 60 is 22 French. Note that in alternative embodiments (e.g., the FIG. 17/18 embodiment discussed below), the one-piece outer sleeve 60 may be replaced with a plurality of sleeves.

The outer sleeve 60 is disposed around an elongated core 50, such that the outer sleeve is slidable with respect to the core between the extended position and the retracted position. In some embodiments, the core 50 is made of a flexible and noncompressible polymer. In some embodiments, the outer diameter of the core 50 is 5.7 mm. In alternative embodiments, the outer diameter of the core is between 5.0 and 6.5 mm. The gap between the outer surface of the core 50 and the inner diameter of the outer sleeve 60 is dimensioned to facilitates the slidable relationship between the outer sleeve 60 and the core 50. A main channel 55 runs through the center of the core 50. In some embodiments, the diameter of this main channel 55 is 3.7 mm. In alternative embodiments, this diameter can vary between 3.0 and 4.5 mm.

At least four support arms 72 are mounted to the core 50. The support arms 72 extend distally beyond the distal end of the core. Suitable materials for forming the support arms 70 to include stainless steel, nitinol, and other biocompatible metals. The support arms are flexible enough to collapse within the outer sleeve 60, but spring back to their original shape when extended distally beyond the confines of the outer sleeve 60.

At least four anchor launchers 74 are supported by respective ones of the at least four support arms 72. Each of the anchor launchers has a distal end. Suitable designs for the anchor launchers and the anchors contained therein can be found in U.S. application Ser. Nos. 14/895,711 and 15/163,453, each of which is incorporated herein by reference. An anchor is disposed in each of the anchor launchers 74. Each of the anchor launchers 74 is has a pull-wire trigger, and each of the pull wires 76 is operatively connected to one of the anchor launchers 74 so that pulling on a respective pull wire will launch the respective anchor.

Note that while FIG. 3 depicts four support arms 72 and four anchor launchers 74, it is more preferable to use at least eight support arms 72 and at least eight anchor launchers 74 (e.g. between 8 and 16 support arms and between 8 and 16 anchor launchers). But only four support arms and anchor launchers are depicted in FIG. 3 to make those components easier to see.

A cinching cord has a distal loop portion, a first proximal portion 84, and a second proximal portion 84. The distal loop portion 82 (shown in FIG. 6A) of the cinching cord is preferably surrounded by a sleeve 86 of material that promotes tissue ingrowth. The sleeve 86 is preferably soft and flexible. Suitable materials include a fabric braids (e.g., made of polyethylene terephthalate (PET) fabric. The anchors that are disposed within the anchor launchers 74 are connected to the distal loop portion 82 of the cinching cord. In some embodiments, this connection is implemented by connecting the anchors directly to the distal loop portion 82 of the cinching cord. In alternative embodiments, this connection is implemented by connecting the anchors to the sleeve 86 that surrounds the distal loop portion 82 of the cinching cord.

A shaft 106 is disposed within the main channel 55 and the shaft 106 has an inflation lumen. An inflatable balloon 105 is mounted to the shaft 106 and connected to the inflation lumen so as to permit inflation of the balloon 105 via the inflation lumen. The balloon 105 is configured so that when the outer sleeve 60 is retracted and the balloon 105 is inflated when disposed at a first position located between the support arms 72 (as best seen in FIGS. 7B and 7C), the balloon 105 will push the support arms 72 away from each other to help move the support arms 72 into positions at which the support arms 72 hold the distal ends of the anchor launchers 74 at positions that correspond to the shape of the annulus, with the distal ends of the anchor launchers 74 distributed about the perimeter of the shape of the annulus.

Note that even without the balloon 105, the support arms 72 are shaped to hold the distal ends of the anchor launchers 74 at positions that correspond to the shape of the annulus. But because the support arms 72 may become entangled with each other while they are collapsed within the outer sleeve 60, the balloon 105 is useful for untangling the support arms. In addition, the balloon 105 stiffens the structure formed by the support arms 72 and the distal loop portion 82 of the cinching cord so it becomes a relatively rigid structure that, in some preferred embodiments, fits very closely into the shape of the atrium.

Preferably, the shaft 106 is slidably disposed within the main channel 55, and the balloon 105 is movable to the first position by slidably adjusting a position of the shaft 106. Optionally, the balloon 105 may be movable to a second position that is within the main channel 55 and proximal of the support arms 72 by slidably adjusting a position of the shaft 106.

This embodiment also includes a nosecone 100 that is movable between a proximal position and a distal position. When the nosecone 100 is in the proximal position and the outer sleeve 60 is in the extended position, the nosecone 100 is disposed at the distal end of the outer sleeve 60, as seen in FIG. 3.

In some embodiments, the nosecone 100 is mounted to a nosecone shaft 101, and the nosecone is movable between the proximal position and a distal position by slidably adjusting a position of the nosecone shaft 101. FIG. 7A-D show the nosecone 100 when it is positioned at the distal position. In alternative embodiments, the nosecone is omitted entirely.

Figure 4A:
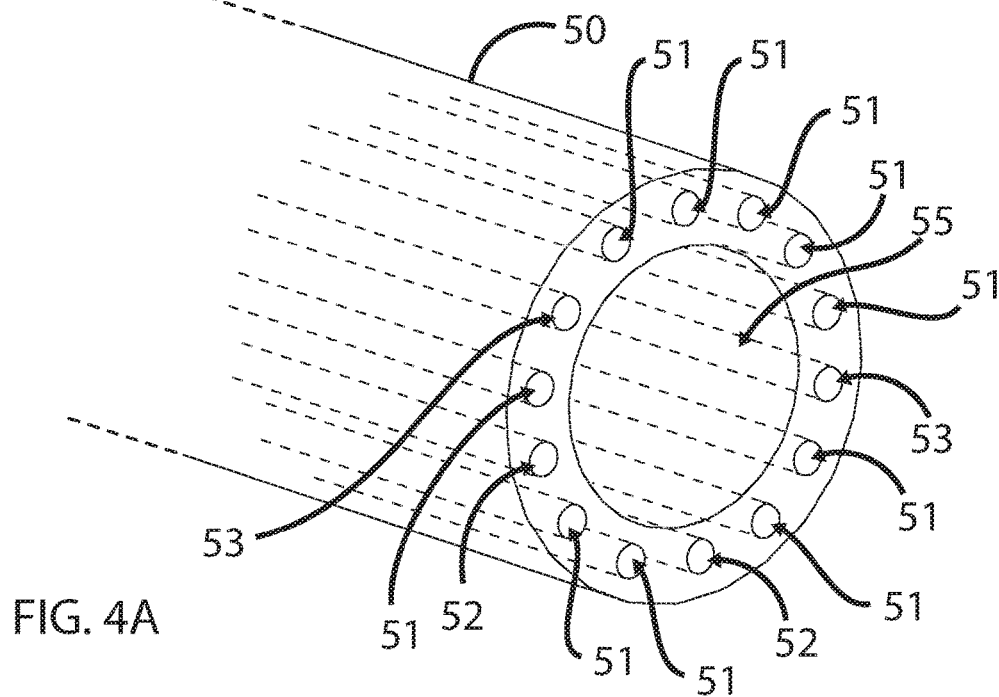
FIG. 4A is a detailed view of the core in the FIG. 3 embodiment.

FIG. 4A is a detailed view of the core 50 from the FIG. 3 embodiment. The core 50 has a distal end and a main channel 55 that runs through the core in a proximal-to-distal direction, and is centered about the radial center of the core 50. The core 50 also has at least four first channels 51 that run through the core in a proximal-to-distal direction, and each of the first channels 51 is dimensioned to accommodate a respective one of the pull wires 76. Preferably, each of the first channels 51 is a lumen. In some embodiments, the walls of these lumens 51 are made from the same material as the core 50. In alternative embodiments, the walls of these lumens 51 are lined with a smooth material such as PTFE.

The core 50 also has at least one second channel 52 that runs through the core in a proximal-to-distal direction, and the at least one second channel 52 is dimensioned to accommodate the first and second proximal portions 84 of the cinching cord. Preferably, each of the proximal portions 84 of the cinching cord runs through its own individual second channel 52, and each of these second channels is dimensioned to accommodate a respective proximal portion 84 of the cinching cord. However, in less preferred embodiments, both the first and second proximal portions 84 of the cinching cord can run through a single second channel 52. Preferably, each of the second channels 52 is a lumen. In some embodiments, the walls of these lumens 52 are made from the same material as the core 50. In alternative embodiments, the walls of these lumens 52 are lined with a smooth material such as PTFE.

Preferably, each of the first channels 51 and each of the at least one second channel 52 is located at positions that are radially beyond the main channel 55. Optionally, each of the first channels 51 and each of the at least one second channel 52 is located at the same radial distance from the radial center of the core 50.

The core 50 also has a plurality of third channels 53 that run through the core in a proximal-to-distal direction, and the plurality of third channels 53 are dimensioned to accommodate the support rods 95 described below in connection with FIG. 4B. In some preferred embodiments, the diameter of each of the first channels 51, each of the second channels 52, and each of the third channels 53 is 0.45 mm.

Figure 4B:
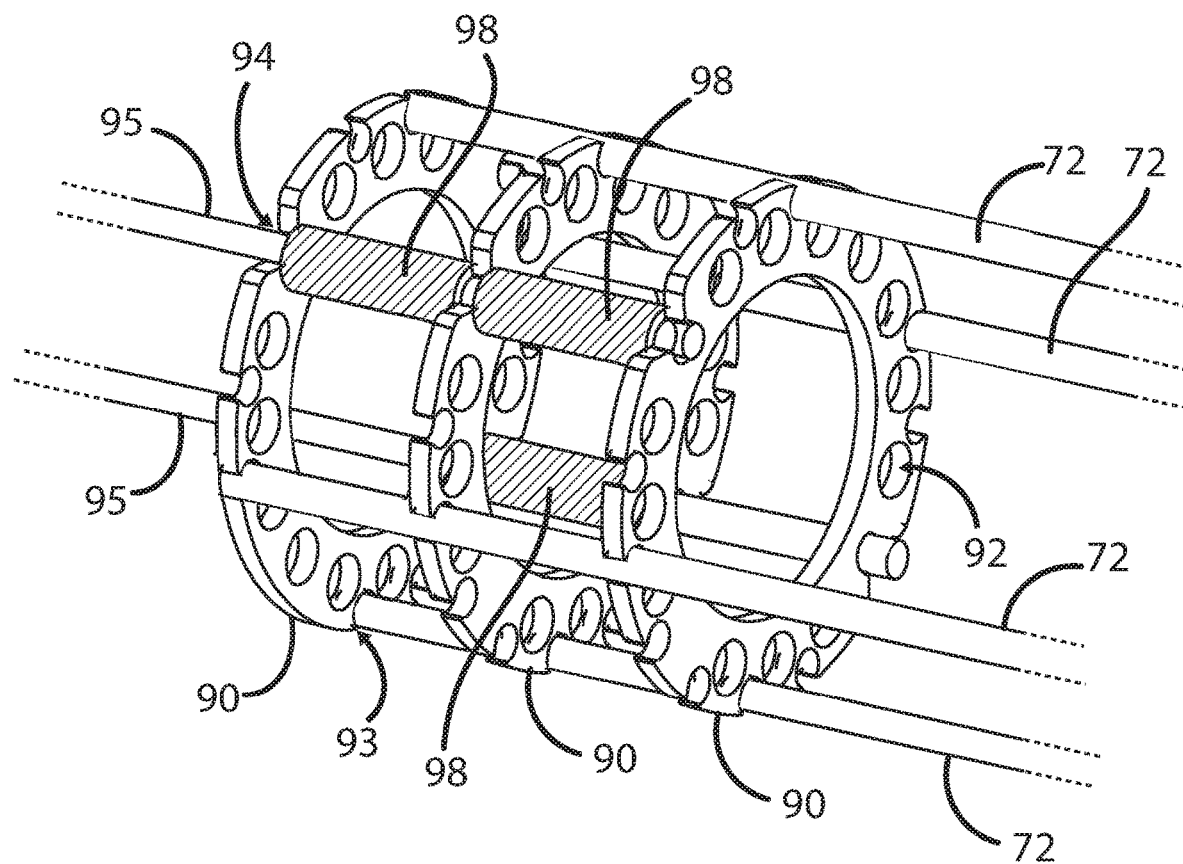
FIG. 4B depicts how the support arms are affixed to the core in the FIG. 3 embodiment.

FIG. 4B depicts one preferred approach for mounting the support arms 72 to the core 50. In this approach, the support arms 72 are affixed to a plurality of support rings 90, and the support arms extend in a distal direction from the support rings. A plurality of support rods 95 are also affixed to the support rings, and the support rods extend in a proximal direction from the support rings. These support rods 95 may be formed of metal wire. Using this subassembly (which includes the support rings 90, the support rods 95, and the support arms 72), the support arms 72 can be mounted to the core 50 by inserting the support rods 95 into the third channels 53 of the core 50, so as to yield the configuration depicted in FIG. 3.

The support rings 90 each have a plurality of holes 92, and these holes 92 are positioned so that when the support rods 95 have been inserted into the third channels 53 of the core 50, the holes 92 in the support rings will line up with the first channels 51 and the second channels 52 in the core 50. The support rings 90 also include at least four cut outs 93 dimensioned and configured to support the support arms 72 and a plurality of cut outs 94 dimensioned and configured to support the support rods 95.

Optionally, radio-opaque material (e.g. 80% platinum and 20% iridium, or other alternatives that will be apparent to persons skilled in the relevant arts) may be added to the subassembly to help ascertain the position of the apparatus during the procedure for installing the cinching cord or annulus ring using fluoroscopy. Preferably, the radio-opaque material is distributed in an asymmetric pattern. For example, a pair of radio-opaque sleeves 98 may be disposed on one of the support arms 95, and a single radio-opaque sleeve 98 may be disposed on another one of the support arms 95. Using an asymmetric distribution of radio-opaque material makes it easier to ascertain the orientation of the apparatus during the procedure for installing the cinching cord or annulus ring, because different portions of the apparatus will look different under fluoroscopy. Of course, it will be appreciated by persons skilled in the relevant art that the radio-opaque material may be distributed in a wide variety of different asymmetric patterns, and still remain useful for positioning and orientation purposes.

Returning to FIG. 3, the first and second proximal portions 84 of the cinching cord are disposed in the at least one second channel 52 and can slide easily within the at least one second channel 52. In addition, each of the at least four pull wires 76 is disposed in a respective one of the first channels 51 and can slide easily within the first channels 51.

Figure 6A:
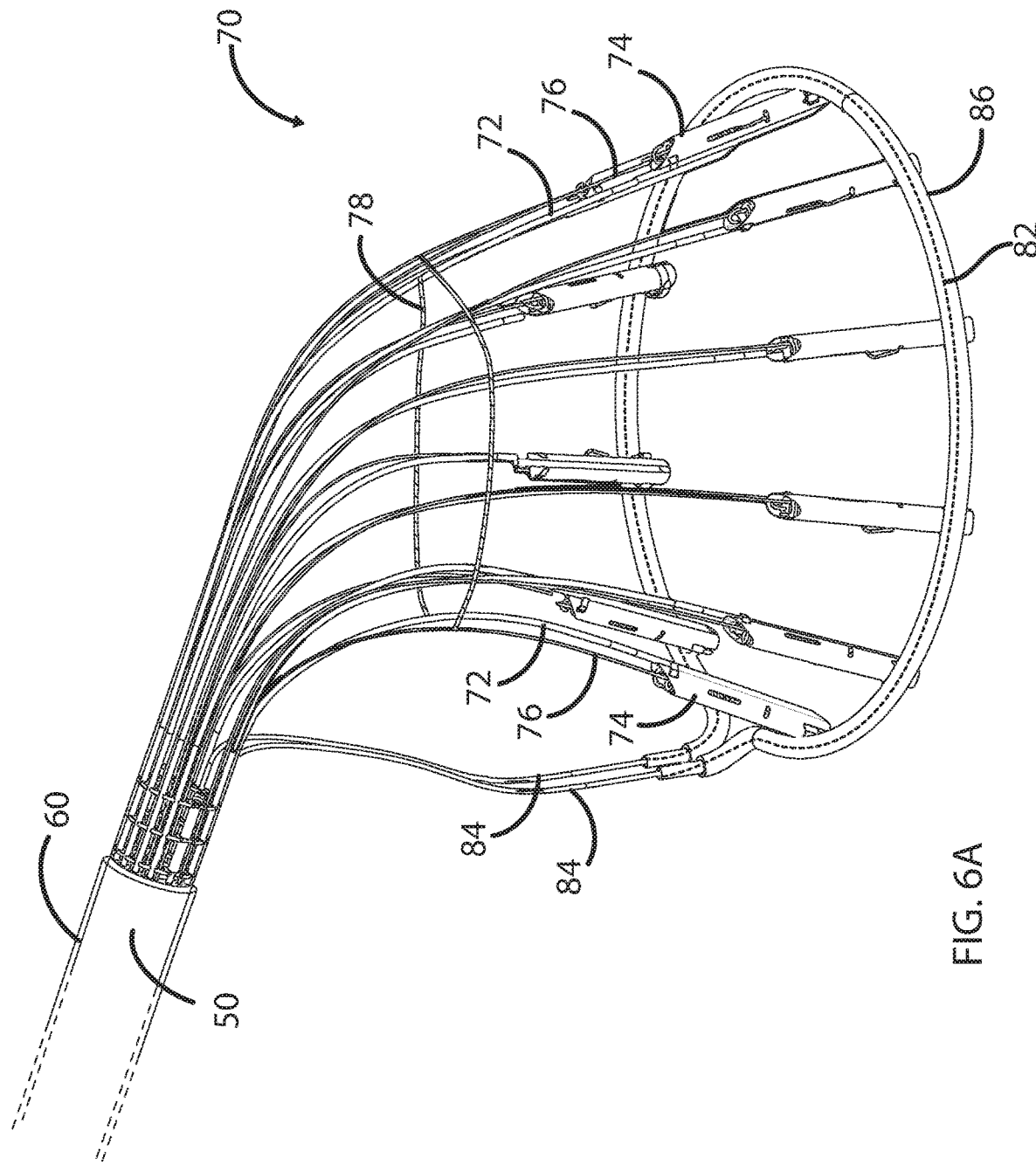
FIG. 6A is a detailed view of a distal assembly that has emerged from within the outer sleeve in the FIG. 1 embodiment.
Figure 6B:
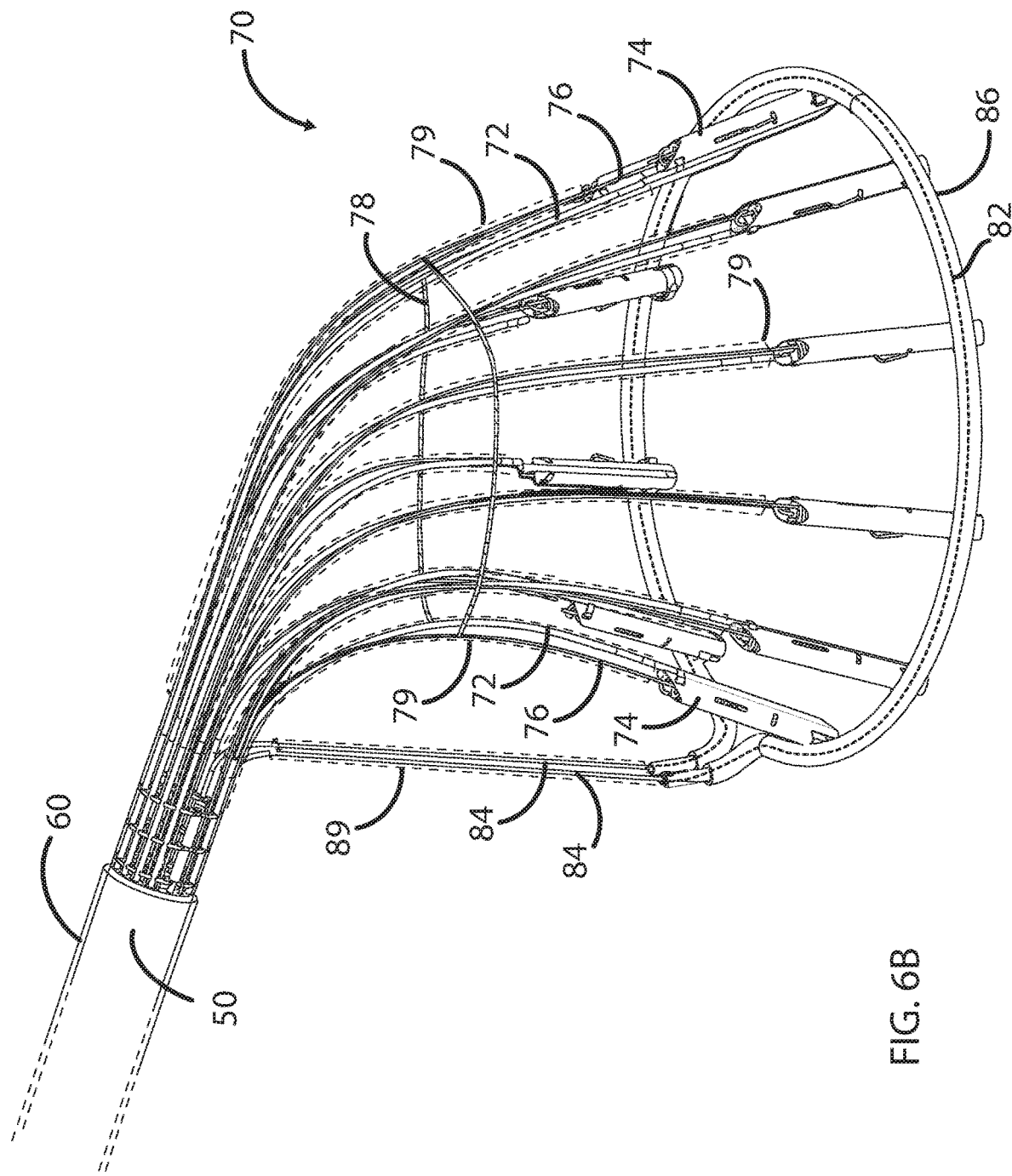
FIG. 6B depicts the FIG. 6A view with additional sleeves that cover certain components.

When the outer sleeve 60 is in the extended position (as it is in FIG. 3), the support arms 72 and the anchor launchers 74 are disposed within the outer sleeve 60. But when the outer sleeve 60 is in the retracted position, the anchor launchers 74 and at least a portion of the support arms 72 extend distally beyond the distal end of the outer sleeve 60 (as best seen in FIGS. 6A and 6B).

Figure 5A:
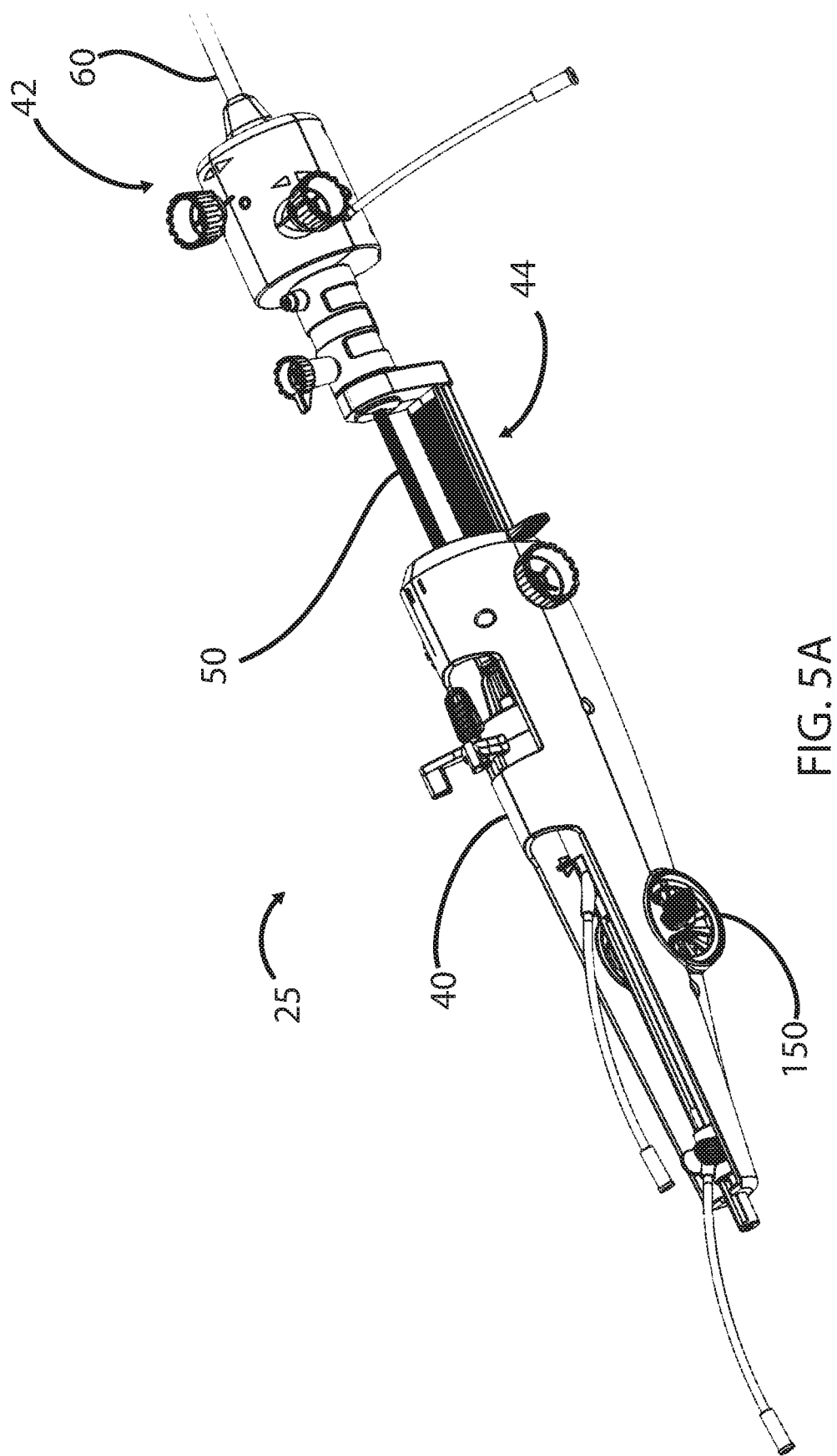
FIGS. 5A, 5B, and 5C depict respective views of the portion of the FIG. 1 embodiment that moves the outer sleeve between the extended position and the retracted position.
Figure 5B:
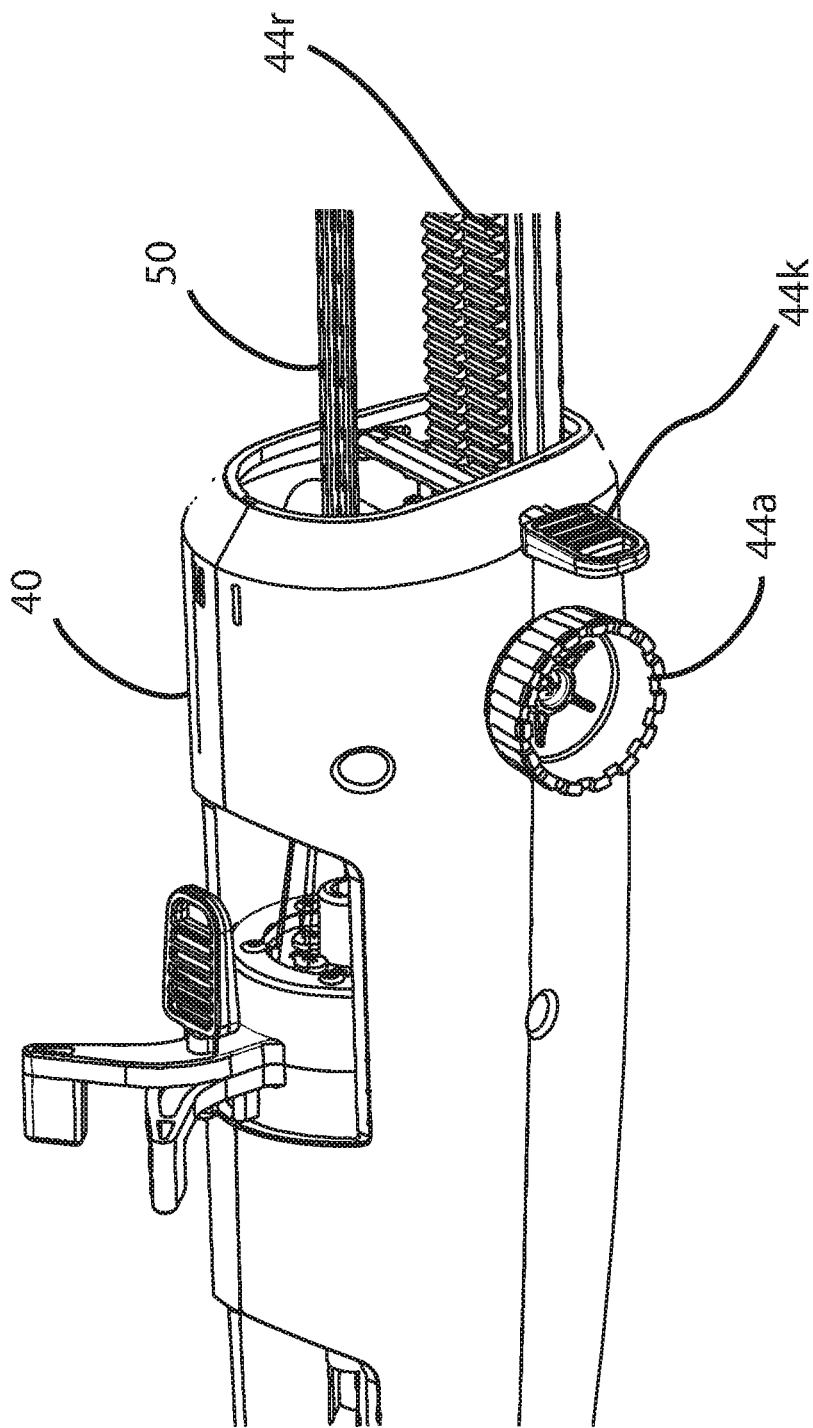
Figure 5C:
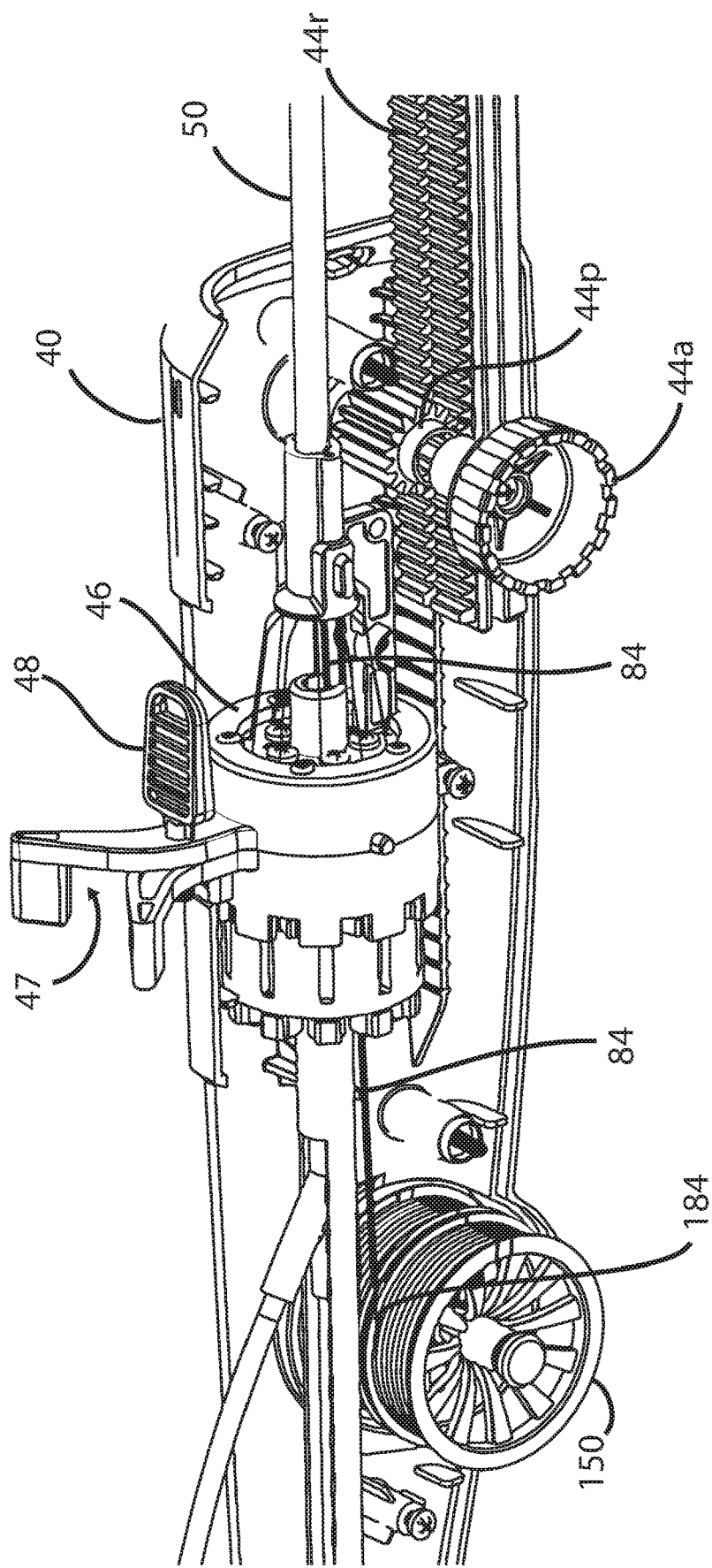

FIGS. 5A-C depict the portion of the apparatus 25 that moves the outer sleeve 60 between the extended position (as depicted in FIGS. 1 and 3) and the retracted position (as depicted in FIGS. 2 and 6). Components with similar numbers correspond to the same components discussed above in connection with FIGS. 1-4.

The apparatus 25 includes a housing 40 that is sized to be held in a person's hand and it has a plurality of controls 44a, 47 that are used to operate the apparatus 25. The housing may be formed of thermoplastic, metal, or any other suitable material. The elongated core 50 is mounted in a fixed spatial relationship with respect to the housing 40, and the mounting of the core 50 to the housing 40 may be implemented either directly or via intermediate components. The outer sleeve 60 (shown in FIGS. 3 and 5A) is disposed around the core 50 and the outer sleeve 60 is slidable with respect to the core 50 between an extended position and a retracted position.

In the illustrated embodiment, the sleeve retractor 44 is responsible for moving the outer sleeve 60 with respect to the core 50. This is accomplished using a rack-and-pinion that includes rack 44r and pinion 44p. A steering control assembly 42 (that preferably facilitates medial and anterior deflecting of the catheter shaft and also rotation with respect to the housing 40) is affixed to the distal end of the rack 44r, and the outer sleeve 60 is affixed to the distal end of the steering control assembly 42. As a result, the outer sleeve 60 will track the movements of the rack 44r. Clockwise rotation of the actuator 44a will cause the pinion 44p to rotate in a clockwise direction, which will cause the rack 44r to move in a proximal direction with respect to the housing 40. Preferably, a locking pin 44k prevents the rack 44r from moving when the locking pin 44k is inserted, which prevents unintentional retraction of the outer sleeve 60 during insertion of the apparatus.

Because of the core 50 is in a fixed spatial relationship with respect to the housing, movement of the rack 44r in the proximal direction will cause the outer sleeve 60 to slide in a proximal direction with respect to the core 50. This will cause the outer sleeve 60 to move from the extended position (shown in FIGS. 1 and 3) to the retracted position shown in FIGS. 2 and 6A.

FIG. 6A is a detailed view of a distal assembly 70 that has emerged from within the outer sleeve 60 as a result of the retraction of the outer sleeve 60, so that the distal assembly 70 extends distally beyond the distal end of the outer sleeve 60. The distal assembly 70 in this embodiment includes ten anchor launchers 74, each of which is supported by its own individual support arm 72. In some embodiments, the support arms 72 are mounted to the core 50 as described above in connection with FIGS. 3-4. The support arms are shaped such that when the outer sleeve 60 is in the retracted position, the support arms 72 hold the distal ends of the anchor launchers 74 at positions that correspond to a shape of the annulus, with the distal ends of the anchor launchers 74 distributed about a perimeter of the shape of the annulus (see also FIG. 7C).

Note that the shape of the distal loop portion 82 of the cinching cord in FIG. 6A is round, and this shape is suitable when the cinching cord is installed onto a round annulus. In alternative embodiments, when the cinching cord is installed onto an annulus with a different shape (e.g., a mitral valve annulus that is D-shaped), the support arms 72 are preshaped so that the distal ends of the anchor launchers 74 will be distributed about the perimeter of that differently-shaped annulus.

Preferably, the shape and size of the support arms 72 are designed to fit the anatomy of the individual patient, so that when the outer sleeve 60 is retracted, the distal loop portion 82 of the cinching cord will be opened by the support arms 72 and spread around the annulus, so that it will be in the correct location ready for the anchors to be launched with little adjustment. This may be achieved, e.g., by designing the 3D shape of the support arms 72 so that they each extend in a predefined angulation from the core 50.

The desired shape of the support arms 72 and the circumference of the distal loop portion 82 of the cinching cord may be determined by converting a CT scan of the patient into a 3D CAD file. The support arms 72 can then be formed so that they will hold the distal loop portion 82 of the cinching cord in a configuration that matches the target annulus. One preferred approach for accomplishing this is to insert the anchor launchers 74 into a jig that holds the distal ends of the anchor launchers 74 at positions that match the annulus in the CAD file. An assembly that includes the support rings 90, the support rods 95 and the support arms 72 is then attached to the anchor launchers 74 (e.g. using welding or an appropriate adhesive). The jig will also hold the support rods 95 at a position that provides an appropriate angle between the support rods 95 and the support arms 72. The assembly (with the anchor launchers 74 attached) is then heated to take on the shape that is being forced upon it by the jig. Optionally, the support arms may be made of a shape-memory material e.g. nitinol.

A cinching cord has a distal loop portion 82, a first proximal portion 84, and a second proximal portion 84. The distal loop portion 82 of the cinching cord is preferably surrounded by a sleeve 86 of material that promotes tissue ingrowth such as a fabric braid. As explained above, the anchors that are disposed within the anchor launchers 74 are connected to the distal loop portion 82 of the cinching cord, and the anchor launchers 74 are configured so that pulling on a respective pull wire 76 will launch the respective anchor.

FIG. 6B is similar to FIG. 6A (and similar reference numbers correspond to similar features), except that FIG. 6B also shows a set of sleeves 79, 89 that were omitted from FIG. 6A for clarity. Each of the anchor launchers 74 is supported by one of the support arms 72 and is actuated by one of the pull wires 76. To facilitate smoother opening of the support arms 72 into the configuration depicted in FIG. 6B, it is preferable to surround the support arm 72 and the pull wire 76 that terminate at each individual anchor launcher 74 in a sleeve 79. In the FIG. 6B embodiment, there will be one sleeve 79 for each of the anchor launchers 74, and the support arms 72 and the pull wires 76 for that anchor launchers 74 will run through the center of the corresponding sleeve 79. In some embodiments, these sleeves 79 are made from clear shrink tubing with an inner diameter (after shrinking) that is large enough so as not to interfere with the slidability of the pull wires 76 within the sleeves 79. In alternative embodiments, the sleeves 79 may be made from other polymer materials with a similar inner diameter.

Preferably, an additional sleeve 89 is provided, and the proximal portions 84 of the cinching cord run through this additional sleeve 89. The sleeve 89 is similar to the sleeve 79 discussed above, and is dimensioned to have an inner diameter that is large enough so as not to interfere with the slidability of the proximal portions 84 of the cinching cord within the sleeve 89.

Figure 7A:
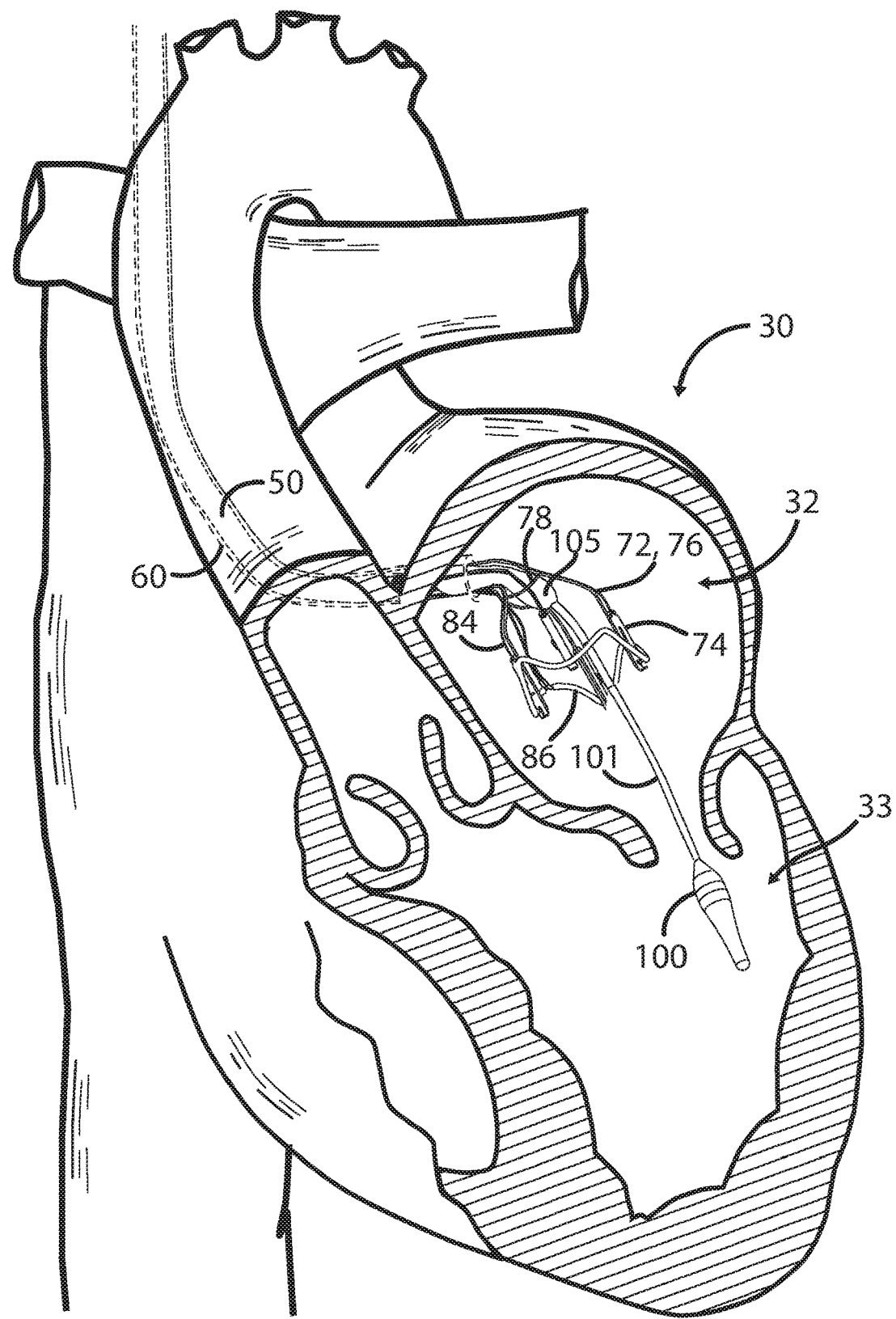
FIG. 7A depicts the FIG. 3 apparatus after the distal end of the apparatus has been inserted into the left atrium and the outer sleeve has been partially retracted.
Figure 7B:
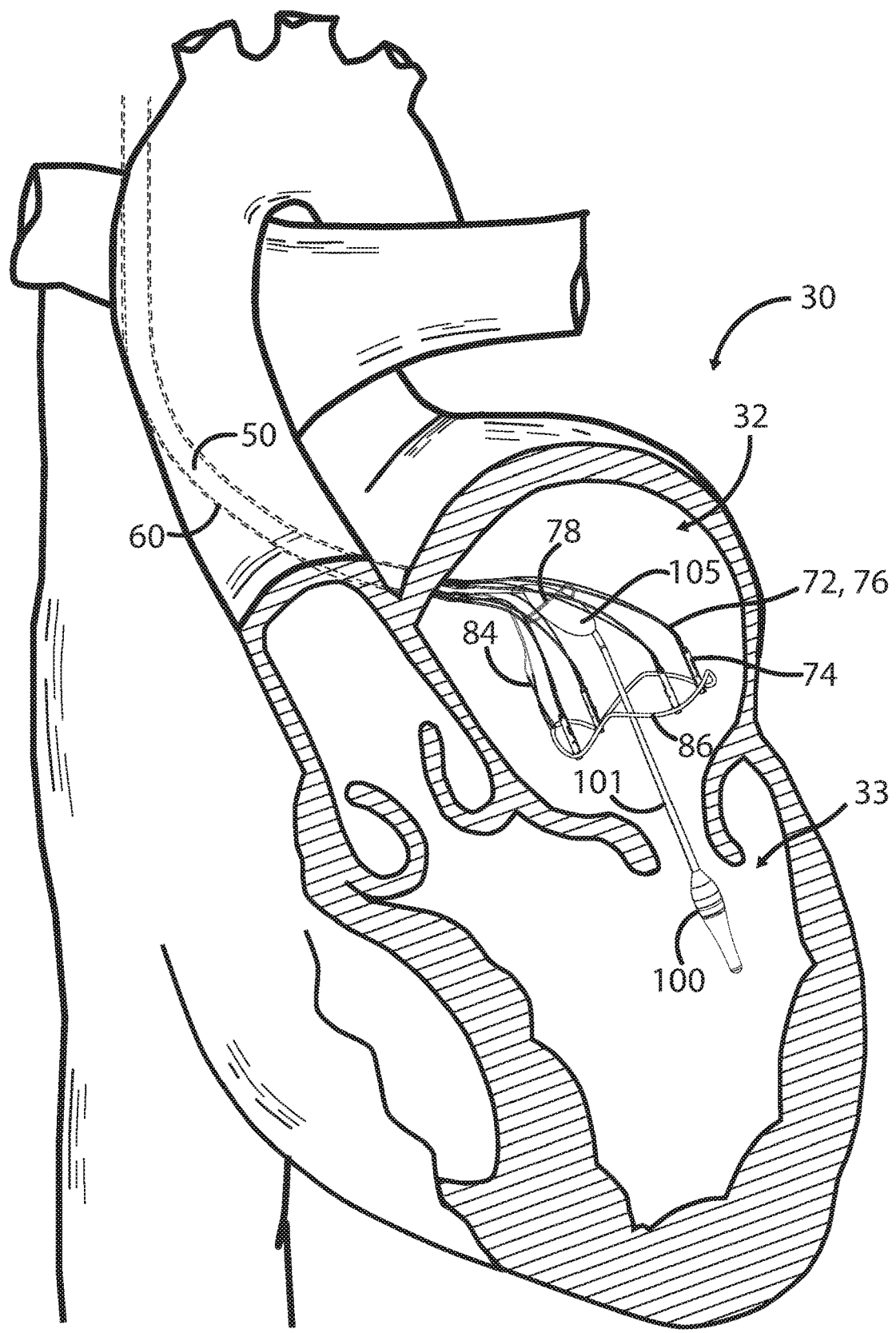
FIG. 7B depicts the FIG. 3 apparatus after the outer sleeve has been fully retracted.
Figure 7C:
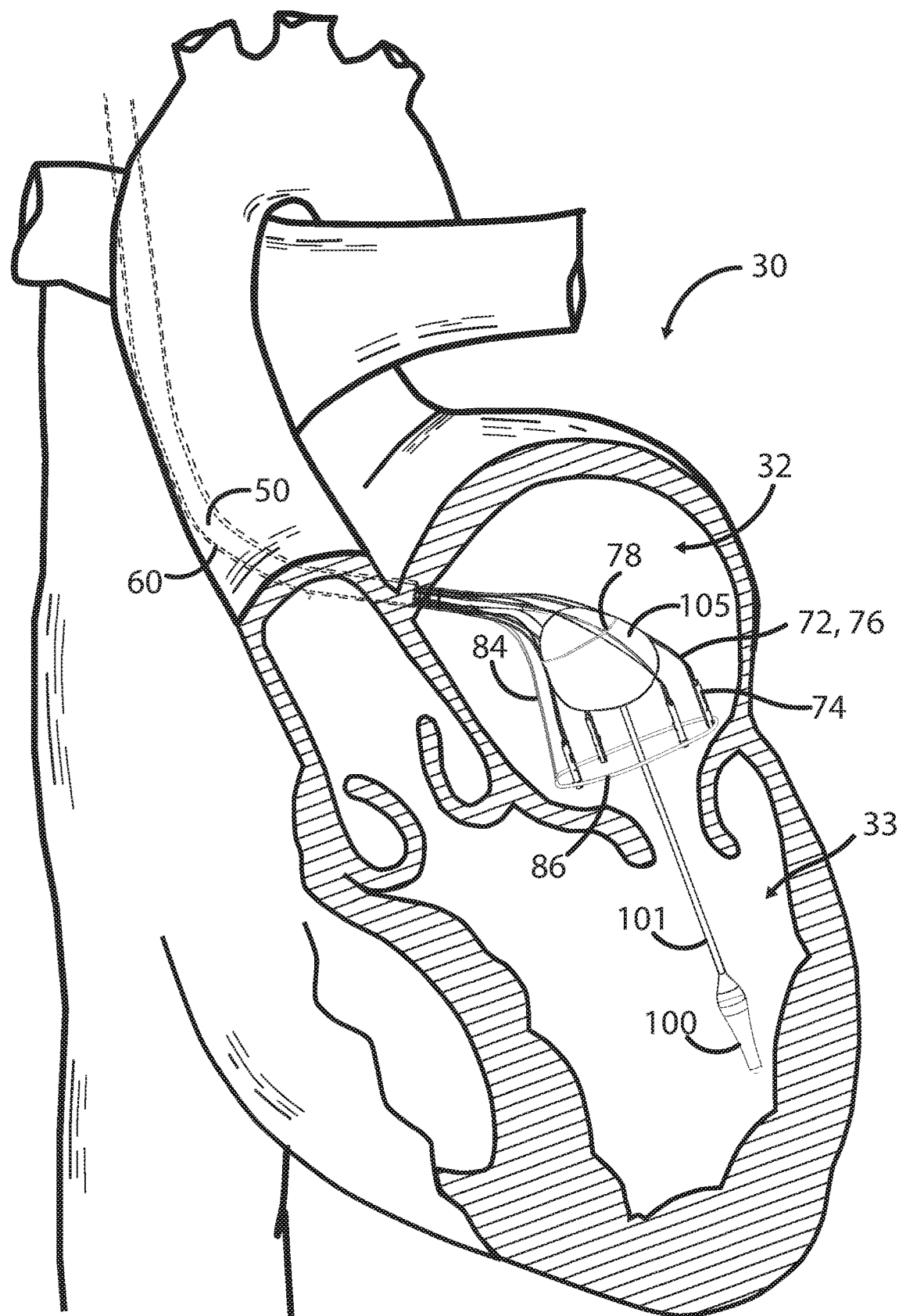
FIG. 7C depicts the FIG. 3 apparatus after the balloon has been inflated.
Figure 7D:
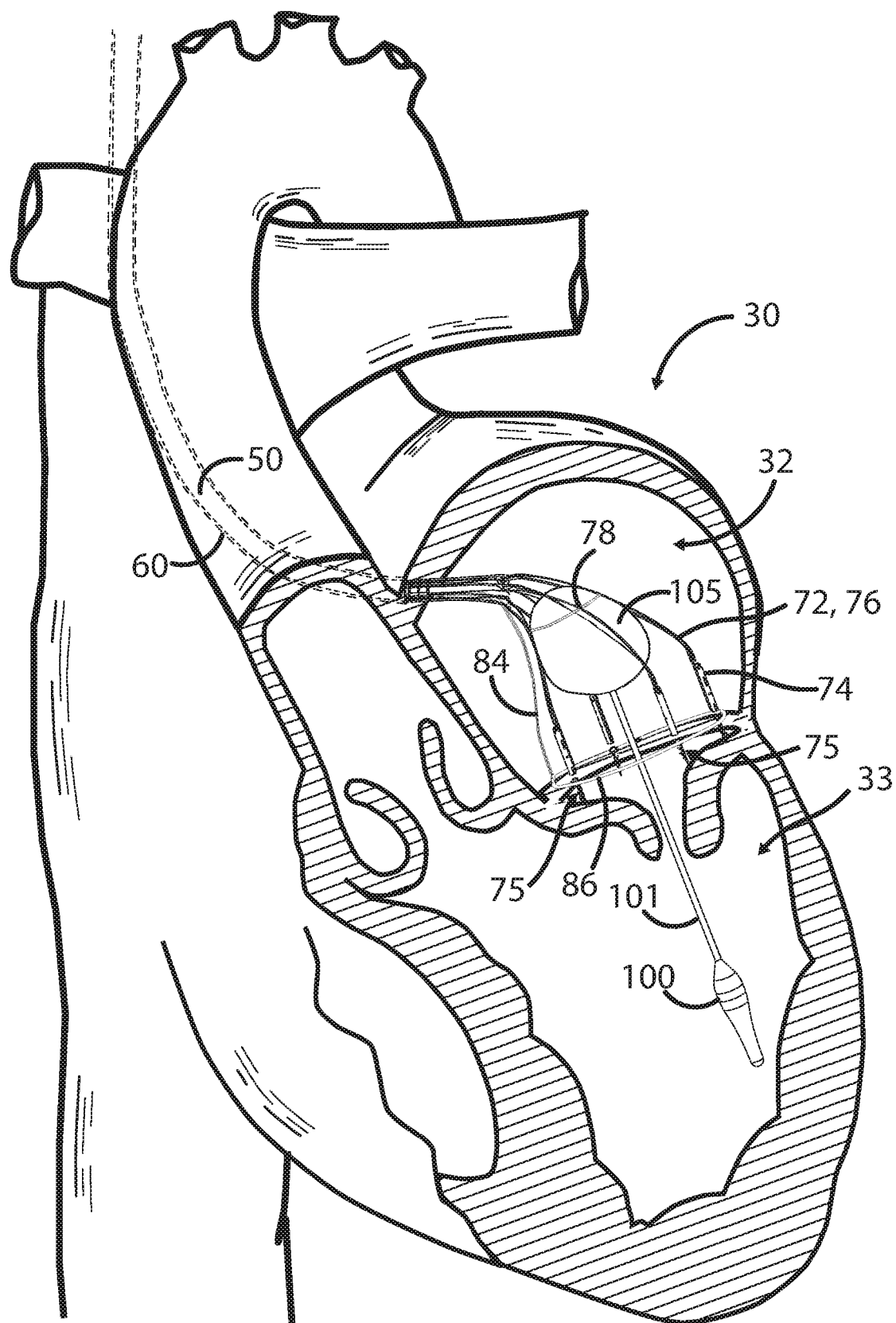
FIG. 7D depicts the FIG. 3 apparatus immediately after the anchors have been launched into the annulus.

In some embodiments, a retainer cord 78 is connected to the support arms 72 and arranged with respect to the support arms 72 so that when the balloon 105 is disposed on a between the support arms 72 and inflated (as seen in FIG. 7D), the retainer cord 78 will encompass the balloon 105 and prevent the balloon 105 from slipping out between the support arms 72.

The retainer cord 78 may be connected to the support arms 72 using at least one knot. In some embodiments, the retainer cord 78 comprises a silk suture. In alternative embodiments, the retainer cord 78 comprises a polymer (e.g., nylon, polypropylene, polyester, etc.) cord.

In some preferred embodiments, the support arms 72 are enclosed in sleeves 79 as described above, and the retainer cord 78 is connected to the support arms 72 by threading the retainer cord 78 through a hole in each of the sleeves 79 and tying a knot at each of the sleeves 79. This may be accomplished, for example, using a continuous surgical silk suture or a polymer cord that is connected between each of the support arms 72 and its adjacent neighbor in sequence. The retainer cord 78 may be attached to the support arms 72 by having an assembler puncture each sleeve 79 with the integral needle of a surgical suture that will ultimately serve as the retainer cord 78. After making the puncture, the retainer cord 78 is passed through the puncture and is fastened to the sleeve 79 using a knot (such as an overhand knot). The assembler then continues to the next support arm 72 and sleeve 79 and repeats the same process, eventually returning to the first support arm 72 and sleeve 79. When this process is used to connect the retainer cord 78 to the support arms 72, it is preferable to ensure that none of the knots enclose any of the pull wires (so as not to interfere with the pull ability of the pull wires).

In alternative embodiments (not shown), the single retainer cord 78 that is attached to each of the support arms 72 may be replaced with two or more shorter segments of retainer cord, such that the shorter segments of retainer cord, collectively taken together, encompass the balloon and prevent the balloon from slipping out between the support arms.

FIGS. 7A-D depict using the FIG. 1-6 embodiments described above to install a cinching cord onto the mitral valve annulus of a human subject, at sequential stages in time. In this example, the distal end of the apparatus 25 is routed through the subject's jugular and superior vena cava into the right atrium of the subject's heart 30 with the outer sleeve 60 in its extended position (as shown in FIG. 1). The distal tip is then passed through a puncture in the septum using any conventional approach and into the subject's left atrium 32.

FIG. 7A depicts the apparatus after the distal end of the apparatus has reached the left atrium 32, and the outer sleeve 60 has been partially retracted. The anchor launchers 74 and the distal loop portion 82 of the cinching cord (which is disposed inside the sleeve 86) extend distally beyond the distal end of the outer sleeve 60. The nosecone 100 mounted on the shaft 101 is lowered into the left ventricle 33 of the subject's heart. Note that at this point in the sequence, only a portion of the support arms 72 extend distally beyond the distal end of the outer sleeve 60, and the distal loop portion of the cinching cord (within sleeve 86) remains partially collapsed.

FIG. 7B depicts the same apparatus after the outer sleeve 60 has been fully retracted. Now, the anchor launchers 74, the distal loop portion of the cinching cord (which is disposed inside the sleeve 86), the support arms 72, the ends of the pull wires 76, the balloon 105, and the balloon retainer 78 all extend distally beyond the distal end of the outer sleeve 60. At this point, spring action of the support arms 72 has opened up the distal loop portion of the cinching cord (within sleeve 86) significantly.

FIG. 7C depicts the same apparatus after the balloon 105 has been inflated. The balloon retainer 78 prevents the balloon 105 from slipping out between the support arms 72. The anchor launchers 74, the distal loop portion of the cinching cord (within the sleeve 86), the support arms 72, the ends of the pull wires 76, the balloon 105, and the balloon retainer 78 all remain distally beyond the distal end of the outer sleeve 60. At this point, the balloon 105 has pushed the support arms away from each other, to help move the support arms 72 into a position where they hold the distal ends of the anchor launchers 74 at positions that correspond to a shape of the annulus, with the distal ends of the anchor launchers 74 distributed about a perimeter of the shape of the annulus. Preferably, the support arms 72 have been preformed (as described above in connection with FIG. 6A) so that none of the anchor launchers 74 will be positioned on or adjacent to the AV node to prevent potential damage to that node.

The distal ends of the anchor launchers 74 are pressed against the annulus and, after proper positioning has been confirmed (e.g. using fluoroscopy), the anchor launchers 74 are triggered by pulling on the proximal ends of the pull wires 76. This causes each of the anchor launchers 74 to launch its anchor into the annulus. Preferably, all of the anchors launchers 74 are triggered simultaneously. This is preferable because before anchors are launched, the structural shape of the support arms 72 determines the location and shape of the distal loop portion 82 of the cinching cord around the annulus. (In contrast, once the distal loop portion 82 is disconnected from the support arms 72, it can be very difficult to control the shape of the implant. As a result, in alternative embodiments in which the anchors are launched sequentially instead of simultaneously, the position of each anchor launcher 74 might require adjustment prior to launching, which can be very challenging.)

FIG. 7D depicts the same apparatus immediately after the anchors 75 have been launched into the annulus. At this point in the sequence, the anchors 75 have been deployed, and they hold the distal loop portion 82 of the cinching cord (within the sleeve 86) to the annulus. The proximal portions 84 of the cinching cord remain connected to the distal loop portion of the cinching cord, but the delivery system (e.g. the support arms 72, the anchor launchers 74, etc.) are no longer connected to the distal loop portion 82 of the cinching cord.

Figure 8A:
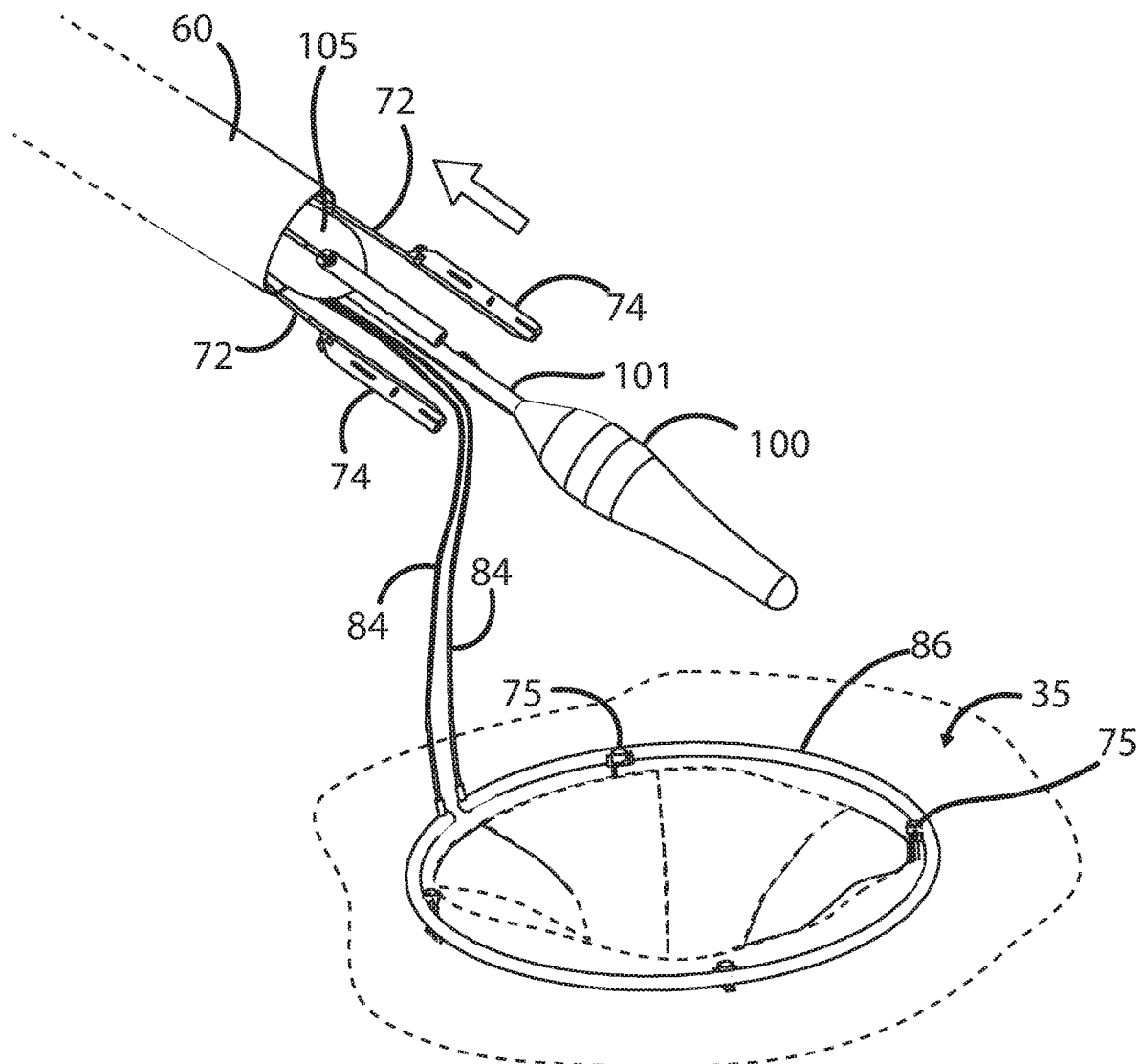
FIG. 8A depicts the FIG. 3 apparatus after the balloon is deflated and certain components have been pulled partially back into the outer sleeve.
Figure 8B:
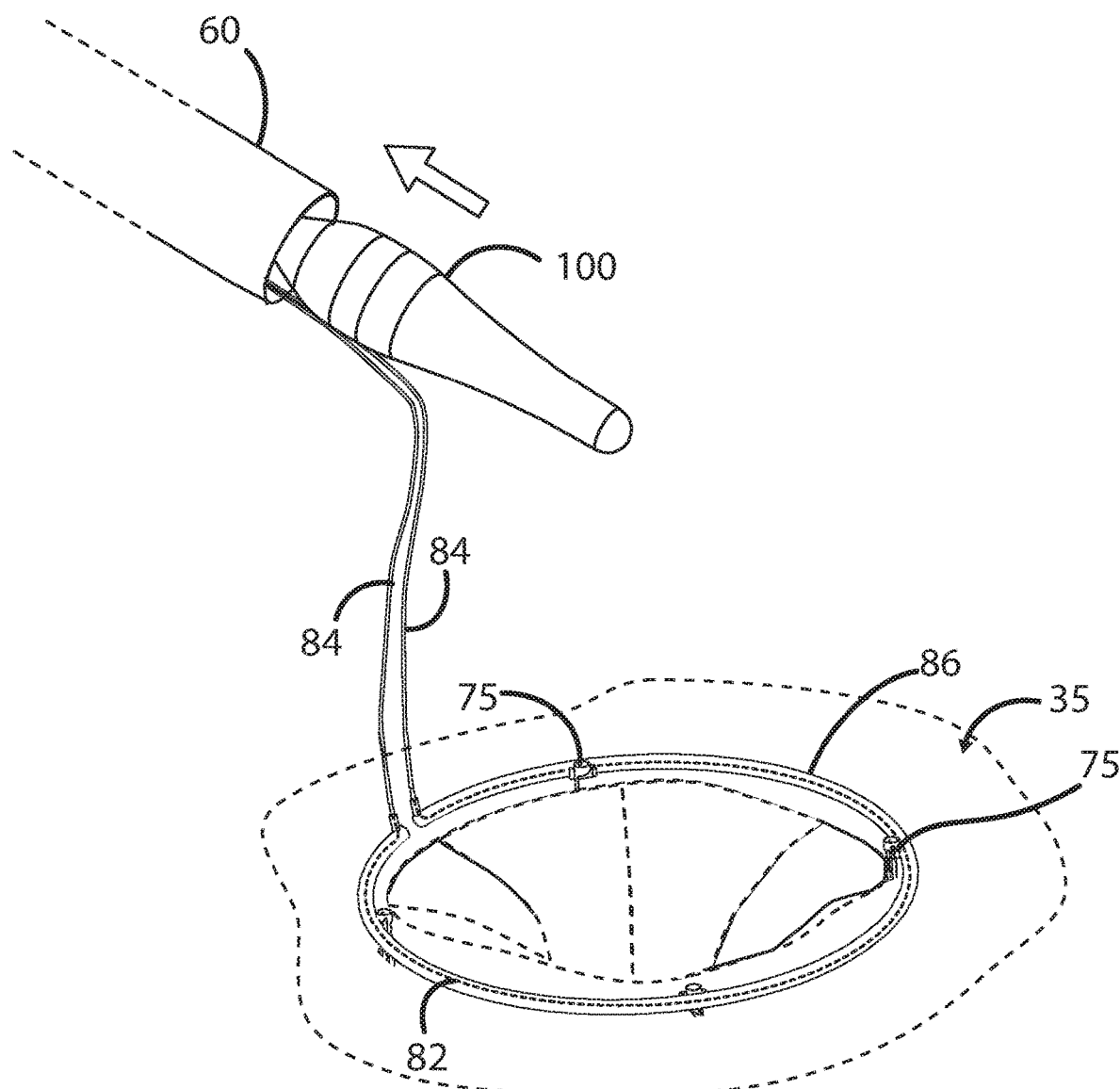
FIG. 8B depicts the FIG. 3 apparatus after those components have been pulled further back into the outer sleeve.

Next, the balloon 105 is deflated and the balloon 105, the support arms 72, and the anchor launchers 74 are pulled back into the outer sleeve 60 as shown in FIG. 8A. These components are then pulled further back into the outer sleeve 60 as shown in FIG. 8B. The anchors 75 continue to hold the distal loop portion 82 of the cinching cord (within the sleeve 86) to the annulus 35, and proximal portions 84 of the cinching cord remain connected to the distal loop portion of the cinching cord.

Figure 9A:
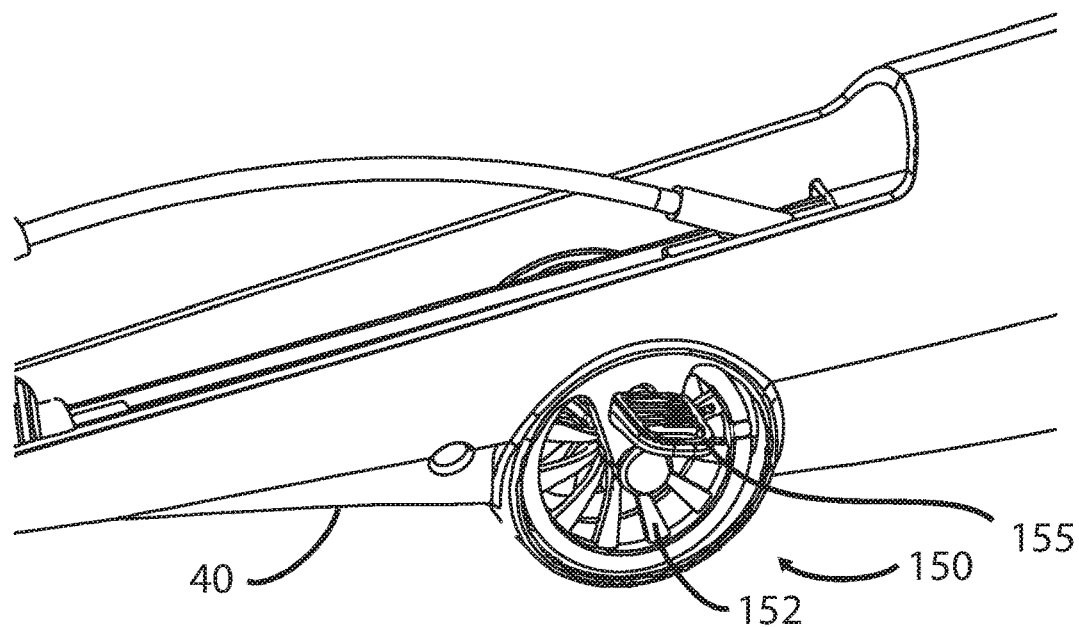
FIG. 9A is a detail of the proximal portion of FIG. 5A.

FIG. 9A is a detail of the proximal portion of the apparatus 25 shown in FIG. 5A. This detail depicts a portion of the housing 40, at least one spool 150, and a removable locking pin 155. The at least one spool 150 is rotatably mounted with respect to the housing. The locking pin 155 selectively either (a) prevents the at least one spool 150 from rotating when the pin 155 is installed or (b) allows the at least one spool 150 to rotate when the pin 155 is removed. The at least one spool is arranged with respect to the housing so that at least a portion of the at least one spool is visible from outside the housing.

In some preferred embodiments, the at least one spool has spokes 152 that enhance visibility of rotation of the at least one spool 150, and the at least one spool 150 is arranged with respect to the housing 40 so that at least a portion of the spokes 152 is visible from outside the housing 40. In alternative embodiments, the at least one spool has markings (not shown) that enhance visibility of rotation of the at least one spool 150, and the at least one spool 150 is arranged with respect to the housing 40 so that at least a portion of the markings is visible from outside the housing 40.

Figure 9B:
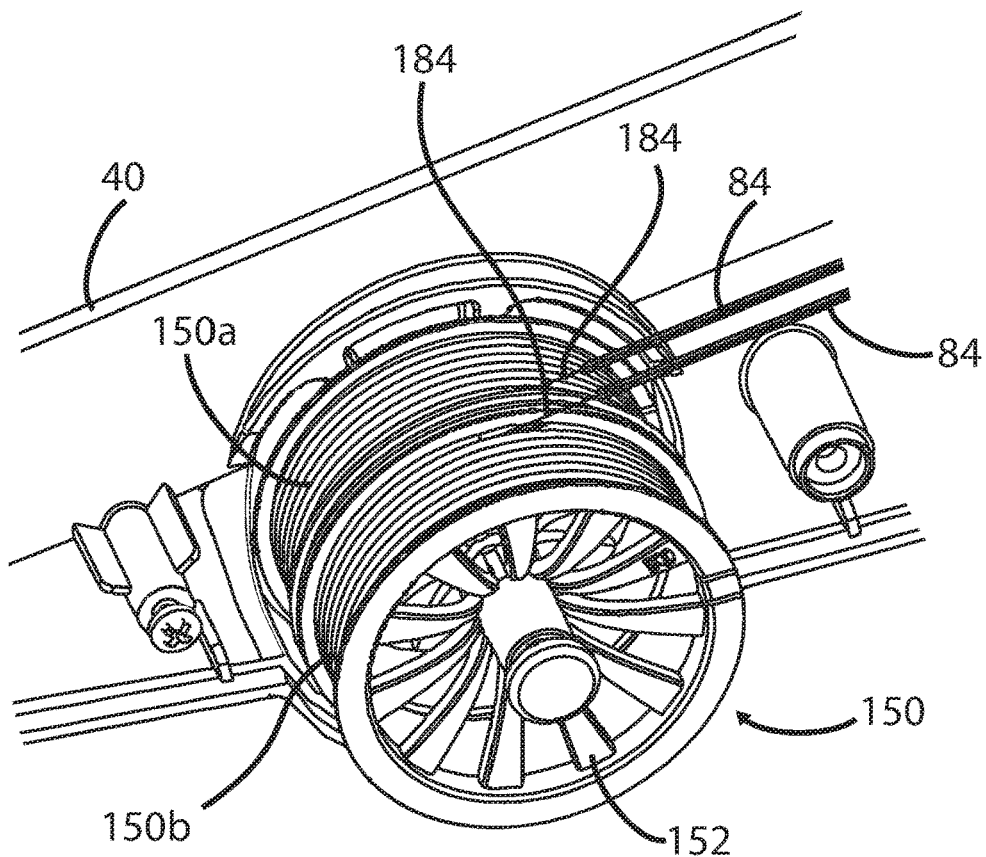
FIG. 9B is a detail cutaway view of the center portion of FIG. 9A.

FIG. 9B depicts a cutaway view of a preferred embodiment in which the at least one spool 150 comprises a single spool having (a) a first region 150a upon which the proximal section of a first extension section of cord 184 is wound and (b) a second region 150b upon which the proximal section of a second extension section of cord is wound. The first region 150a and the second region 150b are non-overlapping. In alternative embodiments, two independent spools (not shown) may be used in place of a single spool that includes two regions 150a and 150b.

The first and second extension sections of cord 184 each has a distal end and a proximal section, and the distal end of these extension sections is connected to the first and second proximal portions 84 of the cinching cord. The proximal sections of the first and second extension sections or cord 184 are wound on the at least one spool 150.

Preferably, the entire cinching cord (including the distal loop portion 82 and both proximal portions 84 of the cinching cord), the first extension section of cord 184, and the second extension section of cord 184 are contiguous sections of a single high tensile strength cord. In some preferred embodiments, this single cord is a Dyneema cord. In some preferred embodiments, this single cord is an ultra-high molecular weight polyethylene cord. In alternative embodiments, the extension sections of cord 184 are not contiguous with the cinching cord. Instead, in these embodiments, the distal end of the first extension section of cord 184 is fastened to the first proximal portion 84 of the cinching cord, and the distal end of the second extension section of cord 184 is fastened to the second proximal portion 84 of the cinching cord (e.g. using a suitable adhesive).

The cinching cord has a distal loop portion 82 (shown in FIG. 8B), and first and second proximal portions 84 (shown in FIG. 8B). The first and second proximal portions 84 of the cinching cord extend distally beyond the distal end of the core 50, and run through lumens 52 in the core 50 (shown in FIG. 4A). The first and second proximal portions 84 of the cinching cord also extend proximally beyond the proximal end of the core (shown in FIG. 5C). The lumens 52 are dimensioned to slidably accommodate the first and second proximal portions 84 of the cinching cord and also the first and second extension sections 184 of cord.

The cinching cord 82, 84, the first and second extension sections 184 of cord, the lumens 52, and the at least one spool 150 are configured so that after the distal loop portion 82 of the cinching cord is anchored to the annulus or into the tissue adjacent to the annulus by the at least four anchors 75 (shown in FIG. 8B) and the locking pin 155 (shown in FIG. 9A) has been removed, progressive movement of the housing 40 in a proximal direction will (a) cause the core 50 to progressively move in a proximal direction with respect to the first and second proximal portions 84 of the cinching cord and (b) cause the first and second extension sections 184 of cord to progressively unwind from the at least one spool and be progressively drawn into the lumens 52, respectively.

Preferably, the first and second proximal portions 84 of the cinching cord and the first and second extension sections 184 of cord pass through the lumens 52 with very low friction so that when the housing 40 is moved in the proximal direction, the anchors that hold the distal loop portion 82 of the cinching cord to the annulus will not be dislodged. Lumens 52 that have smooth polymer walls (e.g. polyethylene, polyurethane, pebax, etc.) are suitable for this purpose.

Movement of the housing 40 in the proximal direction continues, and the extension section of cord 184 will continue to unwind from the at least one spool 150 until the entire apparatus 25 (shown in FIG. 1) has been removed. At this point, the distal loop portion 82 of the cinching cord remains attached to the annulus (as shown in FIG. 8B), and the proximal portions 84 of the cinching cord run from the annulus back through the patient's vasculature to an exit point (e.g. via the superior vena cava and the jugular vein).

The preferred embodiments rely on tissue ingrowth to strengthen the bond between the distal loop portion 82 of the cinching cord and the annulus. In the FIG. 8B embodiment, the distal loop portion 82 of the cinching cord is attached to the annulus by anchoring the sleeve 86 (through which the distal loop portion 82 runs) to the annulus using the anchors 75. Preferably, the sleeve 86 is made of a material that promotes tissue ingrowth (e.g., a fabric braid). Immediately after implantation, the bond between the distal loop portion 82 the annulus is typically not strong enough to withstand cinching. But because the sleeve 86 is made of material that accepts tissue ingrowth, ingrowth of tissue at the annulus into the sleeve 86 will begin to occur after implantation. This tissue ingrowth will eventually (e.g. over the course of 2-12 weeks) strengthen the bond between the sleeve 86 and the annulus until the bond is strong enough to withstand cinching.

It is preferable if the cinching cord 82, 84 has the ability to move freely when cinching is eventually implemented. One preferred approach for facilitating this freedom of movement is to line the sleeve 86 with a material that inhibits tissue ingrowth (e.g., ePTFE, polyurethane, etc.) which will ensure that the distal loop portion 82 of the cinching cord will be able to move freely within the sleeve 86 when cinching is eventually implemented.

During the time that tissue ingrowth is strengthening the bond between the sleeve 86 and the annulus (which is desirable), tissue ingrowth can also occur between the proximal portions 84 and the vasculature through which those proximal portions travel. The latter type of ingrowth is not desirable because it could interfere with the ability of the proximal portions 84 to move freely when cinching is eventually implemented. One preferred approach for preventing tissue ingrowth between the proximal portions 84 of the cinching cord and the vasculature through which those proximal portions travel is to (a) slide a cord protector over the proximal portions of the cinching cord, and (b) leave the cord protector in place between the time that the distal loop portion 82 of the cinching cord is implanted and the time that cinching eventually occurs.

Figure 10A:
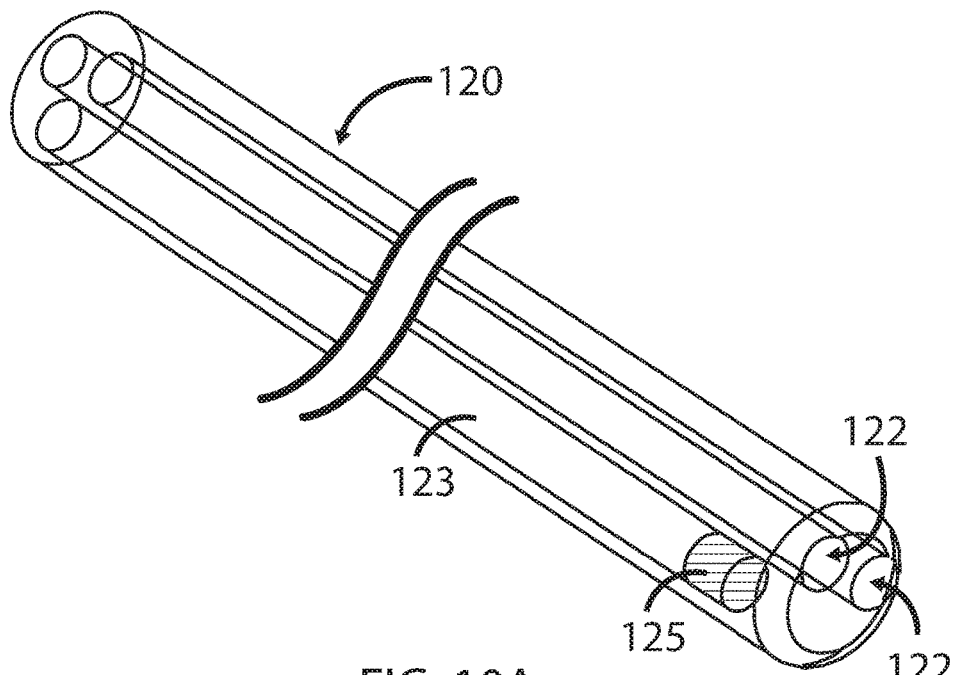
FIG. 10A depicts a cord protector for preventing tissue ingrowth

FIG. 10A depicts a suitable cord protector for this purpose. More specifically, FIG. 10A depicts a cord protector for preventing tissue ingrowth from interfering with the operation of a cinching cord that is implanted in a subject's body. The cord protector has a flexible elongated body 120 having a proximal end and a distal end. The elongated body 120 has first and second lumens 122 that run between the proximal end and the distal end of the body 120. The lumens 122 are dimensioned to slidably accommodate the proximal portions of the cinching cord. The body 120 and the lumens 122 are configured to facilitate slidable installation of the body 120 over the first and second proximal portions of the cinching cord such that the elongated body 120 covers the first and second proximal portions of the cinching cord, with the first and second proximal portions disposed in the first and second lumens 122, respectively. The body 120 prevents tissue ingrowth into the elongated body itself, and also prevents tissue ingrowth into the first and second proximal portions of the cinching cord when the elongated body 120 covers the first and second proximal portions of the cinching cord.

In some embodiments, the body 120 is formed from at least one of polyurethane and silicone. In some embodiments, the body 120 is formed from Pellethane 55D polyurethane. In some embodiments, the body 120 has a length between 35 and 65 cm and a diameter between 1 and 4 mm. In some embodiments, the body 120 has a length between 45 and 55 cm and a diameter between 1.5 and 2.5 mm. Suitable diameters for the first and second lumen 122 range between diameter between 0.2 and 1 mm.

Optionally, the body 120 may have a third lumen 123 that is open at the proximal end, closed at the distal end, and extends through at least three-fourths of the elongated body. This third lumen is dimensioned to slidably accommodate a stiffening wire, which can be useful in situations where the body 120 is insufficiently stiff to be guided to its intended destination on its own. In some embodiments, the diameter of the third lumen 123 is between 0.2 and 1 mm.

Optionally, a radio-opaque marker 125 (e.g. 80% platinum and 20% iridium, or other alternatives that will be apparent to persons skilled in the relevant arts) may be added, preferably disposed near the distal end of the elongated body. Optionally, an ePTFE capping sleeve (not shown) may be added to the cord protector.

Figure 10B:
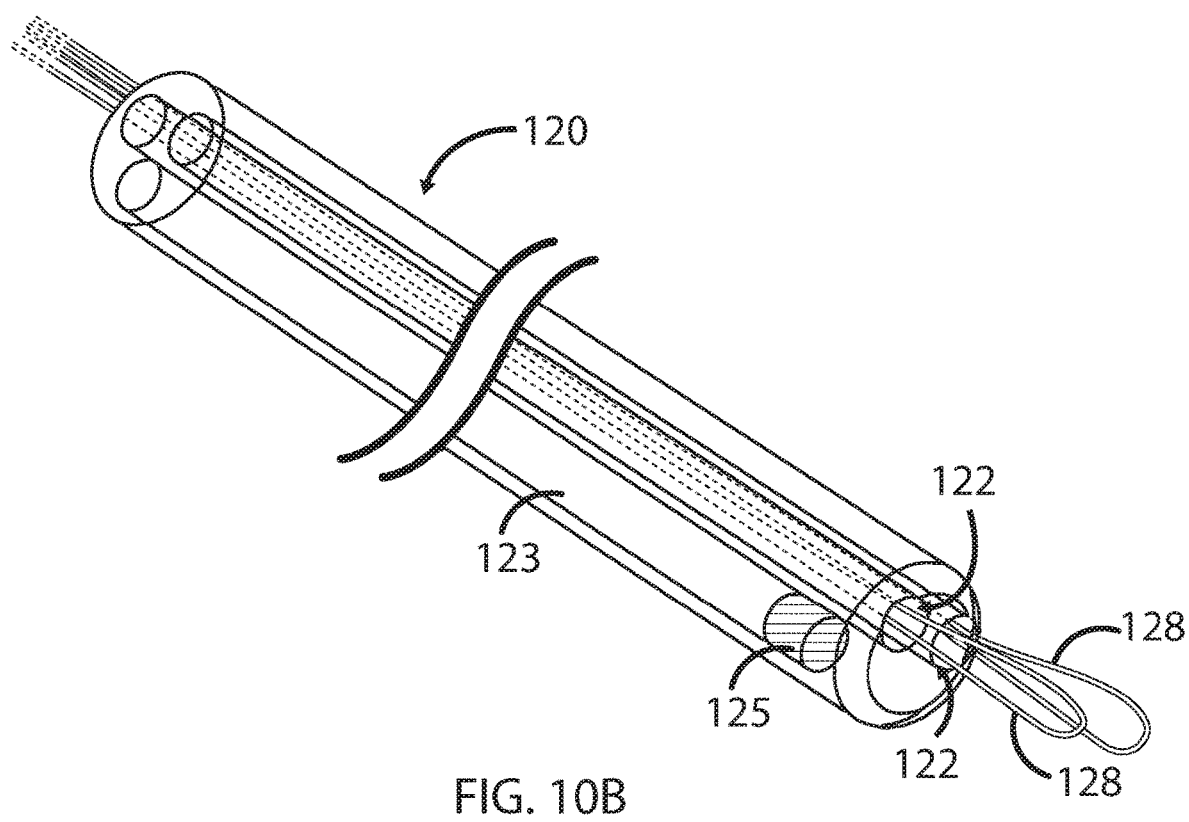
FIG. 10B depicts the cord protector of FIG. 10A combined with a set of threading cords.

FIG. 10B depicts the cord protector of FIG. 10A combined with a set of threading cords 128. The first and second threading cord 128 run through the first and second lumens and extend distally beyond the distal end of the elongated body. The first and second threading cords 128 are configured to draw the first and second proximal portions of the cinching cord into the first and second lumens 122, respectively, so that the first and second proximal portions of the cinching cord can operate as guidewires over which the elongated body 120 can be slid into a position at which the distal end of the elongated body 120 is adjacent to the distal loop portion of the cinching cord. Suitable materials for the threading cords 128 include nitinol and stainless steel. Optionally, both the cord protector and the threading cords 128 may be packaged inside a sterile envelope.

Figure 11:
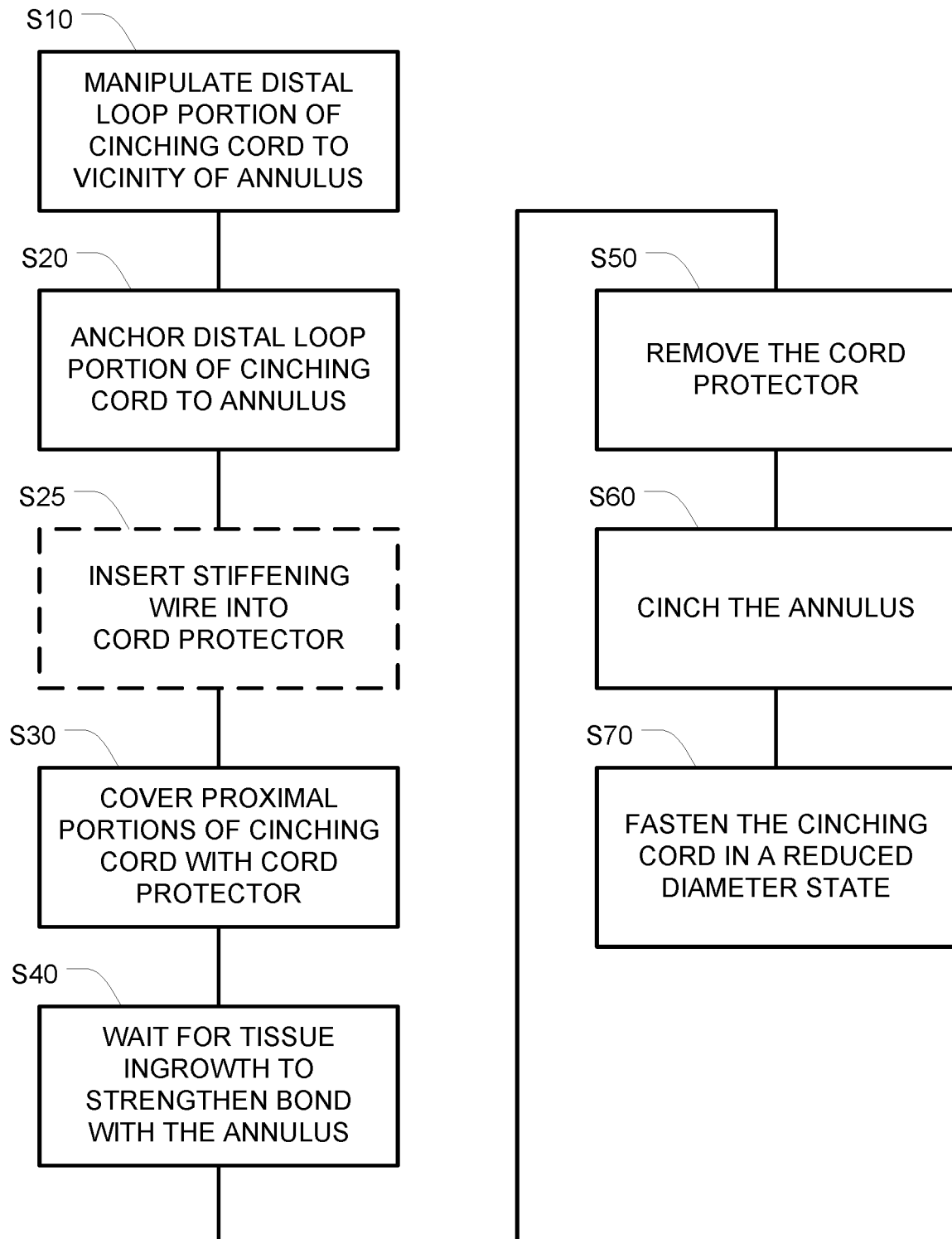
FIG. 11 is a flowchart of a method for preventing tissue ingrowth from interfering with the cinching of an annulus.

FIG. 11 depicts a method for preventing tissue ingrowth from interfering with the cinching of an annulus using a cinching cord. In step S10, the cinching cord is manipulated so that (a) a distal loop portion of the cinching cord (disposed within a sleeve) is in the vicinity of the annulus and (b) the first and second proximal portions of the cinching cord run in a proximal direction from the distal loop portion of the cinching cord back through the vasculature of the subject (as depicted in FIG. 7C). In step S20, the distal loop portion of the cinching cord is anchored to at least one of the annulus and tissue adjacent to the annulus. This step is preferably implemented by anchoring the sleeve to at least one of the annulus and the tissue adjacent to the annulus using a plurality of anchors (as depicted in FIG. 8B).

Figure 12A:
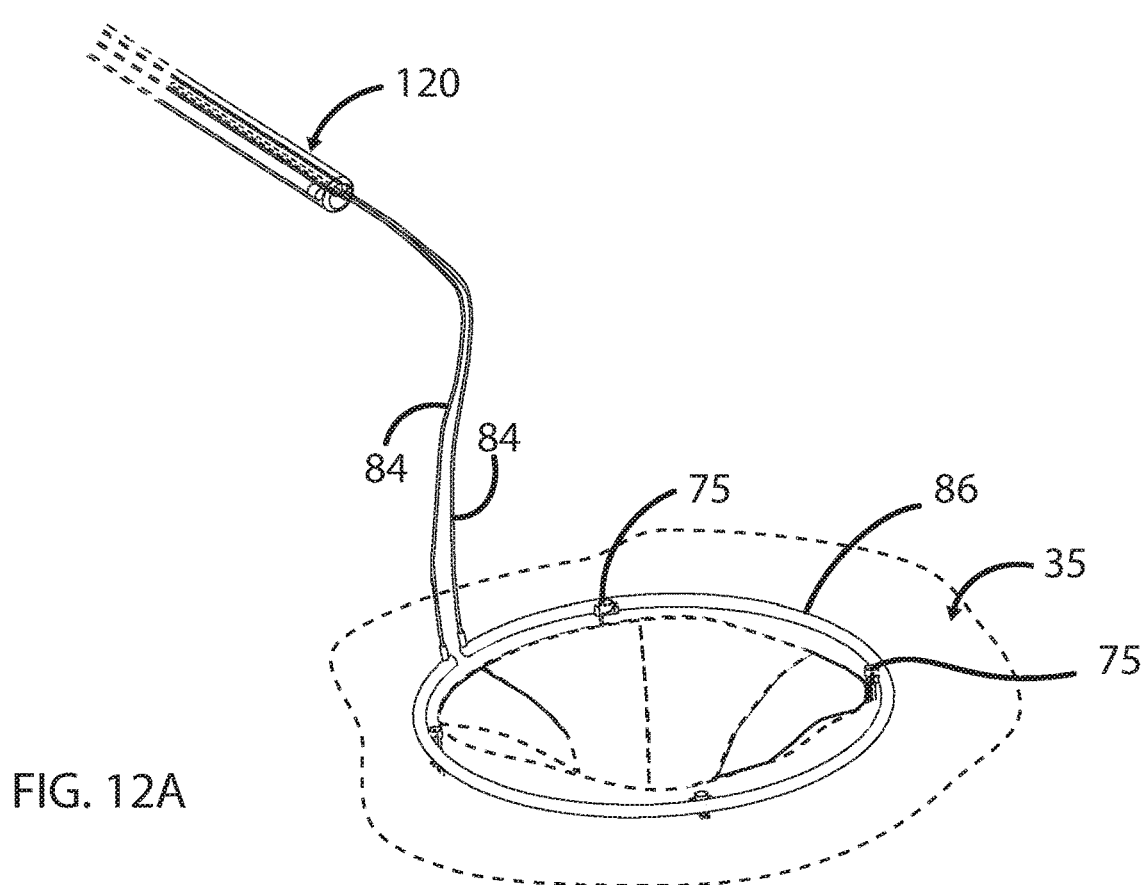
FIG. 12A depicts a cord protector while it is being slid in a distal direction over the proximal portions of the cinching cord.
Figure 12B:
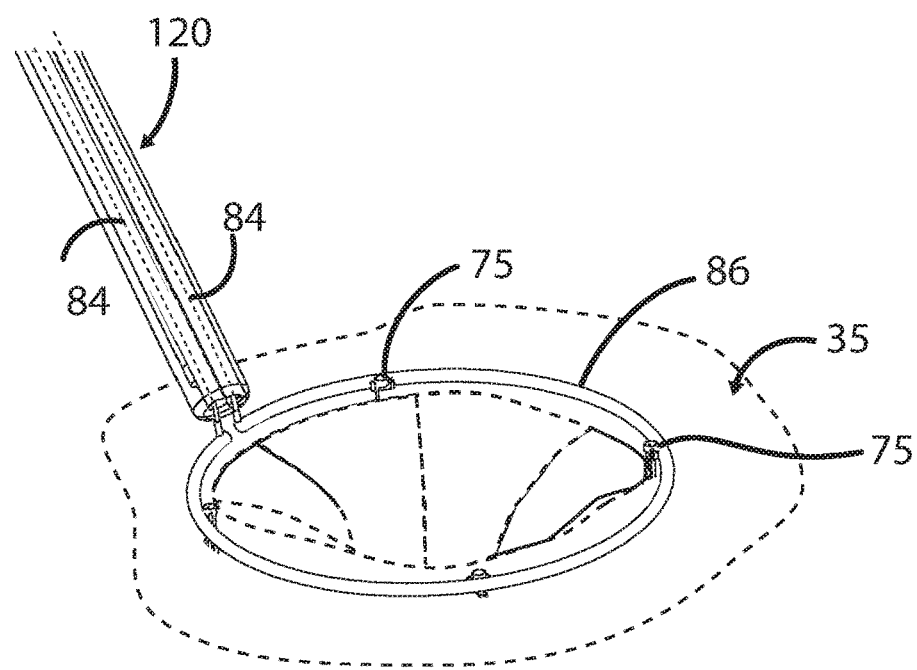
FIG. 12B depicts the cord protector of FIG. 12A after reaching the distal loop portion of the cinching cord.

In step S25, which is optional, a stiffening member (e.g., a metal wire) is slid in a proximal to distal direction through a third lumen that runs through the elongated cord protector. Then, in step S30, the first and second proximal portions of the cinching cord are covered with the cord protector which is made from a material that resists tissue ingrowth. The covering step may be implemented by sliding an elongated cord protector with two lumens over the first and second proximal portions of the cinching cord so that the proximal portions of the cinching cord pass through the lumens (as depicted in FIG. 12A and FIG. 12B).

After the anchoring step and the covering step, in step S40 we wait for tissue ingrowth to strengthen a bond between the distal loop portion of the cinching cord and at least one of the annulus and the tissue adjacent to the annulus. In some embodiments, the waiting step comprises waiting at least two weeks. But it is often preferable to wait at least two months to ensure that the bond is strong enough to withstand cinching. In many cases, waiting at least three months is advisable to ensure that the bond is strong enough to withstand cinching.

Figure 13A:
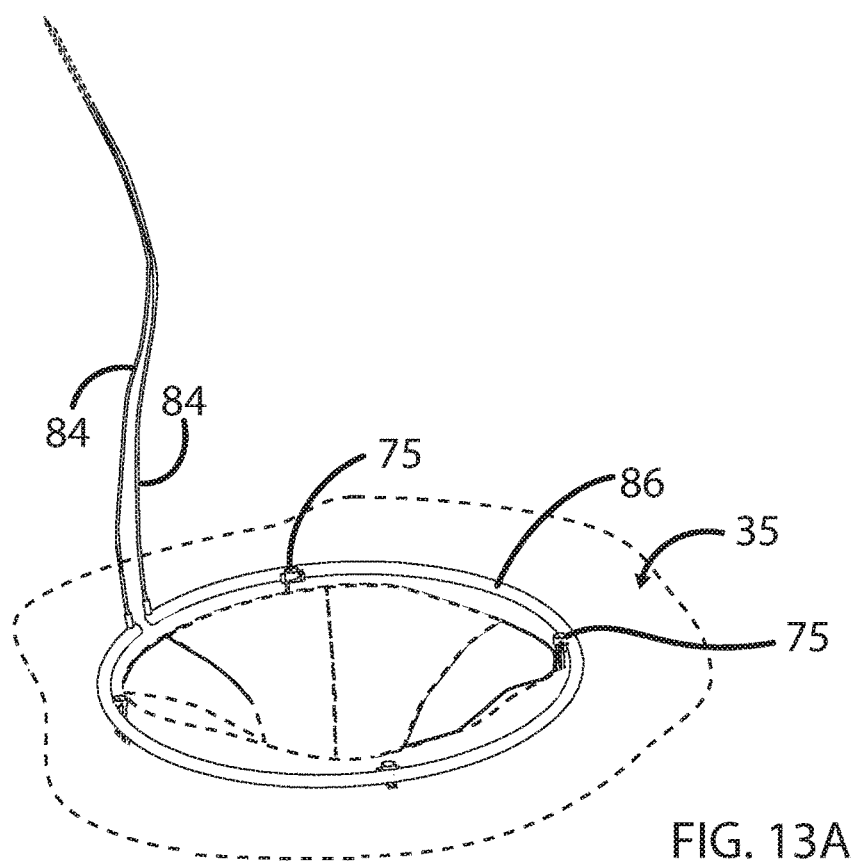
FIG. 13A depicts the cinching cord of FIG. 12A after the cord protector has been withdrawn.

After the waiting step, the cord protector is removed in step S50 (as depicted in FIG. 13A).

Figure 13B:
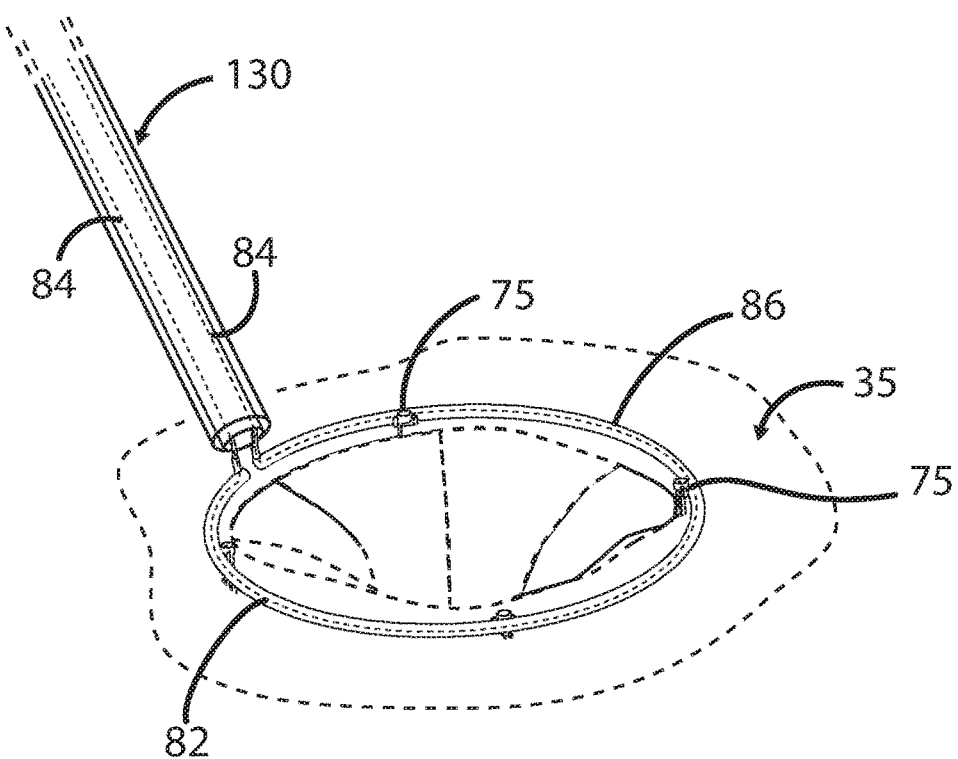
FIG. 13B depicts the cinching cord of FIG. 12A after a thrust tube has slid over the proximal portions of the cinching cord and reached the distal loop portion of the cinching cord.

The annulus is then cinched in step S60 by pulling the first and second proximal portions of the cinching cord so as to reduce a diameter of the annulus. Cinching may be implemented by advancing a thrust tube 130 in a distal direction over the first and second proximal portions 84 of the cinching cord until the thrust tube 130 reaches the distal loop portion 82 of the cinching cord and subsequently pressing the thrust tube 130 in a distal direction while pulling the first and second proximal portions 84 of the cinching cord in a proximal direction (as depicted in FIG. 13B).

After the cinching step, the cinching cord is fastened in step S70 so that the cinching cord holds the annulus in a reduced diameter state. This step may be implemented by fastening two portions of the cinching cord together using at least one of a knot, a clamp, and a crimped fastener.

Note that FIGS. 2 and 6 depicts the support arms 72 holding the distal loop portion 82 of the cinching cord in a round configuration prior to implantation, and FIGS. 8, 12, and 13 show the distal loop portion 82 in a round configuration subsequent to implantation. In alternative embodiments (e.g. for installation in a human mitral valve annulus, which is D-shaped) the support arms 72 are shaped to hold the distal loop portion 82 of the cinching cord in a D-shaped configuration prior to implantation, which will result in a D-shaped distal loop portion 82 subsequent to implantation.

FIG. 14 depicts an alternative embodiment that is similar to the FIG. 1-8 embodiment discussed above, except that the FIG. 14 embodiment includes a second balloon mounted on a second shaft. More specifically, the FIG. 14 embodiment adds a second shaft 108 that is slidably disposed within the main channel 55. This second shaft had a second inflation lumen. The FIG. 14 embodiment also adds an inflatable second balloon 107 mounted to the second shaft 108 and connected to the second inflation lumen so as to permit inflation of the second balloon 107 via the second inflation lumen. The second balloon 107 is disposed distally beyond the first balloon 105. The second shaft 108 is preferably coaxially arranged with respect to the first shaft 106 (i.e., the shaft for the first balloon 105), with the first shaft 106 disposed and configured so that both shafts can move independently in a proximal-to-distal direction.

In some preferred embodiments, the second shaft 108 is the innermost shaft, and the first shaft 106 (shown in FIG. 3) coaxially surrounds the second shaft 108, and the core 50 (also shown in FIG. 3) coaxially surrounds the first shaft 106. Optionally, a lumen (not shown) dimensioned to accommodate a guidewire may be disposed within the second shaft 108. In some preferred embodiments, this lumen is dimensioned to accommodate a 0.035 inch diameter guidewire.

In some embodiments (including the embodiment depicted in FIG. 14), the second shaft 108 extends distally beyond the nosecone 100 and the second balloon 107 is located distally beyond the nosecone 100. In these embodiments, the nosecone 100 may be mounted to the second shaft 108 (i.e. the same shaft to which the second balloon 107 is mounted), or alternatively, the nosecone 100 may be mounted on its own dedicated third shaft (not shown). In the latter situation, the third shaft is preferably slidably disposed within the main channel 55, and the nosecone 100 is movable between a proximal position and a distal position by slidably adjusting the position of the third shaft. The third shaft is preferably coaxially arranged with respect to the first shaft 106 and the second shaft 108, and configured so that all three shafts can move independently in a proximal-to-distal direction.

In alternative embodiments (not shown) the nosecone 100 is located distally beyond the second balloon 107. In these embodiments, the nosecone 100 may be mounted to a portion of the same second shaft 108 that extends distally beyond the second balloon 107.

It is preferable to launch the anchor launchers 74 when the distal ends of the anchor launchers are pressed against the annulus or against the tissue adjacent to the annulus, and the second balloon 107 can be used in different ways to help press the anchor launchers against the annulus or tissue depending on the anatomical context in which the cinching cord is being installed.

In one example, when the cinching cord is being installed at the tricuspid valve annulus, the distal assembly 70 (shown in FIG. 6B) is positioned in the right atrium and the second balloon 107 (shown in FIG. 14) is advanced in the deflated state into the pulmonary artery past the bifurcation (i.e., into the right pulmonary artery or into the left pulmonary artery). The second balloon 107 is then inflated. When the second balloon 107 is inflated at this position, it will act as a temporary anchor to assist in maneuvering the distal assembly 70 toward the annulus plane and gently press the ring against the annulus during anchor deployment.

In another example, when the cinching cord is being installed at the mitral valve annulus, when the second balloon 107 is positioned near the middle of the subject's ventricle (e.g., the left ventricle 33) and inflated, movement of the heart walls and/or movement of the blood traveling through the heart during a selected portion of the cardiac cycle (e.g., one of systole, diastole, etc.) will exert a force that urges the second balloon 107 towards the apex of the heart. This phenomenon can be taken advantage of to press the distal ends of the anchor launchers 74 against the annulus. The second balloon 107 and the assembly that includes the anchor launchers 74 are supported by the same supporting member (e.g., the core 50 depicted in FIG. 3). The triggering of the anchor launchers 74 can then be timed to coincide with the pressing that occurs during the selected portion of the cardiac cycle.

Figure 14:
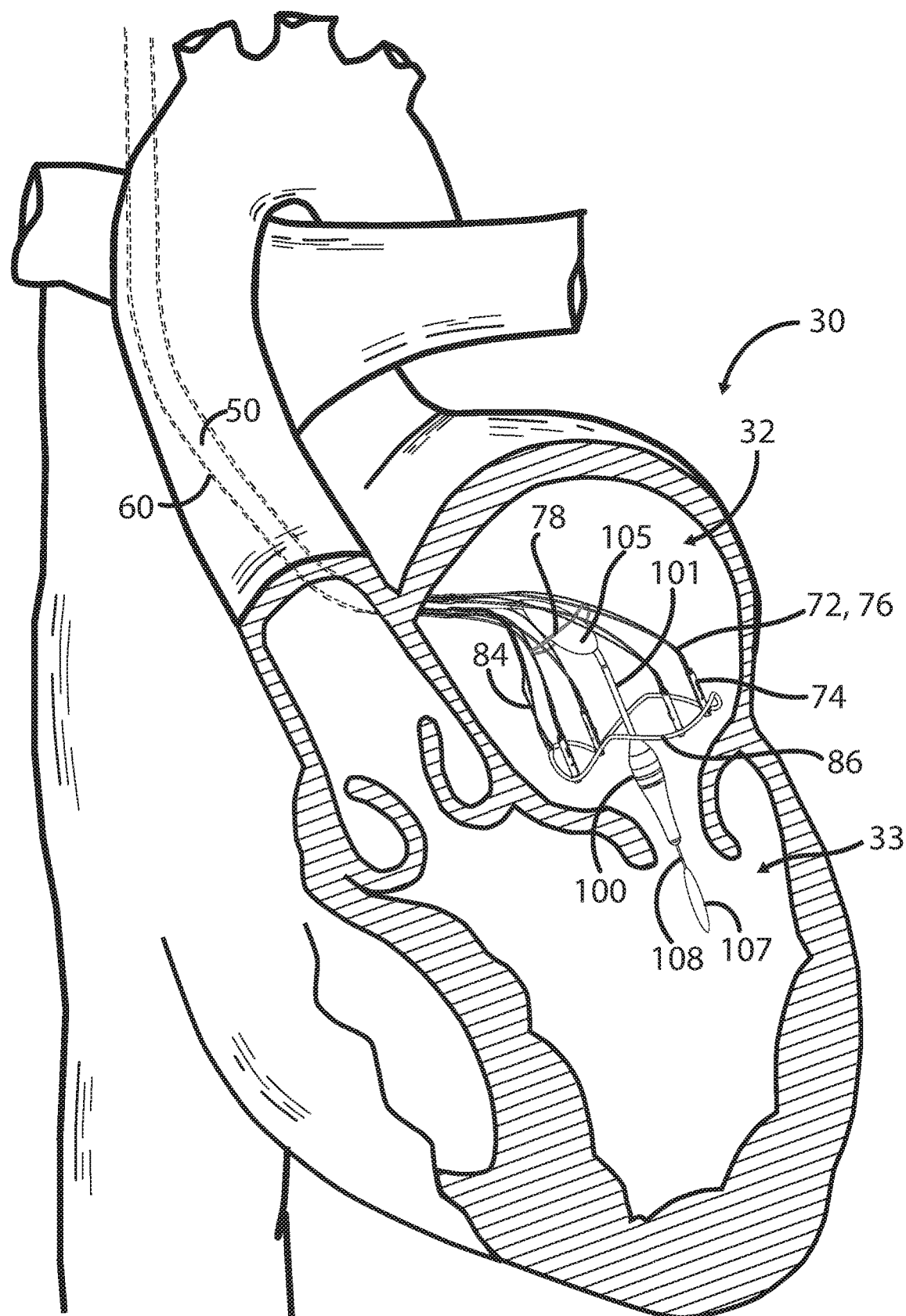
FIG. 14 depicts a variation of the FIG. 3 embodiment that has an additional balloon.
Figure 15:
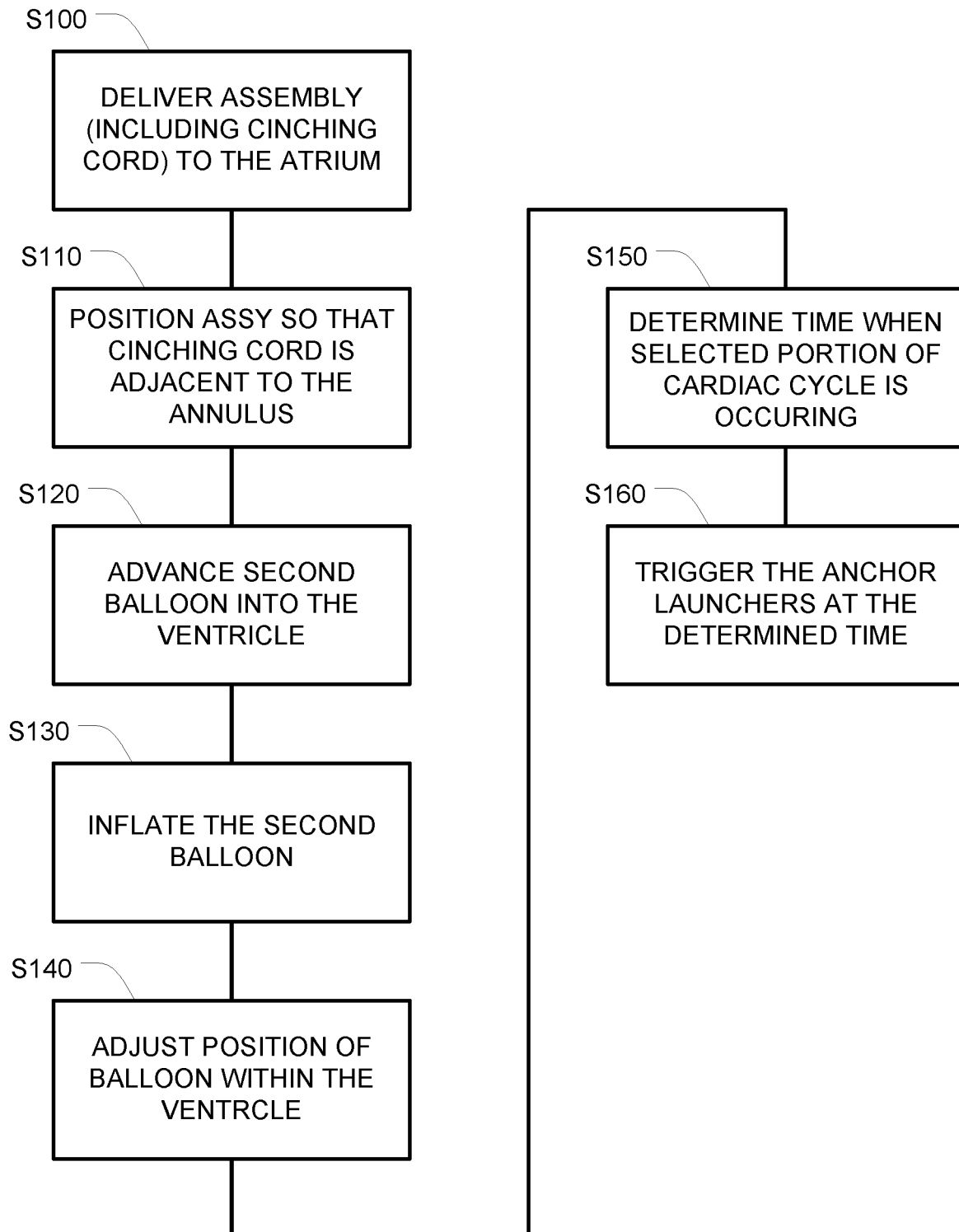
FIG. 15 is a flowchart of a method for using the FIG. 14 embodiment.

FIG. 15 is a flowchart of a method for using the dual-balloon embodiment of FIG. 14 to implement a method for implanting an annulus ring or a cinching cord to a heart valve annulus (or into tissue adjacent to the annulus). The annulus is disposed between an atrium and a ventricle of the heart. This method includes step S100 in which an assembly is delivered into the atrium. The assembly includes (a) the annulus ring or the cinching cord, (b) a plurality of anchors connected to the annulus ring or the cinching cord, and (c) a plurality of anchor launchers configured to launch the anchors into the annulus or into the tissue adjacent to the annulus. The assembly is supported by a supporting member (e.g., the core 50, shown in FIG. 3).

Next, in step S110, the assembly is positioned such that the annulus ring or the cinching cord is adjacent to the annulus or the tissue adjacent to the annulus on the atrium side of the annulus. In step S120, an inflatable balloon is advanced into the ventricle. The balloon is supported by the same supporting member that supports the assembly. In step S130, the balloon is inflated while the balloon is in the ventricle. The position of the balloon within the ventricle is adjusted in step S140 so that when the selected portion of the cardiac cycle occurs while the balloon is inflated, forces on the balloon will urge the balloon toward the apex of the heart, which will urge the supporting member toward the apex of the heart, which will urge the annulus ring or the cinching cord towards the annulus or towards the tissue adjacent to the annulus. Next, in step S150, while the inflated balloon is at the adjusted position, a time when the selected portion of the cardiac cycle is occurring is determined.

The anchor launchers are triggered in step S160 (e.g., by actuating the trigger 47 after removal of the locking pin 48, both shown in FIG. 5C) so that the anchor launchers launch the anchors into the annulus or into the tissue adjacent to the annulus during the selected portion of the cardiac cycle while the inflated balloon is at the adjusted position.

In some embodiments, the determining in step S150 comprises detecting when the supporting member is being pulled in a distal direction. In some embodiments, the advancing in step S120 comprises sliding a shaft to which the inflatable balloon is mounted in a distal direction with respect to the supporting member. In some embodiments, the positioning in step S110 comprises inflating the first balloon 105 between a plurality of support arms 72 that support the anchor launchers 74 so that the additional balloon 105 pushes the support arms 72 away from each other (as depicted above in FIG. 7C).

In some embodiments, the delivering in step S100 comprises introducing the annulus ring or the cinching cord, the anchors, and the anchor launchers into the atrium while the cinching cord, the anchors, and the anchor launchers are collapsed within an outer sleeve; and retracting the outer sleeve so that the cinching cord, the anchors, and the anchor launchers extend beyond a distal end of the outer sleeve.

Figure 16:
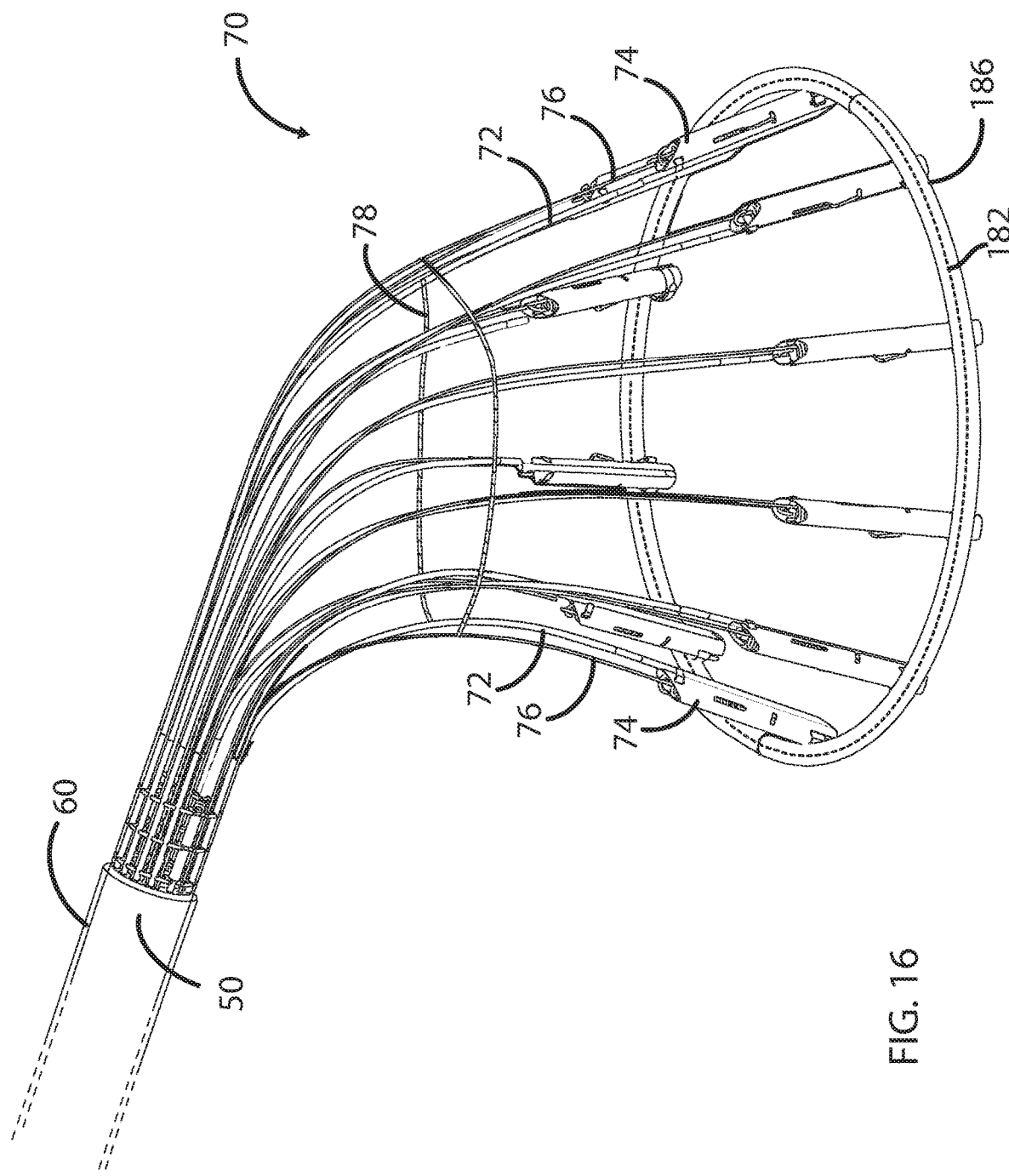
FIG. 16 depicts a variation of the FIG. 6A embodiment in which the cinching cord has been replaced by an annulus ring.

FIG. 16 depicts a variation of the FIG. 6A embodiment in which the cinching cord has been replaced by an annulus ring. In this embodiment, instead of implanting the distal loop portion 82 of a cinching cord into the annulus so that the proximal portions 84 of the cinching cord extend back through the core 50 (as described above in connection with FIG. 6A), a closed annulus ring 182 is implanted into the annulus or into tissue adjacent to the annulus. Preferably, the annulus ring 182 is surrounded by a sleeve 186 in a manner similar to the way that the distal loop portion 82 of the cinching cord was enclosed in a sleeve 86 in the FIG. 6A embodiment. Similarly, the cinching cord in any of the other embodiments discussed above can be replaced with an annulus ring.

When the apparatus 25 described above in connection with FIGS. 1-9 and 14 is withdrawn from the patient's body, the possibility exists that a component (e.g., the anchor launchers 74, the support arms 72, the balloon 105, the outer sleeve 60, etc.) that is moving in a proximal direction will grab against the proximal portions of the cinching cord 84. (See, for example, FIGS. 8A and 8B.) If this occurs, the forces on the proximal portions of the cinching cord 84 would pull on the distal loop portion of the cinching cord 82, and those forces might be sufficient to dislodge one or more of the anchors 75 from the annulus 35.

Figure 17:
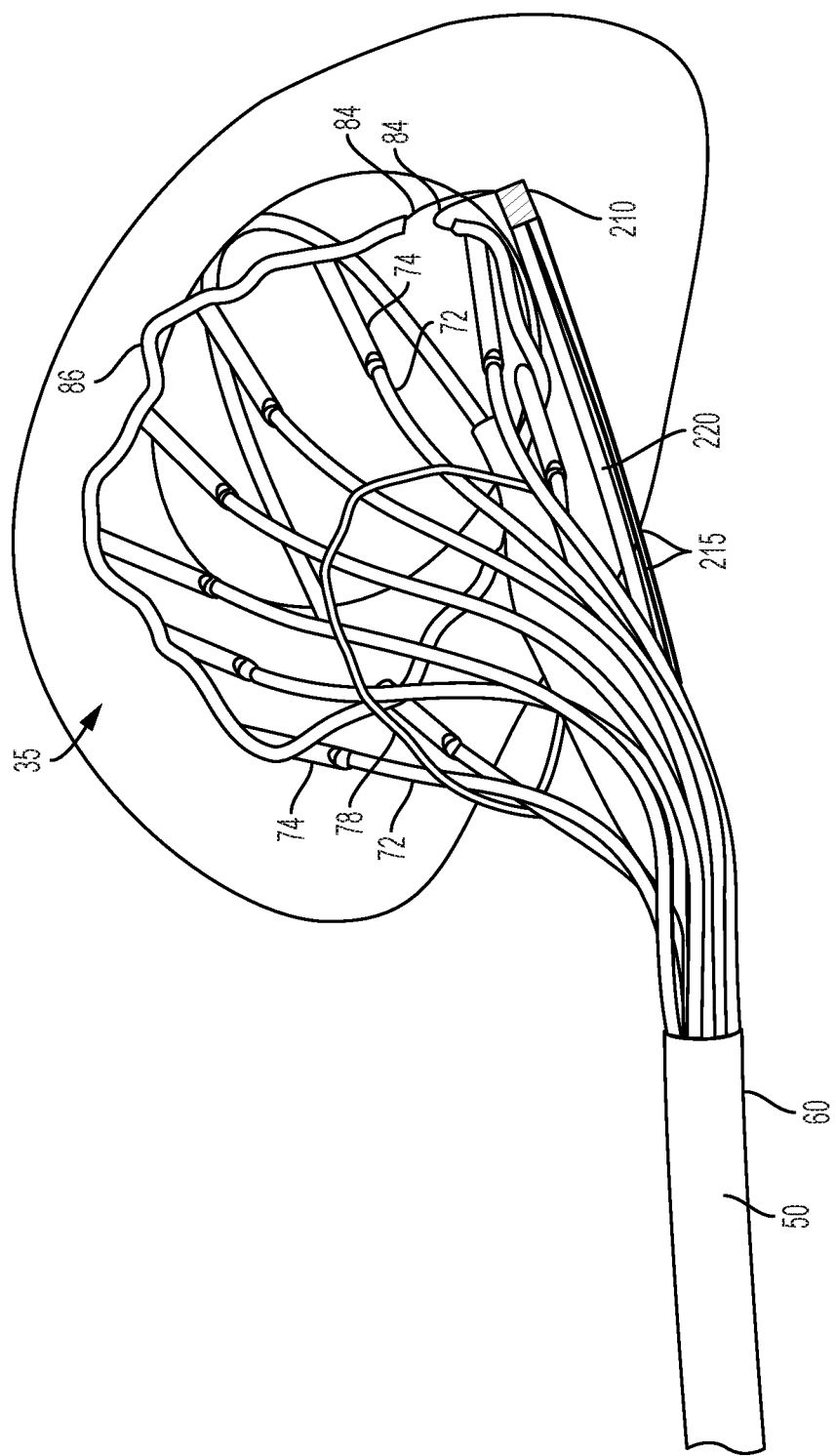
FIG. 17 depicts another embodiment of an apparatus for installing a cinching cord that reduces the risk of dislodgment.
Figure 18:
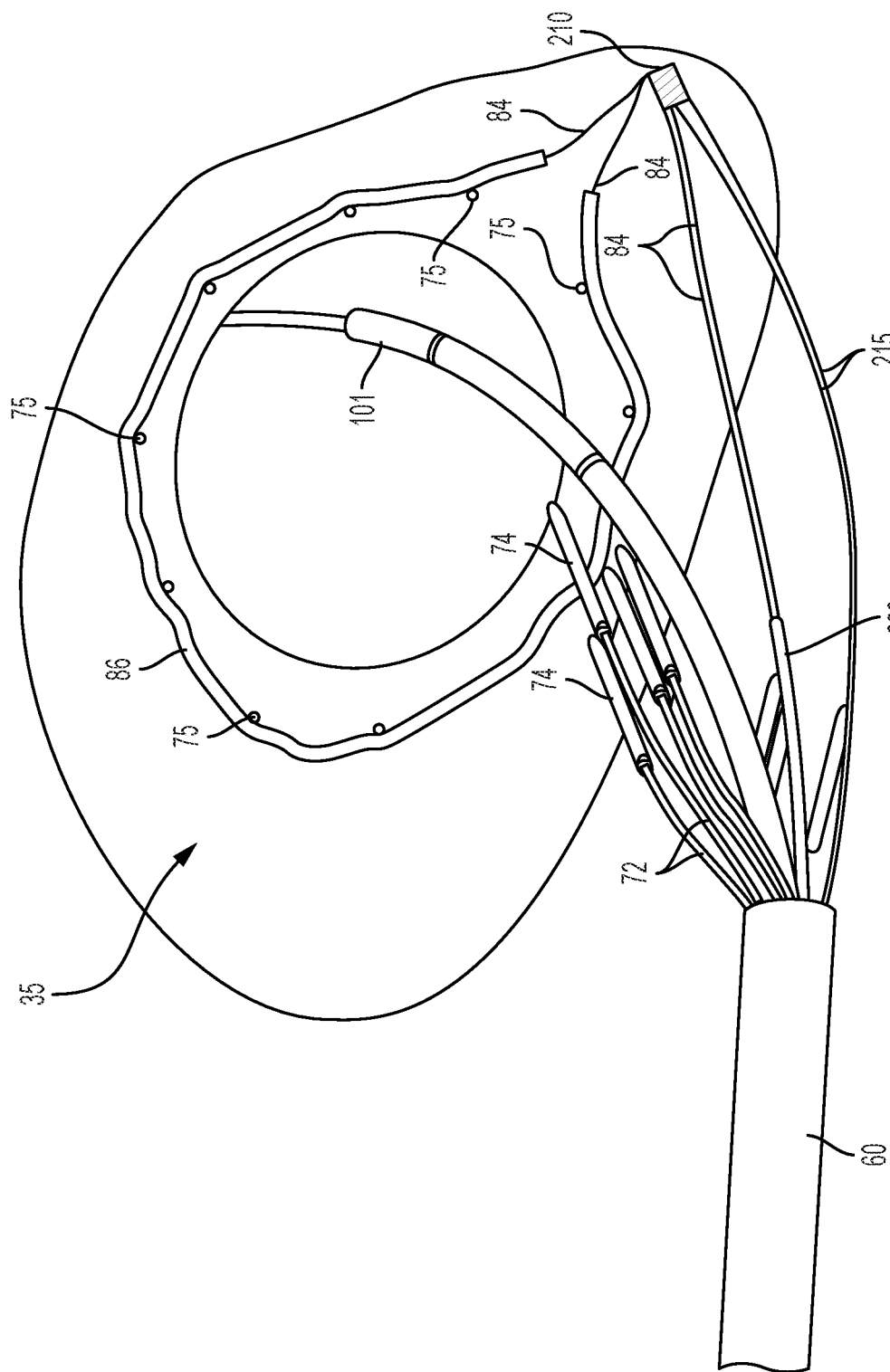
FIG. 18 depicts the FIG. 17 embodiment after the anchors have been implanted and withdrawal of the apparatus has begun.

FIGS. 17 and 18 depict one optional approach to prevent dislodgment of the anchors 75 in these circumstances. This embodiment is similar to the FIG. 1-9 embodiment described above, but adds additional components 210-222 reduce the risk of dislodgment. FIG. 17 depicts the distal portion of the apparatus just prior to launching of the anchors 75 from the anchor launchers 74; and FIG. 18 depicts the same apparatus after the anchors 75 have been implanted in the annulus 35 and withdrawal of the apparatus has begun.

As best seen in FIGS. 1, 3, and 4A, the apparatus includes a housing 40 and an elongated core 50 mounted with respect to the housing 40. The core has at least one second channel 52 that runs through the core in a proximal-to-distal direction, and at least one fourth channel (not shown) that runs through the core in a proximal-to-distal direction. These fourth channels resemble the second channels 52 described above in connection with FIG. 4A. In some preferred embodiments, there are two second channels and two fourth channels.

A cinching cord has a distal loop portion and first and second proximal portions 84. The proximal portions of the cinching cord are slidably disposed within the at least one second channel and extend distally beyond the distal end of the core. In some preferred embodiments, each proximal portion of the cinching cord is disposed within its own individual lumen.

Turning now to FIG. 17, at least four support arms 72 are mounted to the core and extend distally beyond the distal end of the core. At least four anchors 75 (shown in FIG. 18) are configured to anchor the distal loop portion of the cinching cord into the annulus or into the tissue adjacent to the annulus. (Note that in FIG. 17, the distal loop portion of the cinching cord is covered by a sleeve 86 of material that promotes tissue ingrowth.) At least four anchor launchers 74 are supported by a respective one of the support arms 72, and each anchor launcher is configured to launch a respective one of the anchors into the annulus or into the tissue adjacent to the annulus.

At least one wire 215 is slidably disposed within the at least one fourth channel. Each of these wires has a distal end that extends distally beyond the distal end of the core, and has a proximal end that extends proximally beyond the fourth channel. In some preferred embodiments, the at least one wire comprises two wires, and the at least one fourth channel comprises two channels, with each of the two wires slidably disposed within a respective one of the two channels. In some preferred embodiments, each of these wires 215 is a Nitinol wire with a diameter between 0.3 and 0.5 mm (e.g., 0.4 mm).

A pushing member 210 is affixed to the distal end of the at least one wire 215 such that pushing the proximal end of the at least one wire 215 in a distal direction will push the pushing member 210 in a distal direction. In some embodiments (including the FIG. 17 embodiment), the pushing member 210 is a hollow cylinder aligned so that an axial axis of the hollow cylinder is parallel to the at least one wire 215, and the first proximal portion and the second proximal portion of the cinching cord 84 pass through the interior of the hollow cylinder and are slidably disposed therein. In some embodiments, the pushing member 210 is a hollow cylinder that is laser cut from a nitinol tube with an outer diameter between 1.25 and 2 mm (e.g., 1.63 mm). In some embodiments, the hollow cylinder has relatively large wall thickness (e.g., 0.23 mm), and the edges of the cylinder are radiused (e.g., by electropolishing) to reduce the risk of damaging the proximal portions of the cinching cord 84 when those proximal portions slide through the cylinder.

It is preferable to use a plurality of wires 215 that terminate on the pushing member 210 (as compared to a single wire 215) to improve pushability and stability.

The FIG. 17/18 embodiment also includes an optional crush resistant channel 220 disposed distally beyond the distal end of the core. Preferably, the inner walls of the crush resistant channel 220 are made from a low friction material. The first and second proximal portions of the cinching cord 84 are slidably disposed within this crush resistant channel. Preferably, the space between the distal end of the core and the proximal end of the crush resistant channel is kept as small as possible. In some embodiments, this crush resistant channel 220 is configured so that prior to launching of the anchors, the crush resistant channel 220 extends all the way to the pushing member 210, as depicted in FIG. 17. One suitable approach for implementing this crush resistant channel 220 is to use a Pebax tube reinforced by a polyester braid, with an inner diameter on the order of 1 mm. The crush resistant channel 220 prevents the support arms 72 and the anchor launchers 74 from grabbing against the proximal portions of the cinching cord 84 (which passes through the crush resistant channel 220) when those components 72, 74 are withdrawn.

In some embodiments, the crush resistant channel 220 is supported by at least one support arm that is affixed to the core. These support arms may have a similar construction to the support arms 72 that hold the anchor launchers 74, and may be connected to the core in the same way as those support arms 72, as described above. The crush resistant channel 220 may be attached to its support arm using, for example, heat shrink tubing and/or an adhesive.

After the anchor launchers have been maneuvered to the desired position adjacent to the annulus 35, launching of the anchors proceeds in the same way as described above in connection with FIGS. 7A-7D.

Turning now to FIG. 18, after the anchors have been launched, the distal loop portion of the cinching cord (which, in FIG. 18, runs through the interior of sleeve 86) is anchored to the annulus 35 (or into the tissue adjacent to the annulus) by the anchors 75. The core is then pulled back through the outer sleeve 60, which causes the support arms 72 and the crush resistant channel 220 to move in a proximal direction. While the core is pulled back, an operator pushes the wires 215 in a distal direction, which will urge the pushing member 210 against the tissue of the annulus 35, as depicted in FIG. 18. Because the proximal portions of the cinching cord 84 are threaded through a passage that extends through the pushing member 210 in a proximal to distal direction (e.g. the interior of a hollow cylinder), the distal end of the pushing member will hold the proximal portions of the cinching cord 84 against the tissue. This will hinder dislodgement of the anchors 75 during the movement of the housing in the proximal direction, by eliminating (or at least reducing) forces that might otherwise tend to pull the anchors 75 out of the tissue.

Progressive movement of the housing 40 (shown in FIG. 1) in a proximal direction will cause the core 50 (also shown in FIG. 1) to progressively move in a proximal direction with respect to the first and second proximal portions of the cinching cord 84. The point in time depicted in FIG. 18 is when the core has been withdrawn a few centimeters, so that the support arms 72 and the anchor launchers 74 begin to collapse and are pulled back into the outer sheath 60. Because the proximal portions of the cinching cord 84 pass through the crush resistant channel 220, that channel will protect the proximal portions of the cinching cord 84 from being grabbed by the support arms 72 and the anchor launchers 74 when those components are moved in a proximal direction.

Withdrawal of the entire apparatus then proceeds while the operator continues to press the wires 215 in a distal direction. Once the entire apparatus 25 has been removed, the operator can release the distal pressure on the wires 215, and pull those wires out of the patient's body in a proximal direction. The wires 215 will pull the pushing member 210 out of the patient's body. As this occurs, the proximal portions of the cinching cord 84 will slide through the passage in the interior of the pushing member 210 until the pushing member 210 has been completely withdrawn.

Figure 19:
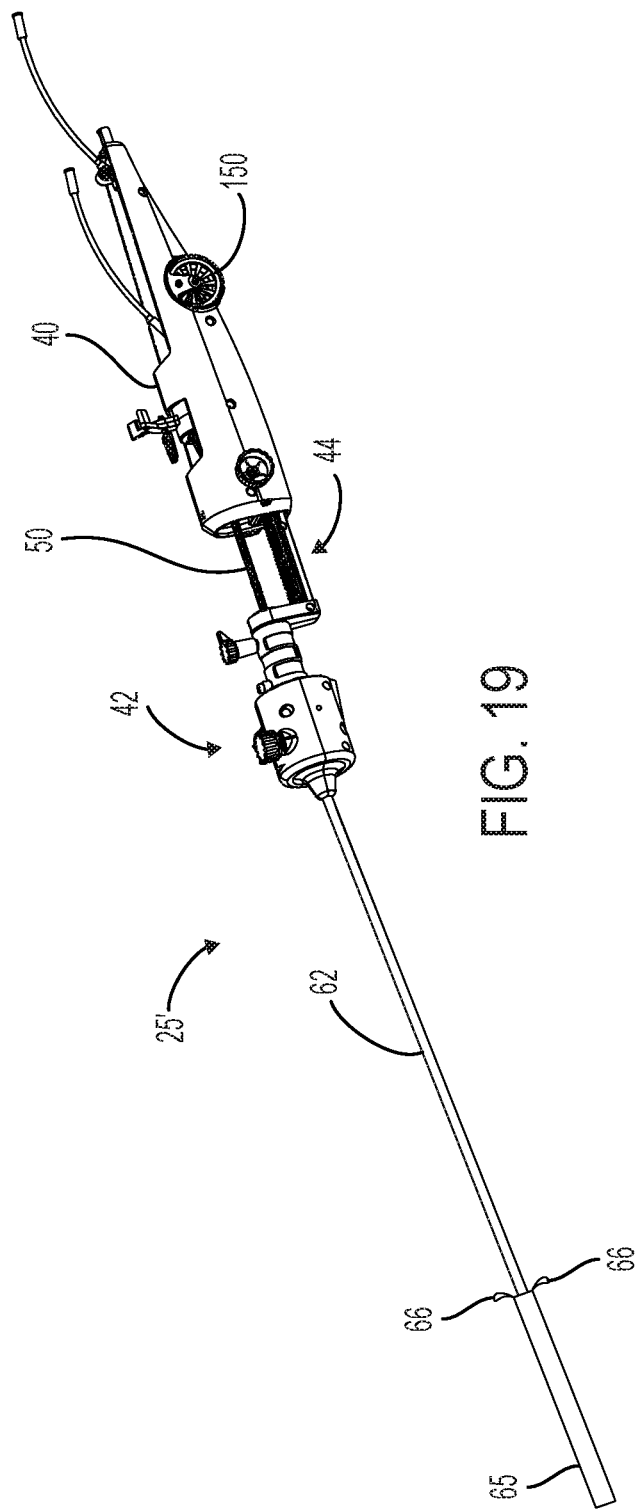
FIG. 19 depicts another embodiment that is similar to the FIG. 14 embodiment but uses a two-part sleeve and omits the nosecone.

FIG. 19 depicts another embodiment that is similar to the embodiment described above in connection with FIG. 14, but (a) deletes the nosecone from the FIG. 14 embodiment; and (b) replaces the outer sleeve 60 of the FIG. 14 embodiment with a two-part sleeve that includes a first sleeve 62 and a second sleeve 65. Note that this two-part sleeve configuration may be used in place of the single outer sleeve 60 in any of the embodiments described herein.

The first sleeve 62 in the FIG. 19 embodiment is similar to the outer sleeve 60 in the FIG. 14 embodiment, except that the first sleeve 62 is shorter than the outer sleeve 60 in the FIG. 14 embodiment. More specifically, the length of the first sleeve 62 is such that even when the first sleeve 62 is in its most extended position, the anchor launchers are not covered by the first sleeve 62.

A second sleeve 65 is disposed at the distal end of the apparatus, and this second sleeve 65 covers the distal end of the first sleeve 62 and extends distally beyond the distal end of the first sleeve 62 to cover the anchor launchers. The inner diameter of the second sleeve 65 is slightly larger than the outer diameter of the first sleeve 62 in order to permit the first sleeve 62 to slide within the second sleeve 65. The second sleeve 65 is preferably configured so that it can be torn apart (e.g., by pulling on tabs 66) and removed. An example of a commercially available component that is suitable for use as the second sleeve 65 is the 22 French outer sleeve component from the Cook Medical Peel-Away® introducer set (Ref. Nos. C-PLI-22.0-38 and G04518).

This embodiment is particularly useful for accessing the tricuspid annulus when used in conjunction with an introducer sheath such as the GORE® DrySeal Sheath, which should have the same outer diameter as the second sleeve 65 (e.g., 22 French). To access the tricuspid annulus using this embodiment, the distal end of a GORE® DrySeal Sheath is introduced via the jugular and advanced until it enters the right atrium. A guide wire is then routed through the DrySeal Sheath, through the annulus into the right ventricle, and into the pulmonary artery until it passes the bifurcation in the pulmonary artery in either direction, and enters either the right pulmonary artery or the left pulmonary artery.

The distal balloon 107 (shown in FIG. 14) is advanced over the guidewire and into the DrySeal Sheath. The entire device (including, but not limited to the second sleeve 65) is then advanced in a distal direction until the distal end of the second sleeve 65 reaches the proximal entrance of the DrySeal Sheath. Because the outer diameter of the second sleeve 65 is the same as the outer diameter of the DrySeal Sheath, the second sleeve 65 will not be able to move into the DrySeal Sheath. The distal balloon 107 is threaded over the guidewire. Next, the entire device except for the second sleeve 65 (which is blocked by the DrySeal Sheath) is advanced in a distal direction, so that the first sleeve 62 slides in a distal direction within the second sleeve 65. The distal assembly 70 will slide through the second sleeve 65 and into the DrySeal Sheath, after which the distal end of the first sleeve 62 will slide into the DrySeal Sheath. At this point, the operator pulls on the tabs 66 of the second sleeve 65 and removes that sleeve. Subsequently, advancing of the entire device continues until the distal assembly 70 exits the distal end of the DrySeal Sheath. At this point, the DrySeal Sheath may be withdrawn a few centimeters to improve maneuverability of the distal assembly 70 within the right atrium.

The distal assembly 70 is then advanced with respect to the first sleeve 62 and the DrySeal Sheath, until the support arms 72 can pop open due to spring action or a shape-memory effect. The distal balloon is then moved into the pulmonary artery beyond the bifurcation in either direction and inflated. The orientation of the distal assembly 70 is adjusted e.g., using the controls 42 or by moving the entire housing 40 so as to approach the annulus. Fluoro guidance may be used for this purpose, optionally relying on the radio opaque sleeves 98. The proximal balloon 105 is inflated to help spread the support arms 72 and so that the distal assembly will move as a single unit. Optionally, the shaft 106 of the proximal balloon 105 may be locked at this point. Additional adjustments to the orientation of the distal assembly are made, and the anchors are launched by actuating the trigger 47 for the spring-loaded actuator 46.

Pressure is applied to the pushing member 210 by pushing the wires 215 distally, the balloons are deflated, and the DrySeal Sheath is advanced in a distal direction until the support arms 72 begin to collapse. The entire device is then withdrawn by moving the housing 40 in a proximal direction. The distal pressure on the pushing member 210 will squeeze the proximal portions of the cinching cord 84 against the tissue, which will prevent dislodgment of the anchors as described above. Continued withdrawal of the housing 40 will pull the support arms and the anchor launchers 74 in a proximal direction through the DrySeal Sheath (while pushing on the pushing member 210 continues) until only the cinching cord 82, 84 the surrounding sleeve 86, the anchors 75, the pushing members 210, and the pushing wires 215 remain. Finally, the pushing members 210, the pushing wires 215, and the DrySeal Sheath are withdrawn.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for delivering an annulus ring or a cinching cord to the vicinity of an annulus, the apparatus comprising:

an elongated core having a distal end and a channel that runs through the elongated core in a proximal-to-distal direction;
at least four support arms mounted to the elongated core that extend distally beyond the distal end of the elongated core;
at least four anchor launchers, each of the anchor launchers having a distal end, wherein each of the anchor launchers is supported by a respective one of the support arms;
a first shaft disposed within the channel, the first shaft having a first inflation lumen;
an inflatable first balloon mounted to the first shaft and connected to the first inflation lumen so as to permit inflation of the first balloon via the first inflation lumen, wherein the first balloon is configured so that when the first balloon is inflated at a first position, the first balloon will push the support arms away from each other;
a second shaft slidably disposed within the channel, the second shaft having a second inflation lumen; and
an inflatable second balloon mounted to the second shaft and connected to the second inflation lumen so as to permit inflation of the second balloon via the second inflation lumen, wherein the first shaft and the second shaft are coaxial while the first balloon and the second balloon are both in a deflated state prior to inflation of either balloon, and the second balloon is disposed distally beyond the first balloon.

2. The apparatus of claim 1, wherein the first shaft is slidably disposed within the channel, and the first balloon is movable to the first position by slidably adjusting a position of the first shaft.

3. The apparatus of claim 2, wherein the first balloon is movable to a second position that is within the channel and proximal of the support arms by slidably adjusting a position of the first shaft.

4. The apparatus of claim 1, further comprising an outer sleeve disposed around the elongated core, the outer sleeve having a distal end,
wherein the outer sleeve is slidable with respect to the elongated core between an extended position and a retracted position,
wherein, when the outer sleeve is in the extended position, the support arms, the anchor launchers, and the first balloon are disposed within the outer sleeve, and
wherein, when the outer sleeve is in the retracted position, the anchor launchers and at least a portion of the support arms extend distally beyond the distal end of the outer sleeve.

5. The apparatus of claim 4, further comprising a nosecone that is movable between a proximal position and a distal position, such that when the nosecone is in the proximal position and the outer sleeve is in the extended position, the nosecone is disposed at the distal end of the outer sleeve.

6. The apparatus of claim 5, wherein the second shaft extends distally beyond the nosecone and the second balloon is located distally beyond the nosecone.

7. The apparatus of claim 5, wherein the nosecone is mounted to the second shaft, and the nosecone is movable between the proximal position and the distal position by slidably adjusting a position of the second shaft.

8. The apparatus of claim 5, wherein the first shaft is slidably disposed within the channel, wherein the first balloon is movable to the first position by slidably adjusting a position of the first shaft, wherein the second shaft extends distally beyond the nosecone and the second balloon is located distally beyond the nosecone, wherein the nosecone is mounted to the second shaft, and wherein the nosecone is movable between the proximal position and the distal position by slidably adjusting a position of the second shaft.

9. The apparatus of claim 5, further comprising a third shaft slidably disposed within the channel, wherein the nosecone is mounted to the third shaft, and the nosecone is movable between the proximal position and the distal position by slidably adjusting a position of the third shaft.

10. The apparatus of claim 5, wherein the nosecone is located distally beyond the second balloon.

11. The apparatus of claim 1, further comprising:
a cinching cord; and
at least four anchors, wherein each of the anchors is disposed in a respective one of the anchor launchers and connected to the cinching cord,
wherein the support arms are configured to hold the distal ends of the anchor launchers at positions that correspond to a shape of the annulus, with the distal ends of the anchor launchers distributed about a perimeter of the shape of the annulus.

12. The apparatus of claim 1, further comprising:
an annulus ring; and
at least four anchors, wherein each of the anchors is disposed in a respective one of the anchor launchers and connected to the annulus ring,
wherein the support arms are configured to hold the distal ends of the anchor launchers at positions that correspond to a shape of the annulus, with the distal ends of the anchor launchers distributed about a perimeter of the shape of the annulus.

13. The apparatus of claim 1, wherein the at least four support arms comprises at least eight support arms, and wherein the at least four anchor launchers comprises at least eight anchor launchers.

14. The apparatus of claim 1, wherein the annulus is a mitral valve annulus.

15. The apparatus of claim 1, wherein the annulus is a tricuspid valve annulus.

* * * * *